US010308691B2

(12) United States Patent
Liu et al.

(10) Patent No.: US 10,308,691 B2
(45) Date of Patent: Jun. 4, 2019

(54) **METHODS FOR TUNING CAROTENOID PRODUCTION LEVELS AND COMPOSITIONS IN *RHODOSPORIDIUM* AND *RHODOTORULA* GENERA**

(71) Applicant: TEMASEK LIFE SCIENCES LABORATORY LIMITED, Singapore (SG)

(72) Inventors: Yanbin Liu, Singapore (SG); Chong Mei Koh, Singapore (SG); Lianghui Ji, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 15/535,466

(22) PCT Filed: Dec. 14, 2015

(86) PCT No.: PCT/SG2015/050491
§ 371 (c)(1),
(2) Date: Jun. 13, 2017

(87) PCT Pub. No.: WO2016/099401
PCT Pub. Date: Jun. 23, 2016

(65) Prior Publication Data
US 2017/0362285 A1  Dec. 21, 2017

Related U.S. Application Data

(60) Provisional application No. 62/091,913, filed on Dec. 15, 2014.

(51) Int. Cl.
| C12N 15/80 | (2006.01) |
| C07K 14/37 | (2006.01) |
| C12P 23/00 | (2006.01) |
| C12N 9/02 | (2006.01) |
| C12N 15/113 | (2010.01) |
| C12P 21/02 | (2006.01) |

(52) U.S. Cl.
CPC ............ *C07K 14/37* (2013.01); *C12N 9/0008* (2013.01); *C12N 15/113* (2013.01); *C12N 15/80* (2013.01); *C12P 23/00* (2013.01); *C12P 21/02* (2013.01)

(58) Field of Classification Search
None
See application file for complete search history.

(56) References Cited

U.S. PATENT DOCUMENTS

2016/0032296 A1    2/2016  Cheng et al.

FOREIGN PATENT DOCUMENTS

| WO | 2006102342 A2 | 9/2006 |
| WO | 2014142747 A1 | 9/2014 |

OTHER PUBLICATIONS

International Search Report and Written Opinion dated Mar. 1, 2016 issued in PCT/SG2015/050491 (8 pages).
Paul Debarati et al.: "Genome Sequence of the Oleaginous Yeast *Rhodotorula glutinis* ATCC 204091", Genome Announcements., Feb. 2016, vol. 2, No. issue 1 (2 pages).
Morin, Nicolas et al.: "Draft Genome Sequence of *Rhodosporidium toruloides* CECT1137, an Oleaginous Yeast of Biotechnological Interest", Genome Announcements., Jul. 2014, vol. 2, issue 4 (2 pages).
Liu, Yanbin et al.: "Engineering an efficient and tight D-amino acid-inducible gene expression system in *Rhodosporidium/Rhodotorula* species", Microbial Cell Factories., 2015, vol. 14, article 170 (16 pages).
Guo, W. et al.: "Cloning and characterization of a phytoene dehydrogenase gene from marine yeast *Rhodosporidium diobovatum*", Antonie Van Leeuwenhoek., Jan. 2015, pp. 1017-1027 vol. 107, 2015 (11 pages).
European Communication dated May 7, 2018, issued in European Patent Application No. 15870471.8, 5 pages.
Bhosale et al., "Production of beta-carotene by a mutant of Rhodotorula glutinis", Applied Microbiology and Biotechnology, Springer, DE, 55(4) May 1, 2001, XP002442975, pp. 423-427.
Misawa et al., "Metabolic engineering for the production of carotenoids in non-carotenogenic bacteria and yeasts", Journal of Biotechnology, Elsevier, Amsterdam, NL, 59(3) Jan. 3, 1998, XP004113748, pp. 169-181.

*Primary Examiner* — Channing S Mahatan
(74) *Attorney, Agent, or Firm* — Rothwell, Figg, Ernst & Manbeck, P.C.

(57) ABSTRACT

The present invention relates to the field of fungal biotechnology, more particularly to genetic engineering methods for the production of carotenoids in fungal hosts selected from *Rhodospordium* and *Rhodotorula* genera.

16 Claims, 7 Drawing Sheets
Specification includes a Sequence Listing.

A

B

C

D

E

A

B

C

D

METHODS FOR TUNING CAROTENOID PRODUCTION LEVELS AND COMPOSITIONS IN *RHODOSPORIDIUM* AND *RHODOTORULA* GENERA

CROSS-REFERENCE TO RELATED APPLICATIONS

The present application is a national stage filing under 35 U.S.C. § 371 of PCT/SG2015/050491, filed on 14 Dec. 2015, which is related to and claims the benefit of priority to U.S. Provisional Application No. 62/091,913, filed 15 Dec. 2014. Each application is incorporated herein by reference in its entirety.

SEQUENCE SUBMISSION

The present application is being filed along with a Sequence Listing in electronic format. The Sequence Listing is entitled 2577244PCTSequenceListing.txt, created on 3 Nov. 2015 and is 184 kb in size. The information in the electronic format of the Sequence Listing is incorporated herein by reference in their entirety.

BACKGROUND OF THE INVENTION

The present invention relates to the field of fungal biotechnology, more particularly to genetic engineering methods for the production of carotenoids in fungal hosts selected from *Rhodospordium* and *Rhodotorula* genera.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

It is well documented that carotenoid production is initiated with the biosynthesis of geranylgeranyl diphosphate (GGPP) catalyzed by GGPP synthase for the condensation of $C_{15}$ farnesyl diphosphate (FPP) and $C_5$ isopentenyl diphophate (IPP). Subsequently, two molecules of GGPP are further condensed to form the colorless precursor phytoene, which is catalyzed by phytoene synthase. In fungi and eubacteria, phytoene desaturase catalyzes all 4 steps of desaturation of phytoene to yield the red colored lycopene while this is done by separate phytoene desaturase and γ-carotene or turase and desaturase in plant, algae and cyanabacteria. Lycopene is cyclized by carotene cyclase to form mono-cyclic γ-carotene and teneene cy, and dicyclic α-carotene and carotene a [1, 2]. Further upstream of the biosynthetic pathway, FPP is produced by farnesyl diphosphate synthase (FPS) catalyzed condensation of IPP and $C_{10}$ geranyl diphosphate (GPP), the latter produced by GPP synthase catalyzed condensation of IPP and dimethylallyl diphosphate (DMAPP), the product of IPP isomerase IPP and DMAPP can be synthesized via either the mevalonate pathway (MVP) or 2-C-methyl-D-erythritol 4-phosphate/1-deoxy-D-xylulose 5-phosphate pathway (MEP/DOXP) [3, 4].

Carotenoids are 40 carbon ($C_{40}$) tetraterpenoids [5]. The unoxygenated carotenoids, such as γ-carotene, β-carotene and lycopene are known as carotenes. Further enzymatic modifications of carotenes produce molecules containing oxygen, such as lutein, retinol (vitamin A), zeaxanthin and astaxanthin [6, 7]. Biosynthesis of carotenoids occur in all photosynthetic organisms [8] and many non-photosynthetic microorganisms, such as bacteria and fungi [1, 5, 9, 10], and some insects [11].

Carotenoids play important role in human and animal health and development [12-15]. For example, a higher dietary intake of carotenoids was associated with a lower risk for age-related macular degeneration (AMD) [13]; vitamin A deficiency is associated with abnormal growth of the skeleton and teeth and infertility in rat [14]; retinal (retinaldehyde) is essential for vision while retinoic acid is essential for skin health, teeth remineralization and bone growth [16]; intakes of lycopene is related to lower risk prostate cancer [17]. Carotenoids are natural colorant with many colors available [18-20]. Carotenoids are precursors for the production of valuable aromatic compounds [21]. β-carotene can be cleaved by P450 cytochrome oxidase to make retinal (retinaldehyde) [16], which is essential for vision and when converted to retinoic acid, it is essential for skin health, teeth remineralization and bone growth. Therefore, carotenoids are valuable food and feed additives, neutraceuticals and cosmoceutical.

Retinol, retinal and retinoic acid are known as retinoids, which are derived from breakdown of skin health, teeth remineralization and bone growth. Retinol and retinal is interconvertable and catalyzed by alcohol dehydrogenase and short-chain dehydrogenase/reductases whereas aldehyde dehydrogenase and cytochrome P450 enzyme families catalyze the irreversible oxidation of retinal to retinoic acid. The identification of enzymes catalyzing retinol oxidation in vivo has been controversial, in part due to the difficulty by the reversible nature of this reaction [22].

*Rhodosporidium* and *Rhodotorula* are two fungal genera belonging to the Pucciniomycotina subphyla. They can be cultured in single-cell form in very high cell density in fermentors at a fast growth rate and accumulate high levels of triacylglyceride [23-26]. *Rhodosporidium* and *Rhodotorula* are able to produce high levels of carotenoid [27-30], with beta-carotene, gamma-carotene, torularhodin and torulene being the major components [31]. Torularhodin and torulene are potential colorants and inducer of gene expression. Apart from the identification of a putative CAR2 homolog [32], there is no report on the carotenoid biosynthetic pathway in *Rhodosporidium* and *Rhodotorula*. Any method that improves the productivity and product purity of carotenoids and their derivatives are of commercial value and significance.

SUMMARY OF THE INVENTION

The present invention relates to the field of fungal biotechnology, more particularly to genetic engineering methods for the production of carotenoids in fungal hosts selected from *Rhodospordium* and *Rhodotorula* genera.

Thus in one aspect, the present invention provides a method for tuning the production level and composition of carotenoids in a fungal host. In accordance with this aspect, the method comprises genetic manipulation of one or more of polynucleotides involved in carotenoid biosynthesis. In one embodiment, the carotenoids are lycopene, beta-carotene, gamma-carotene, torulene, torularhodin or derivatives thereof. In some embodiments, a derivative is a hydroxylated derivative, a glycosylated derivative or an oxidated derivative. In another embodiment, the fungal host is *Rhodospordium* or *Rhodotorula*. In some embodiments, the method comprises genetically manipulating one or more polynucleotides involved in carotenoid biosynthesis in a fungal host and growing the fungal host to produce the carotenoids, whereby the production level or composition of the carotenoids is tuned.

In one embodiment, the genetic manipulation comprises the down-regulation of one or more polynucleotides selected from SEQ ID NOs:1, 3, 5, 7, 8, 9, 10, 11, 13, 14, 16, 17, 19 and 20, or a homolog sharing at least 75% nucleotide identity thereto in a fungal host. In another embodiment, the genetic manipulation comprises the down-regulation of one or more polynucleotides encoding polypeptides selected from SEQ ID NOs:2, 4, 6, 12, 15, 18 and 21 or a homolog sharing at least 75% identity thereto in a fungal host. In some embodiments, the down-regulation is compared to a fungal host without the genetic manipulation. In other embodiments, the one or more polynucleotides are down-regulated by RNAi, artificial transcriptional repressor or a weak promoter.

In one embodiment, the genetic manipulation is the total inactivation of enzyme function in a fungal host. In some embodiments the inactivation is achieved by deletion of all or a part of one or more polynucleotides selected from SEQ ID NOs:10, 11, 16, 17, 19 and 20 or a homolog sharing at least 75% nucleotide identity thereto. In other embodiments the inactivation is achieved by deletion of all or a part of one or more polynucleotides encoding polypeptides selected from SEQ ID NOs:12, 18 and 21 or a homolog sharing at least 75% nucleotide identity thereto. In one embodiment, the deletion is performed by using homologous recombination technique. In another embodiment, the deletion is aided by using an artificial nuclease. In a further embodiment, the artificial nuclease is a Zinc finger Nuclease (ZFN) or Cas9-gRNA complex.

In one embodiment, the genetic manipulation involves over-expression of one or more polynucleotides selected from SEQ ID NOs:1, 3, 5, 7, 8, 9, 10, 11, 13, 14, 16, 17, 19 and 20, or a homolog sharing at least 75% nucleotide identity thereto. In another embodiment, the genetic manipulation involves over-expression of one or more polynucleotides encoding polypeptides selected from SEQ ID NOs:2, 4, 6, 12, 15, 18 and 21; or a homolog sharing at least 75% identity thereto. In some embodiments, the over-expression is mediated by introduction of a synthetic gene cassette into a fungal host cell. In other embodiment, the cassette comprises a heterologous promoter an operably linked to a polynucleotide, optionally operably linked to a transcriptional terminator. In some embodiments, the over-expression is compared to a fungal host without the genetic manipulation.

In some embodiments, the genetic manipulation involves a combination of the previously described genetic manipulations. In one embodiment, the genetic manipulation comprises the down-regulation of one or more of the polynucleotides and over-expression of one or more different polynucleotides. In another embodiment, the genetic manipulation comprises the total inactivation of enzyme function of one or more polypeptides encoded by one or more polynucleotides and the over-expression of one or more different polynucleotides. In a further embodiment, the genetic manipulation comprises the total inactivation of enzyme function of one or more polypeptides encoded by one or more polynucleotides and the down-regulation of one or more different polynucleotides. In an additional embodiment, the genetic manipulation comprises the total inactivation of enzyme function of one or more polypeptides encoded by one or more polynucleotides, the over-expression of one or more of different polynucleotides and the down-regulation of one or more different polynucleotides.

In some embodiments, the polynucleotides described herein that have been stably incorporated in the fungal genome are operatively linked to a promoter which permits efficient expression in species of the Rhodospordium genera and the Rhodotorula genera. The promoters for each incorporated polynucleotide may be the same or different. In some embodiments, the promoters are promoters found in species of the Rhodospordium genera and the Rhodotorula genera. Examples of suitable promoters include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) or transaldolase. In other embodiments, the genes described herein also include a mRNA transcriptional terminator that may be one found in any eukaryotic species and their DNA viruses.

In another embodiment, the present invention provides a method for producing carotenoids which comprises growing a fungal host cell described herein under conditions suitable to produce carotenoids. Any medium with at least 5% carbon source can be used. In some embodiments, the carbon source is glucose, mannose, glycerol, sucrose, xylose or combinations thereof. In one embodiment, the medium is Medium MinCAR containing 30-100 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (per liter). The medium is preferably adjusted to pH 5-7. In some embodiments the cell culturing is preferably performed at 25°-35° C. In other embodiments, the culturing is preferably performed in a condition with lighting.

BRIEF DESCRIPTION OF THE FIGURES

FIG. 2A: Colony color phenotypes of RCM mutants. All strains were streaked on PDA plate and incubated at 28° C. for 2 days. FIG. 2B: Schematic diagram of CAR1 and its deletion strategy. FIG. 2C: Southern blot analysis of candidate CAR1 null mutant (Δcar1). Homologous sequences used for deletion of CAR1 were 1036 bp (CAR1L) and 830 bp (CAR1R) in length, ranging from −89 to +947 and +2098 to +2928 of the translational start codon. Digoxigenin labeled DNA fragment CAR1R was used as the probe for the detection HindIII total DNA. FIG. 2D: Colony colors of WT, null mutant (Δcar1) and complementation strain (Δcar1C) cultured on PDA plate. FIG. 2E: Carotenoid profiles in R. toruloides wild type strain, Δcar1 and Δcar1C. The content of four major carotenoid components were analyzed.

FIGS. 3A-3D show the carotenoid biosynthetic gene cluster in *R. toruloides*. FIG. 3A: Genomic organization of carotenoid biosynthesis gene clusters in 5 carotenogenic fungi, *Blakeslea trispora*, *Fusarium fujikuroi*, *Phycomyces blakesleeanus* and *Sporobolomyces roseus*. FIG. 3B: Deletion of CAR3, CCD1 and CDS1. Upper panel shows the deletion schemes and lower panel shows the Southern blot analysis of knockout mutants. The black bars indicate the probes used for Southern blot hybridization. FIG. 3D: Carotenoid profiles in *R. toruloides* wild type strain and null mutants of CCD1 and CDS1 genes.

FIG. 6A: Schematic structure of ROC1 and gene deletion strategy. FIG. 6B: Phylogenetic tree analysis of negative regulators of fungal carotenoid biosynthesis. NCBI GenBank accession number was followed by the gene name. FIG. 6C: Comparison of RING-finger domains and LON domains. The consensus sequences are indicated in the bottom line of each. GenBank accession numbers (with sequences in FIG. 6C set forth in the indicated sequences): *B. trispora* crgA: CAE51310.1 (SEQ ID NO:26); *M. circinelloides* crgA: CAB61339.2 (SEQ ID NO:28); *A. fumigatus* crgA: XP_755380.1 (SEQ ID NO:25); *F. fujikurol* carS: CCP50075.1 (SEQ ID NO:27); *P. blakesleeanus* carS: ADU04395.1 (SEQ ID NO:29); *U. maydis*: EAK85777.1 (SEQ ID NO:31); *R. toruloides*: (SEQ ID NO:30).

FIG. 7A: Colony color differences between ectopic and homologous recombination of knockout ROC1. FIG. 7B: Southern blot verification of gene deletion mutants. Digoxigenin-labeled DAN Molecular Weight Marker VII (Roche Diagnosis, USA) was used as the marker. FIG. 7C: Cell morphology of roc1 null mutant and wild type. Bar represents 10 µm. FIG. 7D: mRNA transcripts of carotenoid genes in roc1 mutant and wild type strain under illumination condition. FIG. 7E: Comparison of carotenoid production in wild type, knockout mutant strain (Δroc1) and its complementation strain (Δroc1C).

DETAILED DESCRIPTION OF THE INVENTION

Figure 1:
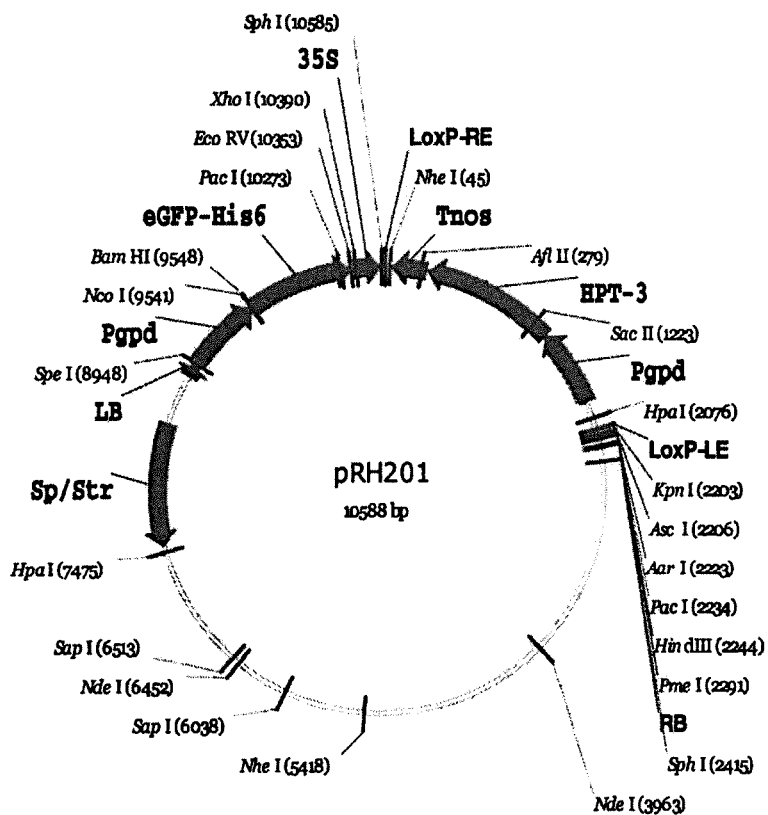
FIG. 1 shows the organization of pRH201. LB: left border of T-DNA; RB: right border of T-DNA; Pgpd: 595 bp promoter of Umgpd1; $P_{GPD1}$: 795 bp promoter of RtGPD1; hpt-3: codon-optimized hygromycin resistance gene based on the codon usage bias in R. toruloides; Tnos: terminator of A. tumefaciens nopaline synthase gene. Unique restriction enzymes cutting sites are shown in red. loxP-RE and loxP-LE and mutant recognition sites for Cre recombinase. Sp/Str are resistance gene for spectinomycin and streptomycin; eGFP-His6 is a R. toruloides codon-adapted gene encoding eGFP-histidine tag fusion protein; 35S: cauliflower mosaic virus 35S gene terminator.

The present invention relates to the field of fungal biotechnology, more particularly to genetic engineering methods for the production of carotenoids in fungal hosts selected from *Rhodospordium* and *Rhodotorula* genera.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

The term "down regulation" refers to diminishment in the level of expression of a polynucleotide, such as a gene, compared to a control using any method known in the art, such as RNAi, an artificial transcriptional repressor to specifically target the gene if interest, such as ZFN and Cas9 that is fused to a transcriptional repressor domain and bind to specific DNA sequence in a gene's promoter or coding sequence to achieve the down-regulation; or use of a weaker promoter to drive the expression of the gene of interest. The term "down regulated" is used herein to indicate that the target gene expression is lowered by 1-100%. For example, the expression may be reduced by about 5%, 10%, 15%, 20%, 25%, 30%, 35%, 40%, 45%, 50%, 55%, 60%, 65%, 70%, 75%, 80%, 85%, 90%, 95%, or 99%.

As used herein, a "comparison window" or "window of comparison" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer to the detailed methods used for sequence alignment, such as in the Wisconsin Genetics Software Package Release 7.0 (Genetics Computer Group, 575 Science Drive Madison, Wis., USA).

A "dsRNA" or "RNAi molecule," as used herein in the context of RNAi, refers to a compound, which is capable of down-regulating or reducing the expression of a gene or the activity of the product of such gene to an extent sufficient to achieve a desired biological or physiological effect. The term "dsRNA" or "RNAi molecule," as used herein, refers to one or more of a dsRNA, siRNA, miRNA, hpRNA, ihpRNA.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

As used herein, "genotype" refers to the genetic constitution of a cell or organism.

The term "homolog" as used herein refers to a gene related to a second gene by descent from a common ancestral DNA sequence. The term, homolog, may apply to the relationship between genes separated by the event of speciation (ortholog) or to the relationship between genes separated by the event of genetic duplication (paralog). The term homolog is used generically to refer to all species.

"Operable linkage" or "operably linked" or "operatively linked" as used herein is understood as meaning, for example, the sequential arrangement of a promoter and the nucleic acid to be expressed and, if appropriate, further regulatory elements such as, for example, a terminator, in such a way that each of the regulatory elements can fulfill its function in the recombinant expression of the nucleic acid to make dsRNA. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another. Regulatory or control sequences may be positioned on the 5' side of the nucleotide sequence or on the 3' side of the nucleotide sequence as is well known in the art.

The term "over-expression" refers to increase in the level of expression of a polynucleotide, such as a gene, compared to a control using any method known in the art, such as an artificial transcriptional activator to specifically target the gene if interest, such as ZFN and Cas9 that is fused to a transcriptional activator domain and bind to specific DNA sequence in a gene's promoter; or use of a stronger promoter to drive the expression of the gene of interest. The term "over-expression" is used herein to indicate that the target gene expression is increased by 25% or more compared to a control. For example, the expression may be increased by about 25%, 50%, 100%, 200%, 500%, 1000% and so on.

As used herein, "phenotype" refers to the detectable characteristics of a cell or organism, which characteristics are the manifestation of gene expression.

The terms "polynucleotide," "nucleic acid" and "nucleic acid molecule" are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analog of a corresponding naturally occurring amino acid, as well as to naturally occurring amino acid polymers Amino acids may be referred to by their commonly known three-letter or one-letter symbols. Amino acid sequences are written left to right in amino to carboxy orientation, respectively. Numeric ranges are inclusive of the numbers defining the range.

As used herein, the term "sequence identity," "sequence similarity" or "homology" is used to describe sequence relationships between two or more nucleotide sequences. The percentage of "sequence identity" between two sequences is determined by comparing two optimally aligned sequences over a comparison window such as the full length of a referenced SEQ ID NO:, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

The term "total inactivation of enzyme function", as used herein, refers to the complete loss of enzyme function or activity for a given enzyme or a given polypeptide having enzyme function or activity compared to a control in which the enzyme has not been inactivated. The enzyme function can be totally inactivated by deleting all or part of a polynucleotide encoding the polypeptide having enzyme function. "Part of a polynucleotide", as used herein with respect to inactivation of enzyme function, refers to a portion of the polynucleotide, the deletion of which is sufficient to cause total inactivation of enzyme function. A part of the polynucleotide could be a single nucleotide or multiple nucleotides as long as the deletion results in premature termination of the polypeptide or a frameshift mutation, each of which would result in an inactive polypeptide. A part of the polynucleotide could be a part that encodes at least 10% but less than 90% of the polypeptide, also resulting in loss of enzyme function.

The term "tuning", as used in one embodiment herein, refers to either increasing or decreasing the yield of a carotenoid by at least 25%, by at least 30%, by at least 35%, by at least 40%, by at least 45%, or by about 50% or more in a genetically manipulated fungal host compared to a non-genetically manipulate control fungal host. The term "tuned", as used in one embodiment herein, refers to either increased or decreased yield of a carotenoid by at least 25%, by at least 30%, by at least 35%, by at least 40%, by at least 45%, or by about 50% or more in a genetically manipulated fungal host compared to a non-genetically manipulate control fungal host.

The term "tuning", as used in another embodiment herein, refers to a change in the composition of carotenoids in a genetically manipulated fungal host compared to a non-genetically manipulated control fungal host. The term "tuned", as used in another embodiment herein, refers to a changed composition of carotenoids in a genetically manipulated fungal host compared to a non-genetically manipulated control fungal host.

Thus in one aspect, the present invention provides a method for tuning the production level and composition of carotenoids in a fungal host. In accordance with this aspect, the method comprises genetic manipulation of one or more of polynucleotides involved in carotenoid biosynthesis. In one embodiment, the carotenoids are lycopene, beta-carotene, gamma-carotene, torulene, torularhodin or derivatives thereof. In some embodiments, a derivative is a hydroxylated derivative, a glycosylated derivative or an oxidated derivative. In another embodiment, the fungal host is *Rho-*

*dospordium* or *Rhodotorula*. In some embodiments, the method comprises genetically manipulating one or more polynucleotides involved in carotenoid biosynthesis in a fungal host and growing the fungal host to produce the carotenoids, whereby the production level or composition of the carotenoids is tuned.

In one embodiment, the genetic manipulation comprises the down-regulation of one or more polynucleotides selected from SEQ ID NOs:1, 3, 5, 7, 8, 9, 10, 11, 13, 14, 16, 17, 19 and 20, or a homolog sharing at least 75%, at least 80%, at least 85%, at least 90%, at least 95%, at least 98% or at least 99% nucleotide identity thereto in a fungal host. In another embodiment, the genetic manipulation comprises the down-regulation of one or more polynucleotides encoding polypeptides selected from SEQ ID NOs:2, 4, 6, 12, 15, 18 and 21, or a homolog sharing at least 75%, at least 80%, at least 85%, at least 90%, at least 95%, at least 98% or at least 99% amino acid identity thereto in a fungal host. In some embodiments, the down-regulation is compared to a fungal host without the genetic manipulated. In other embodiments, the one or more polynucleotides are down-regulated by RNAi, artificial transcriptional repressor or a weak promoter.

Down-regulation of a polynucleotide of the present invention can be brought about by using well known techniques, including, but not limited to, RNAi techniques, such as dsRNA, miRNA, siRNA, smRNA, hpRNA or ihpRNA (collectively referred to as RNAi molecules), sense suppression (co-suppression), antisense, and the like. Such techniques are described in U.S. Pat. No. 7,312,323 and references cited therein. For example, reduction might be accomplished, for example, with transformation of a fungal host cell to comprise a promoter and other 5' and/or 3' regulatory regions described herein linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. RNAi molecules or microRNA molecules (referred to collectively herein as RNAi molecules) can be prepared by the skilled artisan using techniques well known in the art, including techniques for the selection and testing of RNAi molecules and microRNA molecules that are useful for down regulating a polynucleotide of the present invention. See, for example, Wesley et al. (2001), Mysara et al. (2011) and Yan et al. (2012).

It has typically been found that dsRNA of 200-700 bp are particularly suited for inducing RNAi in plants. It has also been found that hairpin RNAs containing an intron, for example, a construct comprising an RNA encoding sequence in a sense direction operably linked to an intron operably linked to an RNA encoding sequence in an antisense direction or vice versa which is capable of forming an intron-hairpin RNA (ihpRNA), is suitable for inducing RNAi in plants. See, for example, Wang et al. (2000), Fuentes et al. (2006), Bonfim et al. (2007) Vanderschuren et al. (2007a, 2007b), Zrachya et al. (2007). For example, a nucleic acid construct can be prepared that includes a nucleic acid that is transcribed into an RNA that can anneal to itself, e.g., a double stranded RNA having a stem-loop structure. In addition, hairpin structures can be prepared as described by Guo et al. (2003).

For example, a nucleic acid construct can be prepared that includes a nucleic that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence, or a fragment thereof, of a polynucleotide as described herein, and that is from about 10 nucleotides to about 1,800 nucleotides in length. The length of the sequence that is similar or identical to the sense coding sequence can be from 10 nucleotides to 1000 nucleotides, from 15 nucleotides to 600 nucleotides, from 20 nucleotides to 500 nucleotides, or from 25 nucleotides to 100 nucleotides, or any length within the 10 nucleotides to 2,500 nucleotides. The other strand of the stem portion of a double stranded RNA comprises a sequence that is similar or identical to the antisense strand, or a fragment thereof, of the coding sequence of the polypeptide of interest, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of the mRNA encoding a polypeptide described herin, and the other strand of the stem portion of the double stranded RNA comprises a sequence that is similar or identical to the sequence that is complementary to the 3' or 5' untranslated region, respectively, or a fragment thereof, of the mRNA encoding a polypeptide described herein. In other embodiments, one strand of the stem portion of a double stranded RNA comprises a sequence that is similar or identical to the sequence of an intron or a fragment thereof in the pre-mRNA transcribed from a polynucleotide described herein, and the other strand of the stem portion comprises a sequence that is similar or identical to the sequence that is complementary to the sequence of the intron or fragment thereof in the pre-mRNA.

The loop portion of a double stranded RNA can be from 3 nucleotides to 5,000 nucleotides, e.g., from 3 nucleotides to 2500 nucleotides, from 15 nucleotides to 1,000 nucleotides, from 20 nucleotides to 500 nucleotides, or from 25 nucleotides to 200 nucleotides, or any length within the 3 nucleotides to 5,000 nucleotides. The loop portion of the RNA can include an intron or a fragment thereof. A double stranded RNA can have zero, one, two, three, four, five, six, seven, eight, nine, ten, or more stem-loop structures.

In one embodiment, the genetic manipulation is the total inactivation of enzyme function in a fungal host. In some embodiments the inactivation is achieved by deletion of all or a part of one or more polynucleotides selected from SEQ ID NOs:10, 11, 16, 17, 19 and 20, or a homolog sharing at least 75%, at least 80%, at least 85%, at least 90%, at least 95%, at least 98% or at least 99% nucleotide identity thereto. In other embodiments the inactivation is achieved by deletion of all or a part of one or more polynucleotides encoding polypeptides selected from SEQ ID NOs:12, 18 and 21 or a homolog sharing at least 75%, at least 80%, at least 85%, at least 90%, at least 95%, at least 98% or at least 99% amino acid identity thereto. In one embodiment, the deletion is performed by using homologous recombination techniques. Homologous recombination techniques are well known to the skilled artisan. In another embodiment, the deletion is aided by using an artificial nuclease. In a further embodiment, the artificial nuclease is a Zinc finger Nuclease (ZFN) or Cas9-gRNA complex. Artificial nuclease technologies are well known to the skilled artisan. See, for example, Durai et al. (2005), Makarova et al. (2011) and Mali et al. (2013).

In one embodiment, the genetic manipulation involves over-expression of one or more polynucleotides selected from SEQ ID NOs:1, 3, 5, 7, 8, 9, 10, 11, 13, 14, 16, 17, 19 and 20, or a homolog sharing at least 75%, at least 80%, at least 85%, at least 90%, at least 95%, at least 98% or at least 99% nucleotide identity thereto. In another embodiment, the genetic manipulation involves over-expression of one or more polynucleotides encoding polypeptides selected from SEQ ID NOs:2, 4, 6, 12, 15, 18 and 21, or a homolog sharing at least 75%, at least 80%, at least 85%, at least 90%, at least 95%, at least 98% or at least 99% amino acid identity thereto. In some embodiments, the over-expression is mediated by introduction of a synthetic gene cassette into a fungal host cell. In other embodiment, the cassette comprises a heterologous promoter operably linked to the polynucleotide, optionally operably linked to a transcriptional terminator. In some embodiments, the over-expression is compared to a fungal host without the genetic manipulated.

In some embodiments, the genetic manipulation involves a combination of the previously described genetic manipulations. In one embodiment, the genetic manipulation comprises the down-regulation of one or more of the polynucleotides and over-expression of one or more different polynucleotides. In another embodiment, the genetic manipulation comprises the total inactivation of enzyme function of one or more polypeptides encoded by one or more polynucleotides and the over-expression of one or more different polynucleotides. In a further embodiment, the genetic manipulation comprises the total inactivation of enzyme function of one or more polypeptides encoded by one or more polynucleotides and the down-regulation of one or more different polynucleotides. In an additional embodiment, the genetic manipulation comprises the total inactivation of enzyme function of one or more polypeptides encoded by one or more polynucleotides, the over-expression of one or more different polynucleotides and the down-regulation of one or more different polynucleotides.

Table 1 shows representative examples genetic manipulation in fungal hosts of the present invention and the effect with respect to tuning carotenoid production or composition.

TABLE 1

Examples of Tuning Carotenoid Production or Composition

| SEQ ID NO: (Gene Name) | Genetic Manipulation | Tuning Effect |
|---|---|---|
| 1 (CAR1) | down-regulation | decreased level of carotenoid |
| 3 (CAR2) | over-expression | increased level of carotenoid |
| 1 (CAR1) | over-expression | increased level of total carotenoid |
| 19 (ROC1) | down-regulation | |
| 10 (CCD1) | deletion | increased level of torularhodin and/or its derivatives |
| 17 (ALD1) | over-expression | increased levels if total carotenoid, torulene and torularhodin |

In some embodiments, the polynucleotides described herein have been stably incorporated in the fungal genome. In these embodiments, the polynucleotides are operatively linked to a promoter which permits efficient expression in species of the Rhodospordium genera and the Rhodotorula genera. The promoters for each incorporated polynucleotide may be the same or different. In some embodiments, the promoters are promoters found in species of the Rhodospordium genera and the Rhodotorula genera. In other embodiments, the promoters are promotes found in other fungal species. Examples of suitable promoters include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) or transaldolase. In other embodiments, the genes described herein also include a mRNA transcriptional terminator that may be one found in any eukaryotic species and their DNA viruses.

In some embodiments, a suitable promoter is one described in International Patent Application Publication No. WO 2012/169969, incorporated by reference herein in its entirety. This published application describes several polynucleotide sequences derived from the upstream region of glyceraldehyde phosphate dehydrogenase gene (GPD1), translation initiation factor gene (TEF1), and stearoyl-CoA-delta 9-desaturase gene (FAD1) that function as promoters in fungi. The promoters described in this published application are set forth in SEQ ID NOs:94-101. In other embodiments, additional promoters are described in International Patent Application Publication No. WO 2014/142747, incorporated by reference herein in its entirety. The promoters described in this published application are set forth in SEQ ID NOs:102-118.

In addition, operable fragments of the promoter sequences described herein can be isolated using convention promoter screening assays and can be screened for efficient selection of transformed fungal cells using the techniques described herein. In one embodiment, an operable fragment, also termed a promoter portion herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs.

In one embodiment, a promoter sequence is provided which has at least 60% identity with any one of these promoter sequences. In another embodiment, a promoter sequence is provided which has at least 70% identity with any one of these promoter sequences. In an additional embodiment, a promoter sequence is provided which has at least 80% identity with any one of these promoter sequences. In a further embodiment, a promoter sequence is provided which has at least 90% identity with any one of these promoter sequences. In another embodiment, a promoter sequence is provided which has at least 95% identity with any one of these promoter sequences. In another embodiment, a promoter sequence is provided which has at least 98% identity with any one of these promoter sequences.

The genes to be stably incorporated into the fungal genome are typically in the form of a DNA or polynucleotide construct comprising the promoter sequences described herein, an operably linked polypeptide encoding sequence described herein and an operably linked RNA transcriptional terminator sequence. In one embodiment, any transcriptional terminator operable in species of the fungi can be used. Terminators are typically located downstream (3') of the gene, after the stop codon (TGA, TAG or TAA). Terminators play an important role in the processing and stability of RNA as well as in translation.

A DNA or nucleic acid construct that comprises a fungi operable promoter, protein encoding DNA sequence and a fungi operable terminator may also be referred to herein as an expression cassette. The expression cassette may include other transcriptional regulatory regions as are well known in the art. In other embodiments, the DNA or nucleic acid construct or expression cassette further comprises a selectable marker. Selectable markers are well known to the skilled artisan as are expression cassettes incorporating such selectable markers and promoters to drive their expression, such as described in International Patent Application Publication No. WO 2012/169969. Any suitable promoter operably linked to any suitable selectable marker can be used in the present invention. In some embodiments, one or more DNA molecules may be used in which each DNA molecule has one or more nucleic acid constructs.

In another embodiment, the present invention provides a method for producing carotenoids which comprises growing a fungal host cell described herein under conditions suitable to produce carotenoids. Any medium with at least 5% carbon source can be used. In some embodiments, the carbon source is glucose, mannose, glycerol, sucrose, xylose or combinations thereof. In one embodiment, the medium is Medium MinCAR containing 30-100 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (per liter). The medium is preferably adjusted to pH 5-7. In some embodiments the cell culturing is preferably performed at 25°-35° C. In other embodiments, the culturing is preferably performed in a condition with lighting.

In preparing the nucleic acid construct or an expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

It may be useful to generate a number of individual transformed fungi with any recombinant construct in order to recover fungi free from any positional effects. It may also be preferable to select fungi that contain more than one copy of the introduced polynucleotide construct such that high levels of expression of the recombinant molecule are obtained.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes,* (Academic Press, New York, 1992); Guthrie and Fink, *Guide to Yeast Genetics and Molecular Biology* (Academic Press, New York, 1991); Harlow and Lane, 1988, *Antibodies,* (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); Riott, *Essential Immunology,* 6th Edition, Blackwell Scientific Publications, Oxford, 1988; Fire et al., *RNA Interference Technology: From Basic Science to Drug Development,* Cambridge University Press, Cambridge, 2005; Schepers, *RNA Interference in Practice,* Wiley-VCH, 2005; Engelke, *RNA Interference (RNAi): The Nuts & Bolts of siRNA Technology,* DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application,* CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Strains, Chemicals, Media and Culture Conditions

*Rhodosporidium. toruloides* strain ATCC 10657, ATCC 10788, ATCC 204091 (previous known as *Rhodotorula glutinis*), *Rhodotorula glutinis* strain ATCC 90781 were purchased from ATCC (USA). *Rhodotorula glutinis graminis* strain WP1 and *Sporobolomyces roseus* FGSC 10293 (IAM13481) was obtained from Fungal Genetics Stock Center (University of Missouri, USA). *A. tumefaciens* strain AGL1 [33] and AGL2 [34] were used for ATMT.

*Rhodosporidium* strains were cultured at 28°-30° C. in YPD broth (1% yeast extract, 2% peptone, 2% glucose) or on solid potato-dextrose agar (PDA). *A. tumefaciens* was grown at 28° C. in either liquid or solid 2YT medium (1.6% tryptone, 1% yeast extract, 0.5% NaCl). *Escherichia coli* XL1-Blue was cultured in Luria-Bertani (LB) broth or on LB agar and used for routine DNA manipulation. To accumulate carotenoid and lipid production, *R. toruloides* was cultured in carotenoid producing medium (MinCAR) and lipid accumulation medium (MinRL2), respectively. MinCAR and MinRL2 was modified from the carotenoid medium [35] and lipid medium [36]. Medium MinCAR contains (per liter) 70 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (pH 6.1). Medium MinRL2 contains (per liter) 100 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (pH 6.1).

Example 2

Isolation of Genomic DNA and Total RNA

Genomic DNA and RNA of *R. toruloides* were extracted as described previously [37]. The extracted DNA was qualified by agarose gel electrophoresis and quantified with a NanoDrop® ND-1000 Spectrophotometer (Nanodrop Technologies, USA).

Example 3

*Agrobacterium Tumefaciens*-Mediated Transformation (ATMT)

Fungi transformation via ATMT was performed as described previously unless indicated otherwise [37]. The binary vectors were transformed by electroporation into *A. tumefaciens* AGL1 or AGL2 using a 0.2 mM cuvette coupled with a BioRad eletroporator set at 2.5 kV, 25 µF, 400Ω. Transformants were selected on 2YT agar plates supplemented with streptomycin (100 µg/ml).

Example 4

DNA Constructs

Oligonucleotides used are listed in Table 2. All restriction and modification enzymes were purchased from New England Biolabs (NEB, Massachusetts, USA).

TABLE 2

Sequences of Oligonucleotides

| Name | Sequence (5'-3') (SEQ ID NO:) | Restriction Site | Description |
| --- | --- | --- | --- |
| PgpdR2-Sf | TTTactagtGGACGGCTTGTTCTCTCCTG (32) | SpeI | *U. maydis* gpd1 promoter |
| Rt012N | TTTccatggTGAGTGATCTGGTGTTGTTC (33) | NcoI | |
| PgpdR2-Sf | TTTactagtGGACGGCTTGTTCTCTCCTG (34) | | RtGPD1 promoter |
| Rt012N | TTTccatggTGAGTGATCTGGTGTTGTTC (35) | | |
| Rt127-2 | GGAACTCATCCGCTCGATCG (36) | | Deletion of CAR1 |
| Rt128-2 | CAGGCCTTCGCCATCGGATT (37) | | |
| Rt129 | TCCTCTTCCGACTGGGACAA (38) | | Colony PCR for Δcar1 |
| Rt130 | CCCAAACAACACCGAGAGGA (39) | | |
| CAR3Lf | AAACACTGATAGTTTTTGGAAGGGTGACGCACCTC (40) | | Deletion of CAR3 |
| CAR3Rr2 | TCGAGCTCGGTACCCAGGAGGAGAAGAAGGTGATGG (41) | | |
| Rt138 | TCGCTGGATTGGTACGACAAC (42) | | Colony PCR for Δcar3 |
| Rt139 | CCACCAGTGACCATCTCTTCG (43) | | |
| CCD1L-Kf | AAAggtaccGACTTGTCCGAGCGAGAGAC (44) | KpnI | Deletion of CCD1 |
| CCD1L-Hr | AAAaagcttAGACTCCAGAACCCGACCGTA (45) | HindIII | |
| CCD1R-Bf | TTTggatccCGAGTCTCAATCCCTCCCA (46) | BamHI | |
| CCD1R-Str | TTTaggcctGGAGGACGGGCGATACAACTC (47) | StuI | |
| CCD1f | GTCTTTCGCGCCCTCTTCCTC (48) | | Colony PCR for Δccd1 |
| CCD1r | CGTAGGAGATGACGGGCTTGC (49) | | |
| CDS1L-Stf | TTTaggcctCTCGCTCTCCTGCACACTTCG (50) | StuI | Deletion of CDS1 |
| CDS1L-Hr | TTTaagcttCGCATTTCCAGTCCCATCGC (51) | HindIII | |
| CDS1R-Bf | TTTggatccACCCTCTACGTCCCCTTCACC (52) | BamHI | |
| CDS1R-Sr | TTTgagctcAACGCCTCGATCCTGACTTGC (53) | SacI | |
| CDS1f | GTCCTGCTCGCAACCCTCAC (54) | | Colony PCR for Δcds1 |
| CDS1r2 | GAGACGAAGGATGGAGTGGCG (55) | | |
| ALD1Lf | CACCCGTCCTCTCCGCTTC (56) | | Deletion of ALD1 |
| ALD1Rr | CCTCGCTCTTTCGCTGGTTC (57) | | |
| Rt134 | CAGCCACATTCGTTCTTCAGG (58) | | Colony PCR Δald1 |
| Rt135 | TGGATGATGCGGATATTGAGG (59) | | |
| Rt203Nf | TTTccatggAGGACACTCCCATCGACAGC (60) | NcoI | Expression of ALD1 |
| Rt204Br | TTTggatccCCTGTCCCGTCAACTTCTGC (61) | BamHI | |

TABLE 2-continued

Sequences of Oligonucleotides

| Name | Sequence (5'-3') (SEQ ID NO:) | Restriction Site | Description |
|---|---|---|---|
| CARSL-Stf | TTTaggcctCAGCCAAGTTCAAGCACAACC (62) | StuI | Deletion of ROC1 |
| CARSL-Hr | TTTaagatCGACCGATCTCGAGGAGACAT (63) | HindIII | |
| CARSR-Bf | AAAggatccGGAACGATACCCTCCAAGACG (64) | BamHI | |
| CARSR-Sr | AAAgagctcTGGGAGTTGCGAGGTCATAGA (65) | SacI | |
| CARSf | TTGTTCTCGGATGTGCGATTGG (66) | | Colony PCR for |
| CARSr | ATAATCTTGGTGAGCGCGATGTT (67) | | Δroc1 |
| Rt301Nf | TTTccatggCGACTCTAGCCATCAGACC (68) | NcoI | Expression of |
| Rt302Evr | TTTgatatcGAGGCTAGGCGATGTTGCAG (69) | EcoRV | ROC1 |
| Rt303Sf | TTTactagtCAAGATCTACGAGGCGAC (70) | SpeI | Complementation |
| Rt304Pmr | TTTgtttaaacGAGTGCCCAACGACTTTCTAC (71) | PmeI | of ROC1 |
| Rt140 | CGCTGACCTTCCCAATCTTTC (72) | | DIG-probe for |
| Rt141 | CTTTCCGACCGACTTCTTGCT (73) | | CAR1 |
| Rt146 | GAACCGCAGGTGAAGGTCAAT (74) | | DIG-probe for |
| Rt147 | TATCGGCAAGGTACGTCTCTTC (75) | | CAR3 |
| Rt148 | CAGGTTTCATCGCAACTACATTGA (76) | | DIG-probe of |
| Rt149 | AACAGAGCGAGTTGAAGAGTAGCC (77) | | ALD1 |
| qCAR3f | GCGACGACTACGTGAACCTG 78) | | qPCR of CAR1 |
| qCAR3r | CGATGGGGAAGGAGAATTTG (79) | | |
| qCAR2f | GCACACTGCACGCCTTACTC (80) | | qPCR of CAR2 |
| qCAR2r | ACGAGCTGAAGAGCCTGTCC (81) | | |
| qCAR1f | GCAAGATACCCCAGCTCGAC (82) | | qPCR of CAR1 |
| qCAR1r | GGGGACGTTGACGTAGAAGG (83) | | |
| qCCD1f | GGCTGGATGAAGGAGTGGAC (84) | | qPCR of CCD1 |
| qCCD1r | AGGAGGAGCGTGAGTGGAAG (85) | | |
| qCDS1f | ATGGGACTGGAAATGCGAAC (86) | | qPCR of CDS1 |
| qCDS1r | GGGAGACGAAGGATGGAGTG (87) | | |
| qALD1f | TCGTGCACAACCCGAACTAC (88) | | qPCR of ALD1 |
| qALD1r | ATCTTGCGCTCCTTCTCGTC (89) | | |
| qROC1f | ACCAGCTTCAGACCACGTCTC (90) | | qPCR of ROC1 |
| qROC1r | AGAAGTTGGAGGAAGGGATGG (91) | | |
| qACT1f | CGACAACTTTGACGACCCTTC (92) | | qPCR of ACT1 |
| qACT1r | CAGGTTGGGACAAGTTGGGTA (93) | | |

Various promoters, such as promoter of *U. maydis* gpd1 (Pgpd, 595 bp in length) [38, 39] and RtGPD1 (795 bp) [37], have been described previously and was amplified using the template of plasmid pEX1 [42] and genomic DNA of *R. toruloides* ATCC 10657, using primer pairs Pgpd-Sf/Pgpd-Nr and Rt011S/Rt012N, respectively. The resultant PCR products were digested with SpeI and NcoI and cloned by 3-fragment ligation with the 1030-bp BspHI/SmaI DNA fragment of synthetic hpt-3 gene [37] and the 8855-bp SpeI/SacI (blunt-ended) DNA fragment of pEC3GPD-GUS, creating pEC3GPD-HPT3 and pEC3GPDR-HPT3, respectively.

To create deletion constructs for CAR1, CAR3 and ALD1, the DNA fragment covering complete coding regions of the gene (3.0 kb, 2.8 kb and 3.0 kb, respectively) was amplified using genomic DNA of *R. toruloides* ATCC 10657 as the template and oligo pair Rt127-2/Rt128-2, CAR3Lf/CAR3Rr2 and ALD1Lf/ALD1Rr as primer pairs, respectively. The blunt-ended PCR product was ligated to PmeI/SacI (blunt-ended) pEX2 vector to create the intermediate vector pEX2CAR1, pEX2CAR3 and pEX2ALD1, respectively. Subsequently, the hygromycin resistance cassette (Rt$_{GPD1}$::hpt-3::Tnos with the 795 bp version of RtGPD1 promoter driving the expression of hpt-3) amplified from plasmid pRH2034 was ligated to the SmaI/MfeI-cut pEX2CAR1, PvuII/BglII-cut pEX2CAR3, and XhoI/BspHI-cut pEX2ALD1 (blunt ended) to create gene targeting plasmid, pKOCAR1, pKOCAR3 and pKOALD1, respectively.

For deletion of CCD1, the right and left arm (0.9 kb each) for homologous recombination was amplified using genomic DNA of *R. toruloides* ATCC 10657 as the template and specific oligo pair CCD1L-Kf/CCD1L-Hr and CCD1R-Bf/CCD1R-Str, respectively. Gene deletion plasmid pKOCCD1 was created by four-fragment ligation consisting of KpnI/HindIII-digested right arm, BamHI/StuI-digested left arm, HindIII/BamHI hygromycin resistance cassette from pDXP795hptR [32] and KpnI/SacI-digested pEX2 vector. Recombinant *E. coli* strains with the correct fragments were identified by colony PCR followed by DNA sequencing of the entire recombination cassette. A similar strategy was applied for the deletion of CDS1. Oligo pairs CDS1L-Stf/CDS1L-Hr and CDS1R-Bf/CDS1R-Sr was used to amplify the right and left homolgy arms of CDS1 (0.5 kb each), respectively. The DNA fragments were digested using StuI/HindIII for the left arm and BamHI/SacI for the right arm, which were ligated with the HindIII/BamHI hygromycin resistance cassette and SmaI/SacI-digested pEX2 vector.

For in vitro expression of ALD1, cDNA sequences were amplified by RT-PCR with the template of total RNA and oligos Rt203Nf and Rt204Br. The NcoI-BamHI double digested PCR products were cloned in pRH2034 vector at the same sites to create the plasmid pRHALD1, in which a fusion Ald1-eGFP was driven by the RtGPD1 promoter.

For deletion of ROC1, oligo pairs CARSL-Stf/CARSL-Hr and CARSR-Bf/CARSR-Sr were used to amplify the 5' and 3' homologous flanking fragments (0.9 kb each). A four-fragment ligation was performed with SacI-PmeI pEX2 binary vector, StuI-HindIII 5' flanks, codon-optimized hygromycin resistant cassette from pDXP795hptR ($P_{GPD1}$::hpt-3::$T_{nos}$) and BamHI-SacI 3' flanks to generate gene deletion plasmid pKOROC1, where $P_{GPD1}$ is the glyceraldehyde 3-phosphate promoter of R. toruloides ATCC 10657 with GenBank accession number of JN208861, hpt-3 is the codon-optimized gene encoding hygromycin phosphotransferase (JQ806387), and Tnos is the terminator of agrobacterium (Liu, Koh et al. 2013).

For complementation studies of Δcar1, the CAR1 genome locus ranging from 389556 to 393649 nt of WGS scaffold#18 was amplified using the template of R. toruloides and oligos Rt127-2 and CDSL1. The 4.1 kb PCR products were blunt-ended and ligated with SpeI (blunt end)-PmeI-linearized pRH2034 vector to create the complementation plasmid pRHCAR1. For complementation studies of Δroc1, the ROC1 genome locus ranging from 622910 to 627480 nt of WGS scaffold#9 was amplified using the template of R. toruloides and oligos Rt303Sf and Rt304Pmr. The 4.6 kb PCR products were double digested by SpeI and PmeI, and ligated with SpeI-PmeI-linearized pRH2034 vector to create the complementation plasmid pRHROC1.

Example 5

Colony PCR and Southern Blot Analysis

Fungal colony PCR analysis was used for screening of candidate gene deletion mutants. Briefly, single colonies of transformants were cultured in 150 μl YPD broth supplemented with cefotaxime (300 mg/ml) and hygromycin (150 mg/ml) for several hours. One microliter of cell culture were used for colony PCR analysis with appropriate oligo pair within the gene targeting region (Table 2). PCR was conducted using i-Taq polymerase (i-DNA Biotech, Singapore) and the following program: initiation at 95° C. for 5 min, followed with 35 cycles of 94° C. for 30 s, 58° C. for 30 s and 72° C. for 45 s, and further extension at 72° C. for 5 min. Electrophoresis was used for identification of candidate mutants lacking of DNA fragments that could be amplified using the template of genomic DNA from WT.

To verify the true gene deletion mutants without any ectopic integration, genomic DNAs were digested with HindIII, PstI, PvuI, PvuI, HincII and PvuI for the putative knockout mutants Δcar1, Δcar3, Δccd1, Δcds1, Δald1 and Δand, respectively. DNA fragments containing the right arms of CAR1, CAR3, ALD1, ROC1 and the left arms of CCD1, CDS1 were labeled with digoxigenin using DIG-High prime DNA labeling and detection starter Kit II (Roche Diagnostics, USA). Southern blot hybridization was performed according to the manufacturer's instructions.

Example 6

Quantitative Reverse Transcription PCR

Total RNA was extracted as described previously [37]. Before quantitative reverse transcription PCR (qRT-PCR), total RNA was treated with DNase I (Roche Diagnostics) to remove trace DNA and recovered by precipitation with ethanol. cDNA was synthesized using the iScript™ Reverse Transcription Supermix (Bio-Rad, USA) and q-PCR was conducted in ABI PRISM 7900HT Sequence Detection System using the ABI SYBR® Select Master Mix (Life Technologies, USA). qRT-PCR conditions were as followed: an initial 50° C. for 2 min and 95° C. denaturation step for 10 min followed by 40 cycles of denaturation at 95° C. for 15 s, annealing at 60° C. for 1 min. Samples were analyzed in triplicates and data was acquired using the SDS 2.4 software (Life Technologies, USA). Relative gene expression levels were calculated against the reference gene ACT1 (SEQ ID NOs:22, 23, 24 for genomic, cDNA and protein, respectively) using the 2-ΔΔCt method with the RQ Manager software v1.2.1 (Applied Biosystems, USA).

Example 7

Screening of Genes Involved in Carotenoid Biosynthesis

R. toruloides haploid strain ATCC 10657 was mutagenized by random insertions of T-DNA by Agrobacterium tumefaciens-mediated transformation of binary T-DNA vector pRH201 (FIG. 1). Transformants were selected on YPD agar medium supplemented with 300 μg/ml cefotaxime and 150 μg/ml hygromycin. After incubated at 28° C. for 5 days, transformants showing albino or pale colors were transferred to liquid YPD medium (300 μg/ml cefotaxime, 150 μg/ml hygromycin) for propagation. After streaking on PDA plates supplemented with above antibiotics, single colonies showing stable color phenotype were named as Rhodosporidium Carotenoid Mutant (RCM).

Example 8

Identification of T-DNA Tagging Positions

T-DNA tag positions in the genome was identified by High Efficient Thermal Asymmetric InterLaced PCR (hi-TAIL-PCR) [43, 44]. Specific primers (HRSP1, HRSP2 and HRSP3) and arbitrary primer LAD1-4 were used for T-DNA left border (LB) flanking sequences whereas specific primers (HRRSP1, HRRSP2 and HRRSP3) and arbitrary primer LAD1-4 for the right border (RB) flanking sequences. PCR reactions were carried out with i-Taq DNA polymerase (i-DNA, Singapore) in a PTC-200™ Programmable Thermal Controller (Bio-Rad, USA). PCR products were purified using gel extraction kit (Qiagen, USA) and sequenced directly using BigDye terminator kit (Applied Biosystems, USA) with oligo HRRSP3 (for RB-flanking sequences) or HRSP3 (LB-flanking sequences). For samples that gave poor sequencing results, PCR products were cloned in pGTM-T easy vector (Promega, USA) and sequenced using oligos M13FP and M13RP.

Example 9

Extraction of Carotenoids

Cells were cultured in 50 ml MinCAR medium in shaking flasks at 30° C. and pelleted by centrifugation. After washing twice with water, wet cell mass were determined by weighing and mixed with equal mass of acid-washed glass beads (0.4-0.6 mm in diameter, Sigma-Aldirch) and 5 ml DMSO. Cells were lysed by vigorous vortex mixing for 10 min, 1 h incubation at 65° C. followed by freezing at −20° C. After thawing, the suspension was centrifuged at 10,000 g, and the supernatant containing DMSO-soluble carotenoids was transferred to a new tube while the insoluble cell residue was re-extracted with 30 ml of light petroleum ether-ethyl acetate (36:19) for 10 min at room temperature. The contents of the two extractions were combined and extracted with 2 ml saturated NaCl. The solvent phase was collected after centrifugation and dried under a nitrogen gas flow. The samples were re-dissolved in hexane and stored in −20° C. before further analysis.

Example 10

Quantification Methods

Cell biomass (dry cell weight) was determined by lyophilizing the cell pellet collected by centrifugation until a constant weight was reached.

Glucose concentration in media was quantified by HPLC. Medium was separated from cells by centrifugation and filtered through a 0.2 μm nylon membrane. 10 μl of the sample was injected and run through a 300×7.0 mm Aminex 87H column (Bio-Rad) at a constant flow rate of 0.7 mL/min using 5 mM sulfuric acid as the mobile phase. The column was maintained at 50° C., and glucose was detected with a Refractive Index Dector (FID, Shimadzu, Japan). Concentration of glucose in the cell culture was determined using a calibration curve built with the standard glucose aqueous solution.

The major peaks were determined by the absorption spectra in hexane and mass spectrometry. Atmospheric pressure chemical ionization (APCI) technique is as described previously [46, 47] with some modifications. Briefly, samples (x μl) was run in a Shimadzu UPLC-MS (APCI) system (Shimadzu, Japan) equipped with a YMC-carotenoid column (C30 reverse phase, Φ3 μm, 150 mm×3.0 mm I.D., YMC, Japan) at a flow rate of 0.3 ml/mL in a linear gradient within 3 min, from 100% mixture A (MeOH/tert-butylmethyether/water, 30:1:10, v/v/v) to 50% mixture B (MeOH/tert-butylmethyether, 1:1, v/v) followed with 100% mixture B for 0.5 min and then the colume was maintained under the conditions for 15 min at a flow rate of 0.6 ml/min. APCI in positive mode was used for the identification of carotenoid components with 15 L/s of nitrogen gas as sheath and auxiliary gas. The vaporizer and capillary temperature was set at 350° C. and 150° C., respectively, and the capillary and tube lens voltages was set at 50 V and 125 V, respectively.

Example 11

Characterization of Carotenoid Biosynthetic Mutants

Screening of about 20,000 T-DNA transformants by visual identification of colony colors lead to the identification of six carotenoid mutants, which are named RAM1-5 (R. toruloides Carotenoid Mutants) (FIGS. 2a-2E, Table 3). HiTAIL PCR and BLAST search of the sequence tags revealed that T-DNAs were inserted into genes encoding a putative riboflavin transporter, aldehyde hydrogenase, hexose transporter, TATA-binding protein associated factor, phytoene desaturase and fatty aldehyde dehydrogenase respectively (Table 3). The role of phytoene desaturase, or Car1 in fungi (EC 1.3.99.30) in lycopene production is well known [48].

TABLE 3

Characterization of R. toruloides Albino Mutants (RAM)

| Sequence number[a] | Genic site[b,c] | Best hit[d] | Annotation[e] | Organism[f] | Identity[g] |
|---|---|---|---|---|---|
| RB sequences | | | | | |
| RAM1 | Genic sequence | XP_003032296 | Riboflavin transporter MCH5 | Schizophyllum commune | 52% |
| RAM2 | Upstream-0.5 kb | YP_001220603 | resolvase | Aeromonas bestiarum | 95% |
| RAM3 | Genic sequence | XP_571856 | hexose transport-related protein | Cryptococcus neoformans | 36% |
| RAM4 | Genic sequence | XP_758766 | TATA-binding protein (TBP) associated factor Taf2 (MTCC 457 contig458_1:18376-18377+) | Ustilago maydis | 35% |
| RAM5 | Genic sequence | KF601426.1 | phytoene synthase | Rhodosporidium diobovatum | 98% |

[a]Flanking sequence obtained from corresponding to number of T-DNA transformant
[b]T-DNA tagged genes were determined according to the BLASTx results
[c]Upstream 1.0 kb, Upstream 0.5 kb and downstream 0.3 kb denotes T-DNA insertions within upstream 501~1000 bp, 500 bp and downstream 300 bp of the corresponding tagged gene, respectively
[d]Best hit denotes the BLASTx result with the highest E-score
[e]Annotations were determined according to the BLASTx results
[f]Microorganism denotes the host of Best hit
[g]Identity values were from BLASTx results
[h] Not available due to the bad sequencing result

Example 12

Figure 2:
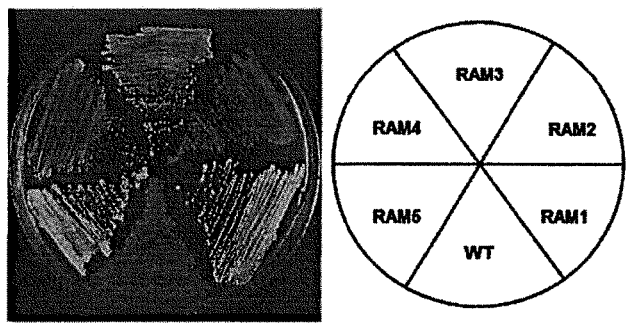
FIGS. 2A-2E show the identification of RCM mutants and characterization of CAR1 gene.
Figure 2:
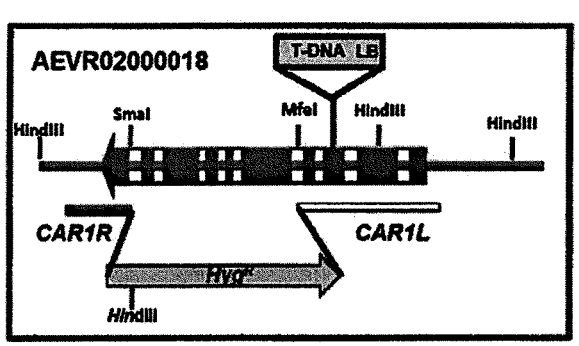
Figure 2:
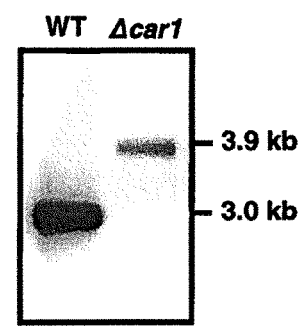
Figure 2:
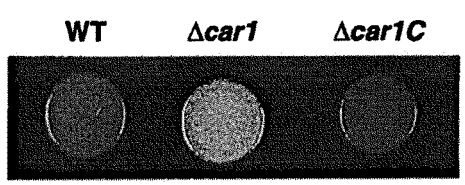
Figure 2:
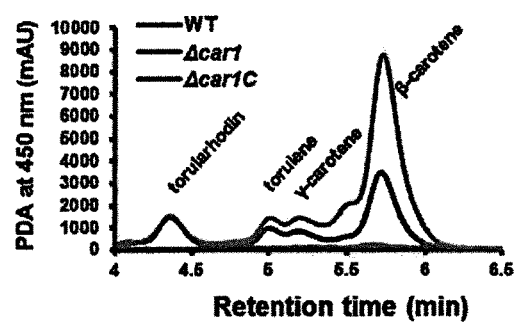

Analysis of Carotenoid Biosynthesis Gene Cluster in R. toruloides by Reverse Genetics HiTAIL PCR revealed that the RCM5 albino phenotype resulted from a T-DNA inserted between 391802 nt and 391803 nt in genome scaffold #18 (AEVR02000018) of R. glutenis ATCC 204091, located in the 3$^{rd}$ exon of the putative phytoene desaturase gene (CAR1, genome locus RTG_00274) (FIG. 2B), an enzyme involved in carotenoid biosynthesis. To confirm the function of this gene that was interrupted by the T-DNA insertion, the putative CAR1 CDS was deleted by targeted knockout using ATMT of pKO-CAR1, in which the nucleotide sequence ranging from +948 to +2097 of the CDS was replaced by the hygromycin resistant cassette ($P_{GPD1}$::hpt-3::Tnos, FIG. 2B). The correct null mutant (Δcar1) was verified by Southern blot analysis (FIG. 2C). As expected, The Δcar1 colony displayed a creamy color rather than the orange color observed in WT. The creamy color of Δcar1 could be further restored to orange by ectopic integration of the allele of CAR1 gene into the genome (Δene i strain in FIG. 2D). Analyses of carotenoid profiles confirmed the loss of β-carotene, γ-carotene, torulene and torularhodin peaks in Δcar1 and all lost peaks were restored in the complemented strain, Δcar1C, with the integration of T-DNA from binary vector pRHCAR1, where the whole allele of CAR1 ranging from −1166 upstream to +517 downstream of the translational start and stop codon, respectively (FIG. 2E). Results strongly support that CAR1 encodes one of the key enzyme involved in carotenoid biosynthesis pathway. To identify more genes in the carotenoid biosynthesis pathway, tBLASTn searches were performed using the U. maydis GGPP synthase (CAR3) (XP_760606, GenBank) and phytoene synthase/carotene cyclase (CAR2) (XP_762434) and the corresponding orthologous sequences in R. toruloides were successfully identified. CAR3 CDS was found located in nt 849806-851310 in scaffold #13 (genome locus RTG_00457, AVER02000013) while CAR2 in nt 396838-399094 in scaffold #18.

We have reported that CAR2 knockout lead to albino phenotype [32]. However, details on its gene structure remained unknown. Using rapid amplification of cDNA ends (RACEs) and reverse transcription PCR (RT-PCR) techniques, cDNA sequences of for CAR1 (SEQ ID NO:1), CAR2 (SEQ ID NO:3), and CAR3 (SEQ ID NO:5) were obtained. The CAR1, CAR2 and CAR3 cDNAs spans 2430, 2334, and 1546 genomic nt in length, containing 10, 8 and 6 exons and encode proteins of 554 (Car1, SEQ ID NO:2), 608 (Car2, SEQ ID NO:4) and 359 (Car3, SEQ ID NO:6) aa, with 19, 77 and 41 nt 5'UTR in the cDNAs, respectively. The corresponding genomic sequences are listed in SEQ ID NOs:7, 8 and 9, respectively. The splicing of the 3 mRNAs strictly follows the canonical GU-AG rule. The results also revealed that the T-DNA of RAMS was integrated into between +681 and +682 from the start codon of CAR1, resulting in premature termination of CAR1 mRNA translation after the 158$^{th}$ aa (FIG. 2B).

Figure 3:
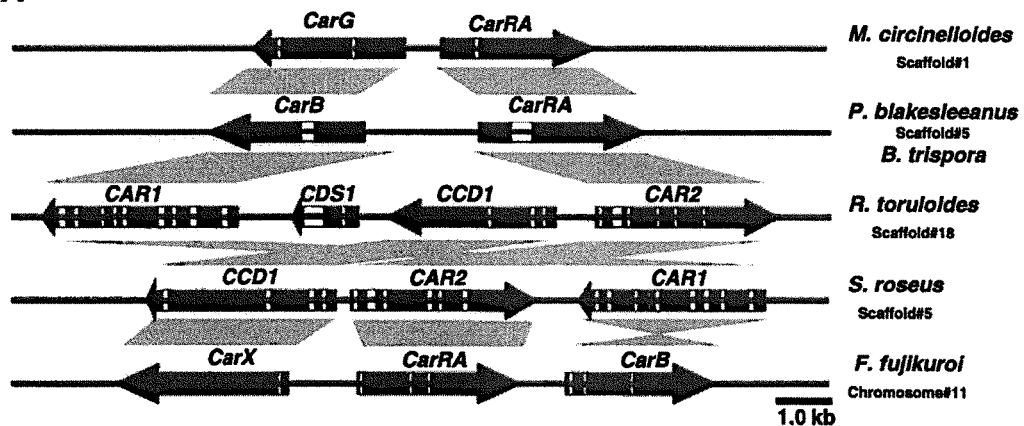
FIG. 3.C: Colony color phenotype of null mutants involved in carotenoid biosynthesis pathway in *R. toruloides*.
Figure 3:
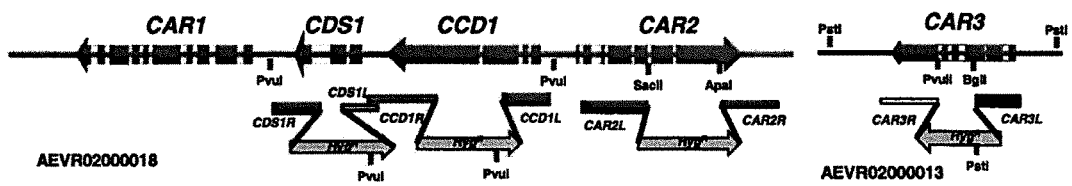
Figure 3:
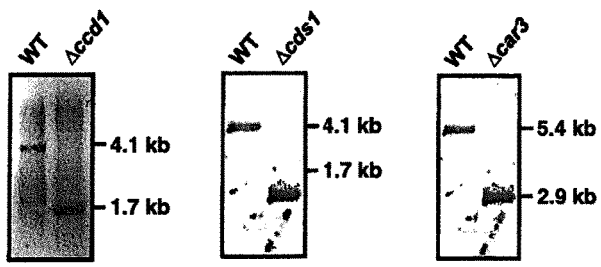
Figure 3:
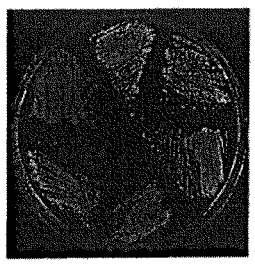
Figure 3:
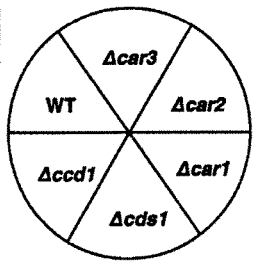
Figure 3:
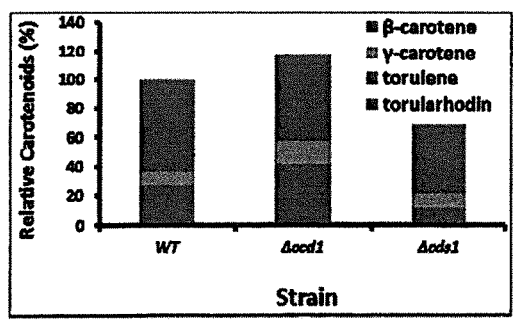
Figure 4:
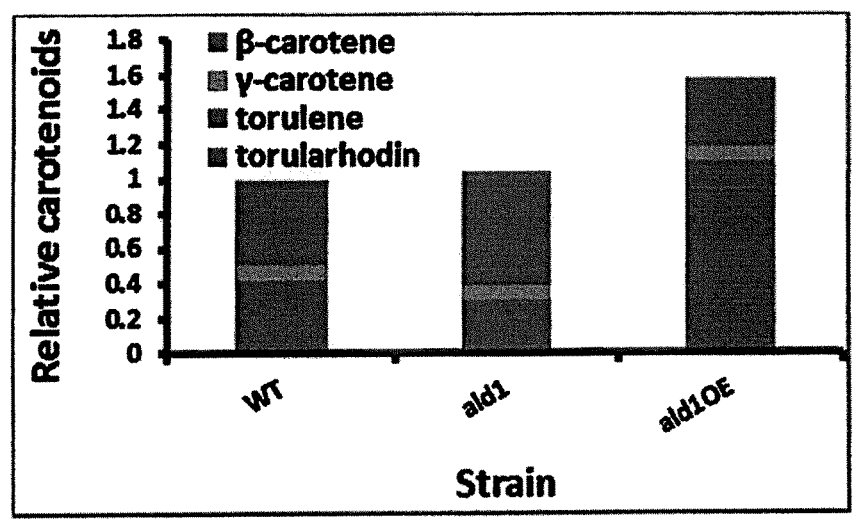
FIG. 4 shows carotenoid profiles in *R. toruloides* wild type strain, Ald1 null mutant (ald1) and overexpression of Ald1OE.

CAR1 and CAR2 are located in the same scaffold #18, separated by a 4354 bp DNA sequence. This organization is analogous to several other carotenogenic fungi, such as Blakeslea trispora, Fusarium fujikuroi, Phycomyces blakesleeanus and Sporobolomyces roseus [49-52] (FIG. 3A). A homologous search (BLASTx, NCBI) of the DNA sequence between the genomic locus CAR1 and CAR2 uncovered two putative genes encoding a carotenoid cleavage dioxygenase (Ccd1) and a carotenoid desaturase (Cds1) (FIG. 3A). 5' and 3' RACEs and RT-PCR revealed that CCD1 (SEQ ID NO:11) and CDS1 (SEQ ID NO:14) cDNAs span 2079 and 793 genomic nt in length, containing 4 and 3 exons with 41 and 19 nt 5'UTR encoding 636 (Ccd1, SEQ ID NO:12) and 224 aa (Cds1, SEQ ID NO:14) proteins, respectively. Again, the splicing strictly follows the canonical GU-AG rule. The corresponding genomic sequences are listed in SEQ ID NOs:10 and 13, respectively.

The divergent organization of CAR1 and CAR2 are analogs to Mucor circinelloides (scaffold#1), Phycomyces blakesleeanus (scaffold#5), Blakeslea trispora and F. fujikuroi (chromosome#11). except that CCD1 and CDS1 gene are found only in R. toruloides. S. roseus genome appeared to have undergone a recombination between CAR1 and CAR2, resulted in loss of CDS1 and translocation of CAR1 (FIG. 5A). F. fujikuroi CarX is located outside of the CarRA (CAR2 ortholog) and CarB (CAR1 ortholog) and considered as the ortholog of CCD1 because its protein product exhibits highly aa sequence homologous to Ccd1 (43% identity). The genetic synteny shared among these carotenogenic fungi suggests a common evolutionary origin of the carotenoid cluster genes.

To confirm their functions in carotenoid biosynthesis, null mutants were created. Similar to Δcar1 and Δcar1, Δcar3 colonies exhibited a creamy color phenotype while Δccd1 and Δcds1 also showed significantly different colors to WT (FIG. 3C). HPLC analysis of their carotenoids revealed totally abolished carotenoid production in either Δcar3, Δcar2 and Δcar1 (data not shown). Total carotenoid production levels were slightly increased in Δccd1 by 18% but dramatically decreased in Δcds1 by 69% (FIG. 3D). Except the slight decrease in β-carotene (6%), regarding to the components of carotenoids accumulated, deletion of CCD1 could result in 86%, 14% and 65% increase in torularhodin, torulene and γ-carotene, respectively (FIG. 3D). In cds1 mutant, the quantitation of all carotenoid components were decreased, especially more than half decreases in torularhodin and torulene (FIG. 3D).

Example 13

Effect of ALD1 Deletion on Carotenoid Production

The RCM6 mutant was initially identified in a screening for genes that affect fatty acid biosynthesis and the representative gene ALD1, a fatty aldehyde dehydrogenase encoding gene, was found to be involved in the degradation of polyunsaturated fatty acid (alpha-linolenic acid, C18:3n=9) (U.S. provisional patent application No. 62/047,300 filed on 8 Sep. 2014, incorporated herein by reference). Regarding to the significant difference in cell color against WT, ALD1 was also studied for the role in carotenoid biosynthesis. The gene deletion mutant Δald1 was generated by homologous recombination through ATMT using the binary vector pKOALD1. To obtain the gene overexpression mutant, the Ald1-RtGFP fusion protein was fused to RtGPD1 promoter and ectopically integrated into Δald1 through ATMT (OEALD1 mutant). After a 5-day fermentation in the carotenoid-producing medium MinCAR, the total carotenoid yield in Δald1 was similar to WT, however beta-carotene level was increased by about 36% while. In contrast, both torulene and torularhadin levels were significantly increased in the ALD1 over expression strain (FIG.

4). A genomic sequence, cDNA sequence and protein sequence for ALD1 are set forth in SEQ ID NOs:16, 17 and 18, respectively.

Example 14 mRNA Profiles of CAR1, CAR2, CAR3, ALD1, CCD1 and CDS1

Figure 5:
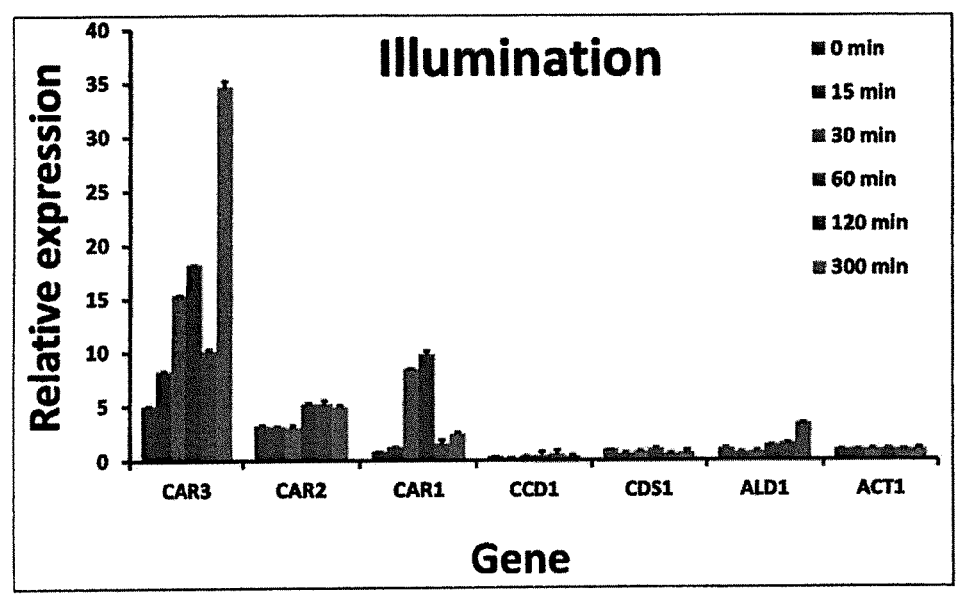
FIG. 5 shows relative mRNA levels of carotenoid biosynthetic genes after switching to lighting. Expression level of each gene was done by qRT-PCR and normalized to Actin gene (ACT1).

Single colonies of R. toruloides ATCC 10657 and carotenoid mutants were inoculated into 50 ml YPD broth in 250 ml conical flasks and cultured at 28° C. and 250 rpm till saturation. The cell cultures were separated in half and cultured continued for each in a shaking platform for 5 more hours, where illumination was conducted using a fluorescent light (Philips TLD 36 W/865, 4 W/m2 white light, 75 cm away) or avoided by covering with aluminum foil. Cells were sampled at various time points and total RNAs were extracted. qRT-PCR was performed in triplicates using oligo pairs qCAR3f/qCAR3r, qCAR2f/qCAR2r, qCAR1f/qCAR1r, qCCD1f/qCCD1r, qCDS1f/qCDS1r and qALD1f/qALD1r for CAR3, CAR2, CAR1, CCD1, CDS1, ALD1, respectively (Table 2). Relative mRNA levels were calculated against the reference gene actin (oligo pair qACT1f/qACT1r, Table 2) using the 2-ΔΔCt method. As shown in FIG. 5, mRNA levels of CAR1 and CAR2 were much lower than that of CAR3 and were likely the bottleneck for the redirection of carbon flux to carotenoid production. CAR1, CAR2, CAR3 and ALD1 mRNA were light inducible.

Example 15

Characterization of ROC1

In *Fusarium fujikuroi*, carS disruption showed an enhanced carotenoid biosynthesis irrespective of light illumination (Avalos and Cerdà-Olmedo 1987). However, genes involved in the earlier steps of terpenoid biosynthesis pathway such as FPP synthase and HMGR, were not affected by the deletion of carS (Rodriguez-Ortiz, Limon et al. 2009).

Using *Fusarium fujikuroi* carS protein sequence (NCBI GenBank accession number CCP50075.1) as query to search against the whole-genome shotgun sequences of R. glutinis ATCC 204091 through the online program tBLASTn (NCBI, USA), a putative ortholog was found in sequence scaffold#9 (E-value and query cover of 4E-37 and 53%, respectively). To be consistent with the gene nomenclature of R. toruloides putative gene was termed ROC1 (Regulator of carotenoid biosynthesis).

5' and 3' RACE yielded a pair of cDNA fragments of approximate 0.9 and 0.7 kb for ROC1 (data not shown). Using oligo pair Rt301Nf and Rt302Evr (Table 2), the full-length cDNA of ROC1 could successfully amplified by RT-PCR (data not shown). Comparison between the cDNA and genomic sequences revealed 5 exons for ROC1 (FIG. 6A), where the splicing junctions abide strictly to the conical GU-AG rule.

ROC1 spans a 3136-nt genome region (SEQ ID NO:19) encoding a mRNA of 2805 nt with a 84 nt 5'UTR (SEQ ID NO:20). ROC1 encodes a 934-aa protein (SEQ ID NO:21) containing a RING-finger domain (C3HC4 type, NCBI conserved domain cd00162) and an ATP-dependent protease La (LON) domain (pfam02190). The sequence shows 96% and 97% aa-identity to a homolog in R. toruloides strain NP11 (EMS19961.1) and CECT1137 (CDR44527.1, respectively).

Figure 6:
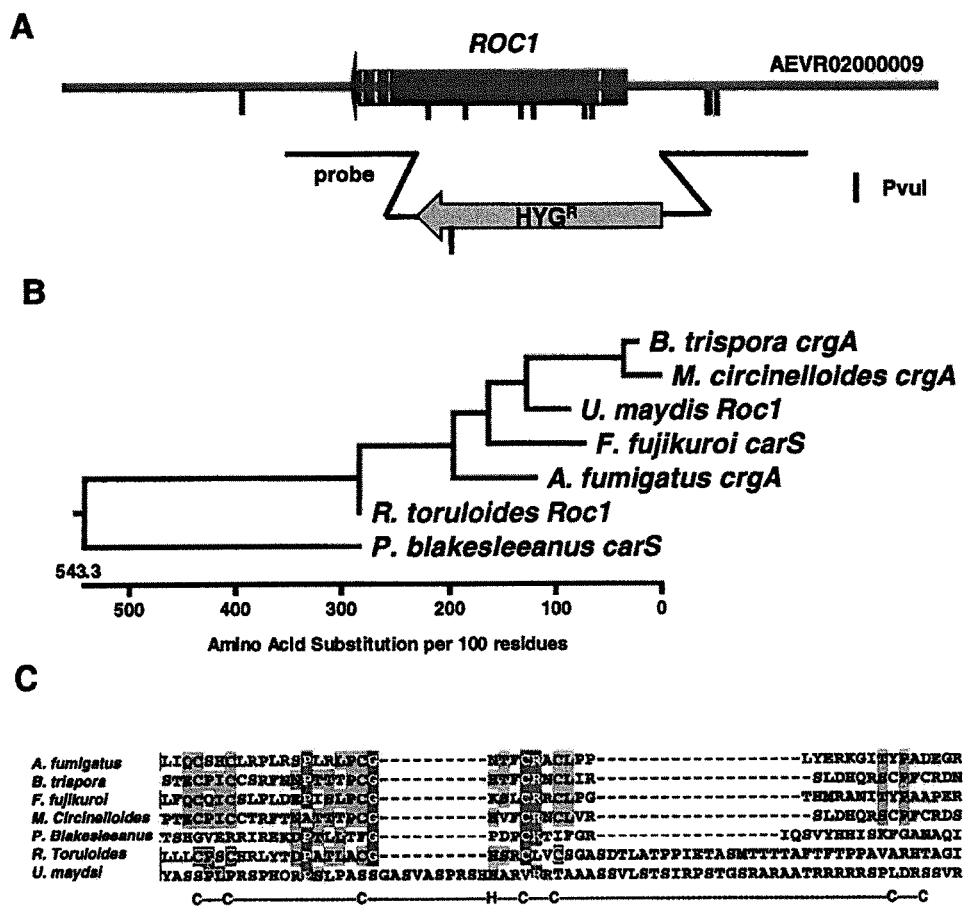
FIGS. 6A-6C show the characterization of Roc1.

ROC1 shares less than 20% identities to orthologs of various carotenogenic fungi except those of two zygomycete, B. trispora and M. cricinelloides (FIG. 6B). Furthermore, the protein sequences within the core RING-finger domain also show very low homology, some even lacking the C3HC4 motif (FIG. 6C).

Example 16

Effects of Deletion of ROC1

Figure 7:
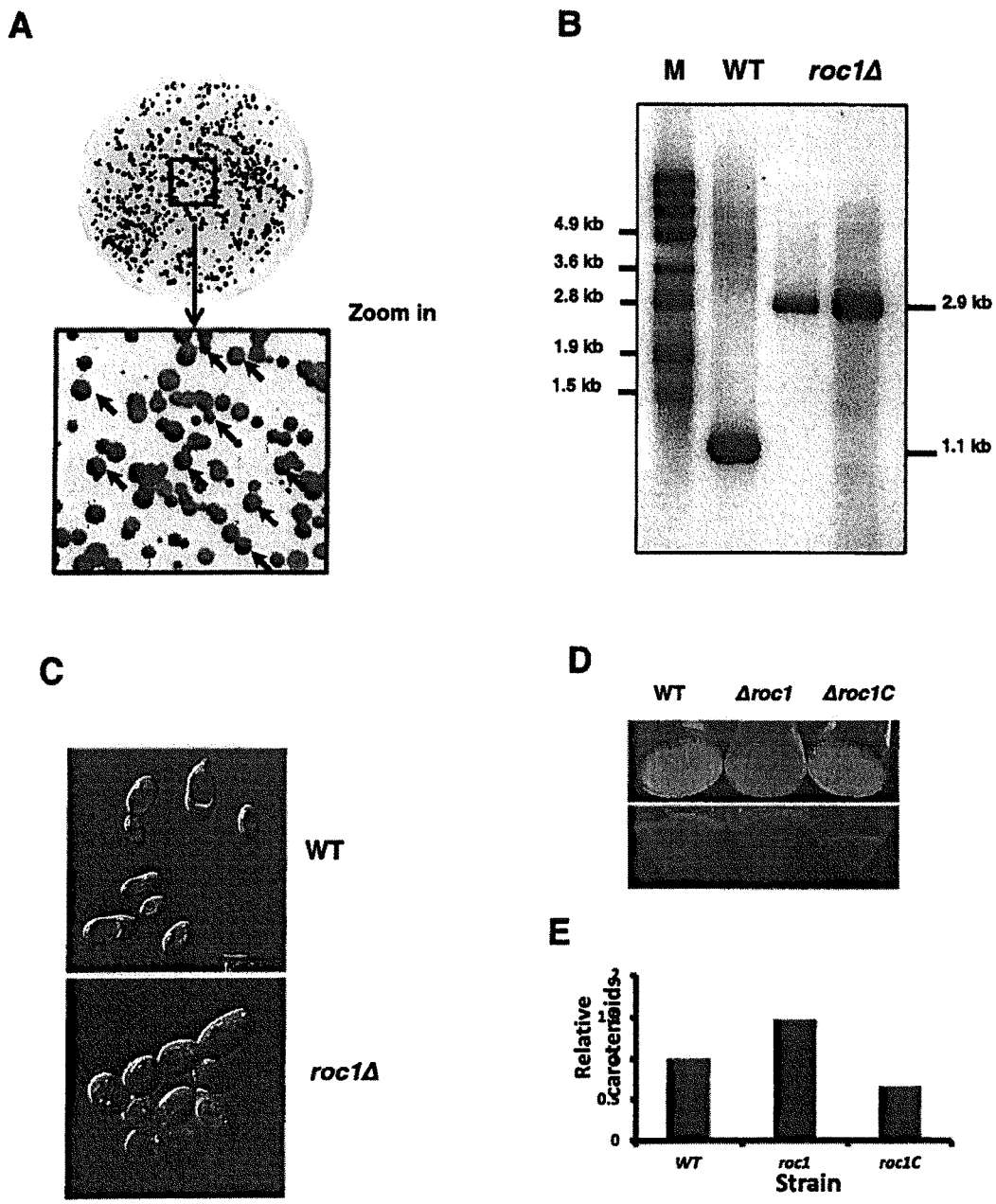
FIGS. 7A-7E show deletion of ROC1.

To genetically understand the role of ROC1 on carotenoid biosynthesis, the ROC1 gene was deleted through homologous recombination (FIG. 7A). Transformation with the gene deletion vector (pKOROC1) showed two kinds of transformants with obvious color differences, light and deep orange (FIG. 7A), and the deep orange transformants were found to be the true knockouts by Southern blot analysis (FIG. 7B). roc1 null mutants showed similar cell morphology and growth to WT (FIGS. 7C and 7D). However, significant improvement of carotene biosynthesis could be observed in roc1 mutants and this could be completed restored by introduction of a WT ROC1 gene allele in roc1 mutant (FIG. 7D). Surprisingly, cell biomass production was significantly decreased in the complementation mutant (FIG. 7D). Quantitation analysis revealed that the 5-day culture in MinCAR medium yielded about 1.5-fold more carotenoids in roc1 mutant as compared to those in WT (FIG. 7E).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Hirschberg J: Carotenoid biosynthesis in flowering plants. *Current opinion in plant biology* 2001, 4:210-218.

2. Armstrong G A, Hearst J E: Carotenoids 2: Genetics and molecular biology of carotenoid pigment biosynthesis. *FASEB J* 1996, 10:228-237.
3. Eisenreich W, Bacher A, Arigoni D, Rohdich F: Biosynthesis of isoprenoids via the non-mevalonate pathway. *Cellular and Molecular Life Sciences CMLS* 2004, 61:1401-1426.
4. Martin V J, Pitera D J, Withers S T, Newman M, Keasling J D: Engineering a mevalonate pathway in *Escherichia coli* for production of terpenoids. *Nature biotechnology* 2003, 21:796-802.
5. Armstrong G A, Hearst J E: Carotenoids 2: Genetics and molecular biology of carotenoid pigment biosynthesis. *The FASEB Journal* 1996, 10:228-237.
6. Kajiwara S, Kakizono T, Saito T, Kondo K, Ohtani T, Nishio N, Nagai S, Misawa N: Isolation and functional identification of a novel cDNA for astaxanthin biosynthesis from Haematococcus pluvialis, and astaxanthin synthesis in *Escherichia coli*. *Plant molecular biology* 1995, 29:343-352.
7. Fraser P D, Miura Y, Misawa N: In vitro characterization of astaxanthin biosynthetic enzymes. *Journal of Biological Chemistry* 1997, 272:6128-6135.
8. Cunningham F X, Gantt E: Genes and Enzymes of Carotenoid Biosynthesis in Plants. *Annu Rev Plant Physiol Plant Mol Biol* 1998, 49:557-583.
9. Mapari S A, Nielsen K F, Larsen T O, Frisvad J C, Meyer A S, Thrane U: Exploring fungal biodiversity for the production of water-soluble pigments as potential natural food colorants. *Current Opinion in Biotechnology* 2005, 16:231-238.
10. Takaichi S: Carotenoids and carotenogenesis in anoxygenic photosynthetic bacteria. In *The photochemistry of carotenoids*. Springer; 1999: 39-69
11. Cobbs C, Heath J, Stireman III J O, Abbot P: Carotenoids in unexpected places: Gall midges, lateral gene transfer, and carotenoid biosynthesis in animals. *Molecular phylogenetics and evolution* 2013, 68:221-228.
12. Sporn M, Dunlop N, Newton D, Smith J: Prevention of chemical carcinogenesis by vitamin A and its synthetic analogs (retinoids). In *Federation proceedings*. 1976: 1332-1338.
13. Seddon J M, Ajani U A, Sperduto R D, Hiller R, Blair N, Burton T C, Farber M D, Gragoudas E S, Haller J, Miller D T: Dietary carotenoids, vitamins A, C, and E, and advanced age-related macular degeneration. *Jama* 1994, 272:1413-1420.
14. Wolbach S B, Howe P R: Tissue changes following deprivation of fat-soluble A vitamin. *The Journal of experimental medicine* 1925, 42:753-777.
15. Miki W: Biological functions and activities of animal carotenoids. *Pure and Applied Chemistry* 1991, 63:141-146.
16. Estrada A F, Brefort T, Mengel C, Díaz-Sánchez V, Alder A, Al-Babili S, Avalos J: Ustilago maydis accumulates isefort T, Mengel C, Díaz-Sánchez V, Alder A, Al-Babili S, Avalos J: J: io *Fungal Genetics and Biology* 2009, 46:803-813.
17. Giovannucci E, Ascherio A, Rimm E B, Stampfer M J, Colditz G A, Willett W C: Intake of carotenoids and retino in relation to risk of prostate cancer. *Journal of the national cancer institute* 1995, 87:1767-1776.
18. Spencer K G: Pigmentation supplements for animal feed compositions. Google Patents; 1989.
19. Herring P: The carotenoid pigments of *Daphnia magna* straus—I. The pigments of animals feed *Chlorella pyrenoidosa* and pure carotenoids. *Comparative biochemistry and physiology* 1968, 24:187-203.
20. Mortensen A: Carotenoids and other pigments as natural colorants. *Pure and Applied Chemistry* 2006, 78:1477-1491.
21. Peter F, Andrea L-R, Peter W, Naoharu W: Carotenoid Cleavage Enzymes in Animals and Plants. In *Carotenoid-Derived Aroma Compounds. Volume* 802: American Chemical Society; 2001: 76-88: *ACS Symposium Series*].
22. Duester G: Involvement of alcohol dehydrogenase, short-chain dehydrogenase/reductase, aldehyde dehydrogenase, and cytochrome P450 in the control of retinoid signaling by activation of retinoic acid synthesis. *Biochemistry* 1996, 35:12221-12227.
23. Li Y, Zhao Z K, Bai F: High-density cultivation of oleaginous yeast Rhodosporidium toruloides Y4 in fed-batch culture. *Enzyme and Microbial Technology* 2007, 41:312-317.
24. Zhao X, Hu C, Wu S, Shen H, Zhao Z K: Lipid production by Rhodosporidium toruloides Y4 using different substrate feeding strategies. *J Ind Microbiol Biotechnol* 2011, 38:627-632.
25. Pan J G, Kwak M Y, Rhee J S: High density cell culture of *Rhodotorula glutinis* using oxygen-enriched air. *Biotechnology letters* 1986, 8:715-718.
26. Frengova G I, Beshkova D M: Carotenoids from *Rhodotorula* and *Phaffia*: yeasts of biotechnological importance. *J Ind Microbiol Biotechnol* 2009, 36:163-180.
27. Cerdá-Olmedo E: Production of carotenoids with fungi. In *Biotechnology of vitamins, pigments and growth factors*. Springer; 1989: 27-42
28. Buzzini P, Martini A: Production of carotenoids by strains of *Rhodotorula glutinis* cultured in raw materials of agro-industrial origin. *Bioresource technology* 2000, 71:41-44.
29. Frengova G I, Beshkova D M: Carotenoids from *Rhodotorula* and *Phaffia*: yeasts of biotechnological importance. *Journal of industrial microbiology & biotechnology* 2009, 36:163-180.
30. Bhosale P, Gadre R: βBhosale P production in sugarcane molasses by a *Rhodotorula glutinis* mutant. *Journal of Industrial Microbiology and Biotechnology* 2001, 26:327-332.
31. Sperstad S, Lutnes B, Stormo S, Liaaen-Jensen S, Landfald B: Torularhodin and torulene are the major contributors to the carotenoid pool of marine *Rhodosporidium babjevae* (Golubev). *Journal of Industrial Microbiology and Biotechnology* 2006, 33:269-273.
32. Koh C M, Liu Y, Du M, Ji L: Molecular characterization of KU70 and KU80 homologues and exploitation of a KU70-deficient mutant for improving gene deletion frequency in *Rhodosporidium toruloides*. *BMC Microbiology* 2014, 14:50.
33. Lazo G R, Stein P A, Ludwig R A: A DNA transformation-competent *Arabidopsis* genomic library in *Agrobacterium*. *Biotechnology (N Y)* 1991, 9:963-967.
34. Cai L, Sun L, Fu L, Ji L: media compositions, selection methods and *agrobacterium* strains for transformation of plants. Google Patents; 2009.
35. Buzzini P, Martini A: Production of carotenoids by strains of *Rhodotorula glutinis* cultured in raw materials of agro-industrial origin. *Bioresource Technology* 1999, 71:41-44.
36. Wu S, Hu C, Jin G, Zhao X, Zhao Z K: Phosphate-limitation mediated lipid production by *Rhodosporidium toruloides*. *Bioresour Technol* 2010, 101:6124-6129.

37. Liu Y, Koh C M, Sun L, Hlaing M M, Du M, Peng N, Ji L: Characterization of glyceraldehyde-3-phosphate dehydrogenase gene RtGPD1 and development of genetic transformation method by dominant selection in oleaginous yeast *Rhodosporidium toruloides*. *Appl Microbiol Biotechnol* 2013, 97:719-729.

38. Smith T L, Leong S A: Isolation and characterization of a *Ustilago maydis* glyceraldehyde-3-phosphate dehydrogenase-encoding gene. *Gene* 1990, 93:111-117.

39. Ji L, Jiang Z D, Liu Y, Koh C M, Zhang L H: A Simplified and efficient method for transformation and gene tagging of *Ustilago maydis* using frozen cells. *Fungal Genet Biol* 2010, 47:279-287.

40. Punt P J, Dingemanse M A, Kuyvenhoven A, Soede R D, Pouwels P H, van den Hondel C A: Functional elements in the promoter region of the *Aspergillus nidulans* gpdA gene encoding glyceraldehyde-3-phosphate dehydrogenase. *Gene* 1990, 93:101-109.

41. Steiner S, Philippsen P: Sequence and promoter analysis of the highly expressed TEF gene of the filamentous fungus *Ashbya gossypii*. *Mol Gen Genet* 1994, 242:263-271.

42. Liu Y, Koh C M J, Sun L, Hlaing M M, Du M, Peng N, Ji L: Characterization of glyceraldehyde-3-phosphate dehydrogenase gene RtGPD1 and development of genetic transformation method by dominant selection in oleaginous yeast *Rhodosporidium toruloides*. *Applied microbiology and biotechnology* 2013, 97:719-729.

43. Liu Y G, Whittier R F: Thermal asymmetric interlaced PCR: automatable amplification and sequencing of insert end fragments from P1 and YAC clones for chromosome walking. *Genomics* 1995, 25:674-681.

44. Liu Y G, Chen Y: High-efficiency thermal asymmetric interlaced PCR for amplification of unknown flanking sequences. *Biotechniques* 2007, 43:649-650, 652, 654 passim.

45. Saelices L, Youssar L, Holdermann I, Al-Babili S, Avalos J: Identification of the gene responsible for torulene cleavage in the Neurospora carotenoid pathway. *Mol Genet Genomics* 2007, 278:527-537.

46. Bijttebier S, D'Hondt E, Noten B, Hermans N, Apers S, Voorspoels S: Ultra high performance liquid chromatography versus high performance liquid chromatography: stationary phase selectivity for generic carotenoid screening. *J Chromatogr A* 2014, 1332:46-56.

47. Bijttebier S K, D'Hondt E, Hermans N, Apers S, Voorspoels S: Unravelling ionization and fragmentation pathways of carotenoids using orbitrap technology: a first step towards identification of unknowns. *J Mass Spectrom* 2013, 48:740-754.

48. Hausmann A, Sandmann G: A single five-step desaturase is involved in the carotenoid biosynthesis pathway to beta-carotene and torulene in *Neurospora crassa*. *Fungal Genet Biol* 2000, 30:147-153.

49. Keller N P, Turner G, Bennett J W: Fungal secondary metabolism—from biochemistry to genomics. *Nature Reviews Microbiology* 2005, 3:937-947.

50. Linnemannstons P, Prado M M, Fernandez-Martin R, Tudzynski B, Avalos J: A carotenoid biosynthesis gene cluster in *Fusarium fujikuroi*: the genes carB and carRA. *Mol Genet Genomics* 2002, 267:593-602.

51. Thewes S, Prado-Cabrero A, Prado M M, Tudzynski B, Avalos J: Characterization of a gene in the car cluster of *Fusarium fujikuroi* that codes for a protein of the carotenoid oxygenase family. *Mol Genet Genomics* 2005, 274: 217-228.

52. Jin J M, Lee J, Lee Y W: Characterization of carotenoid biosynthetic genes in the ascomycete *Gibberella zeae*. *FEMS Microbiol Lett* 2010, 302:197-202.

53. Moline M, Flores M R, Libkind D, Dieguez Mdel C, Farias M E, van Broock M: Photoprotection by carotenoid pigments in the yeast *Rhodotorula mucilaginosa*: the role of torularhodin. *Photochemical & photobiological sciences: Official journal of the European Photochemistry Association and the European Society for Photobiology* 2010, 9:1145-1151.

54. Moline M, Libkind D, van Broock M: Production of torularhodin, torulene, and beta-carotene by *Rhodotorula* yeasts. *Methods Mol Biol* 2012, 898:275-283.

55. Buzzini P, Innocenti M, Turchetti B, Libkind D, van Broock M, Mulinacci N: Carotenoid profiles of yeasts belonging to the genera *Rhodotorula*, *Rhodosporidium*, *Sporobolomyces*, and *Sporidiobolus*. *Can J Microbiol* 2007, 53:1024-1031.

56. Liu Z J, Sun Y J, Rose J, Chung Y J, Hsiao C D, Chang W R, Kuo I, Perozich J, Lindahl R, Hempel J, Wang B C: The first structure of an aldehyde dehydrogenase reveals novel interactions between NAD and the Rossmann fold. *Nat Struct Biol* 1997, 4:317-326.

57. Lee L Y, Gelvin S B: T-DNA binary vectors and systems. *Plant Physiol* 2008, 146:325-332.

Bonfim, K. et al. (2007). RNAi-mediated resistance to Bean golden mosaic virus in genetically engineered common bean (*Phaseolus vulgaris*). *Mol Plant Microbe Interact* 20:717-726.

Durai, S. et al. (2005). Zinc finger nucleases: custom-designed molecular scissors for genome engineering of plant and mammalian cells. *Nucl Acids Res* 33:5978-5990.

Fuentes, A. et al. (2006). Intron-hairpin RNA derived from replication associated protein C1 gene confers immunity to tomato yellow leaf curl virus infection in transgenic tomato plants. *Transgenic Res* 15:291-304.

Guo, H. S. et al (2003). A chemical-regulated inducible RNAi system in plants. *Plant J* 34:383-392.

Makarova, K. S. et al. (2011). Evolution and classification of the CRISPR-Cas systems. *Nat Rev Microbiol* 9:467-477.

Mali, P. et al. (2013). RNA-guided human genome engineering via Cas9. *Science* 339:823-826.

Mysara, M. et al. (2011). MysiRNA-designer: a workflow for efficient siRNA design. *PLOS one* 6(10):e25642.

Vanderschuren, H. et al (2007a). Transgenic cassava resistance to African cassava mosaic virus is enhanced by viral DNA-A bidirectional promoter-derived siRNAs. *Plant Mol Biol* 64:549-557.

Vanderschuren, H. et al. (2007b). Engineering resistance to geminiviruses—review and perspectives. *Plant Biotechnology Journal* 5:207-220.

Wang, M. B. et al. (2000). A single copy of a virus-derived transgene encoding hairpin RNA gives immunity to barley yellow dwarf virus. *Mol Plant Pathol* 1:347-356.

Wesley, S. V. et al. (2001). Construct design for efficient, effective and high-throughput gene silencing in plants. *Plant J* 27:581-590.

Yan, P. et al. (2012). High-throughput construction of intron-containing hairpin RNA vectors for RNAi in plants. *PLOS one* 7(5):e38186.

Zrachya, A. et al. (2007). Production of siRNA targeted against TYLCV coat protein transcripts leads to silencing of its expression and resistance to the virus. *Transgenic Res* 16:385-398.

What is claimed is:

1. A method for tuning the production level and composition of carotenoids in a fungal host comprising:
(a) genetically manipulating a fungal host selected from the group consisting of *Rhodosporidium* and *Rodotorula*, wherein the genetic manipulation comprises deleting all or part of one or more polynucleotides selected from the group consisting of:
(i) a polynucleotide encoding a polypeptide having a sequence set forth in SEQ ID NO:12 or at least 95% identity thereto,
(ii) a polynucleotide encoding a polypeptide having a sequence set forth in SEQ ID NO:18 or at least 95% identity thereto, and
(iii) a polynucleotide encoding a polypeptide having a sequence set forth in SEQ ID NO:21 or at least 95% identity thereto,
wherein the deletion of all or part of polynucleotide (i) totally inactivates the enzyme activity of the polypeptide encoded by polynucleotide (i),
wherein the deletion of all or part of polynucleotide (ii) totally inactivates the enzyme activity of the polypeptide encoded by polynucleotide (ii), and
wherein the deletion of all or part of polynucleotide (iii) totally inactivates the enzyme activity of the polypeptide encoded by polynucleotide (iii); and
(b) growing the fungal host to produce carotenoids, wherein the carotenoids are selected from the group consisting of lycopene, beta-carotene, gamma-carotene, torulene and torularhodin or derivatives thereof,
whereby the production level or composition of the carotenoids is tuned compared to a fungal host not having the genetic manipulation.

2. The method of claim 1, wherein the deletion is made by homologous recombination.

3. The method of claim 1, wherein the deletion is made using an artificial nuclease selected from a Zinc finger nuclease or a Cas9-gRNA complex.

4. The method of claim 1, wherein the genetic manipulation further comprises over-expressing one or more polynucleotides selected from the group consisting of
(iv) a polynucleotide encoding a polypeptide having a sequence set forth in SEQ ID NO:2 or at least 95% identity thereto,
(v) a polynucleotide encoding a polypeptide having a sequence set forth in SEQ ID NO:4 or at least 95% identity thereto,
(vi) a polynucleotide encoding a polypeptide having a sequence set forth in SEQ ID NO:6 or at least 95% identity thereto, and
(vii) a polynucleotide encoding a polypeptide having a sequence set forth in SEQ ID NO:15 or at least 95% identity thereto,
wherein the over-expression is compared to a fungal host not having the genetic manipulation.

5. The method of claim 4, wherein the one or more polynucleotides are over-expressed by introducing one or more DNA molecules into the fungal host, wherein each DNA molecule comprises one or more constructs and wherein each construct comprises a heterologous promoter operatively linked to one of the polynucleotides operatively linked to a transcriptional terminator.

6. The method of claim 4, wherein
polynucleotide (i) has the sequence set forth in SEQ ID NO:10 or 11,
polynucleotide (ii) has the sequence set forth in SEQ ID NO:16 or 17,
polynucleotide (iii) has the sequence set forth in SEQ ID NO:19 or 20,
polynucleotide (iv) has the sequence set forth in SEQ ID NO:1,
polynucleotide (v) has the sequence set forth in SEQ ID NO:3,
polynucleotide (vi) has the sequence set forth in SEQ ID NO:5,
polynucleotide (vii) has the sequence set forth in SEQ ID NO:13 or 14.

7. The method of claim 1, wherein the genetic manipulation further comprises down-regulating one or more different polynucleotides selected from the group consisting of
(iv) a polynucleotide encoding a polypeptide having a sequence set forth in SEQ ID NO:2 or at least 95% identity thereto,
(v) a polynucleotide encoding a polypeptide having a sequence set forth in SEQ ID NO:4 or at least 95% identity thereto,
(vi) a polynucleotide encoding a polypeptide having a sequence set forth in SEQ ID NO:6 or at least 95% identity thereto, and
(vii) a polynucleotide encoding a polypeptide having a sequence set forth in SEQ ID NO:15 or at least 95% identity thereto,
wherein the down-regulation is compared to a fungal host not having the genetic manipulation.

8. The method of claim 7, wherein the one or more polynucleotides are down-regulated by RNAi, artificial transcriptional repressor or weak promoter.

9. The method of claim 7, wherein
polynucleotide (i) has the sequence set forth in SEQ ID NO:10 or 11,
polynucleotide (ii) has the sequence set forth in SEQ ID NO:16 or 17,
polynucleotide (iii) has the sequence set forth in SEQ ID NO:19 or 20,
polynucleotide (iv) has the sequence set forth in SEQ ID NO:1,
polynucleotide (v) has the sequence set forth in SEQ ID NO:3,
polynucleotide (vi) has the sequence set forth in SEQ ID NO:5, polynucleotide (vii) has the sequence set forth in SEQ ID NO:13 or 14.

10. The method of claim 1, wherein the fungal host is grown in a medium comprising at least 5% of a carbon source at a temperature from about 25° C. to about 35° C.

11. The method of claim 10, wherein the carbon source is glucose, mannose, glycerol, sucrose, xylose or combinations thereof.

12. The method of claim 10, wherein the medium comprises 30-100 g/L glucose, 1.5 g/L yeast extract, 0.5 g/L $(NH_4)_2SO_4$, 2.05 g/L $K_2HPO_4$, 1.45 g/L $KH_2PO_4$, 0.6 g/L $MgSO_4$, 0.3 g/L NaCl, 10 mg $CaCl_2$, 1 mg/L $FeSO_4$, 0.5 mg/L $ZnSO_4$, 0.5 mg/L $CuSO_4$, 0.5 mg/L $H_3BO_4$, 0.5 mg/L $MnSO_4$, 0.5 mg/L $NaMoO_4$, wherein pH of the medium is from about 5 to about 7.

13. The method of claim 10, wherein the fungal host is grown under illumination.

14. The method of claim 13, wherein the carbon source is glucose, mannose, glycerol, sucrose, xylose or combinations thereof.

15. The method of claim 13, wherein the medium comprises 30-100 g/L glucose, 1.5 g/L yeast extract, 0.5 g/L $(NH_4)_2SO_4$, 2.05 g/L $K_2HPO_4$, 1.45 g/L $KH_2PO_4$, 0.6 g/L $MgSO_4$, 0.3 g/L NaCl, 10 mg $CaCl_2$, 1 mg/L $FeSO_4$, 0.5 mg/L $ZnSO_4$, 0.5 mg/L $CuSO_4$, 0.5 mg/L $H_3BO_4$, 0.5 mg/L $MnSO_4$, 0.5 mg/L $NaMoO_4$, wherein pH of the medium is from about 5 to about 7.

16. The method of claim 1, wherein
polynucleotide (i) has the sequence set forth in SEQ ID NO:10 or 11,
polynucleotide (ii) has the sequence set forth in SEQ ID NO:16 or 17, and
polynucleotide (iii) has the sequence set forth in SEQ ID NO:19 or 20.

\* \* \* \* \*

SEQUENCE LISTING

<160> NUMBER OF SEQ ID NOS: 118

<210> SEQ ID NO 1
<211> LENGTH: 1684
<212> TYPE: DNA
<213> ORGANISM: Rhodosporidium toruloides
<220> FEATURE:
<221> NAME/KEY: CDS
<222> LOCATION: (20)..(1684)

<400> SEQUENCE: 1

```
accactcgct agtgaagca atg gca gct gcg aac gga cac ggc aag gga aag            52
                    Met Ala Ala Ala Asn Gly His Gly Lys Gly Lys
                     1               5                  10 ccc tcg gtg ctc atc gtc gga gcg ggc gtc gga ggc act gcg tcc gcc           100
Pro Ser Val Leu Ile Val Gly Ala Gly Val Gly Gly Thr Ala Ser Ala
             15                  20                  25 gct cgc ctc gcc cag tcc ggg ttc gac gtg aca gtc ctc gag aag aac           148
Ala Arg Leu Ala Gln Ser Gly Phe Asp Val Thr Val Leu Glu Lys Asn
         30                  35                  40 gac ttt gcc ggc gga cga tgc tcc ctc ttc acc gat ccg acc aag tcc           196
Asp Phe Ala Gly Gly Arg Cys Ser Leu Phe Thr Asp Pro Thr Lys Ser
     45                  50                  55 ttc cgc ttc gac cag ggc ccg agc ctg ttc ctc atc ccg cga ctg ttc           244
Phe Arg Phe Asp Gln Gly Pro Ser Leu Phe Leu Ile Pro Arg Leu Phe
 60                  65                  70                  75 gac gag acc ttc agc gac ctc ggg acg agc ctt gag aac gag ggc atc           292
Asp Glu Thr Phe Ser Asp Leu Gly Thr Ser Leu Glu Asn Glu Gly Ile
                 80                  85                  90 aag ctt gtc aag tgc gag cca aac tac cgg atc gtc ttc ccc gac aag           340
Lys Leu Val Lys Cys Glu Pro Asn Tyr Arg Ile Val Phe Pro Asp Lys
             95                 100                 105 gag gtc gtc gag atg agc agc gac ttg acg agg atg aag aag cag gtc           388
Glu Val Val Glu Met Ser Ser Asp Leu Thr Arg Met Lys Lys Gln Val
        110                 115                 120 gag cgg tgg gag gga gag aag ggc ttt gaa gga ttt ctc ggc ttc ctg           436
Glu Arg Trp Glu Gly Glu Lys Gly Phe Glu Gly Phe Leu Gly Phe Leu
    125                 130                 135 aag gag gga cat gcg cac tac gag ctg tcg atg gtt cac gtc ctc cac           484
Lys Glu Gly His Ala His Tyr Glu Leu Ser Met Val His Val Leu His
140                 145                 150                 155 cgc aac ttc acc tcg ctc ctc tcg atg gtc cgc ccg tct ctg atc atc           532
Arg Asn Phe Thr Ser Leu Leu Ser Met Val Arg Pro Ser Leu Ile Ile
                160                 165                 170 cag ctc cgc aag ctc cat ccc ttt gtc tct gtc tat tcg cgc gcg acc           580
Gln Leu Arg Lys Leu His Pro Phe Val Ser Val Tyr Ser Arg Ala Thr
            175                 180                 185 aag tac ttc aag acg gac cgc atg cgg aga gcg ttc acc ttt gcg tcc           628
Lys Tyr Phe Lys Thr Asp Arg Met Arg Arg Ala Phe Thr Phe Ala Ser
        190                 195                 200 atg tac ctt ggc atg tct ccc ttc gac gct ctc ggc gcc tac aac ctc           676
Met Tyr Leu Gly Met Ser Pro Phe Asp Ala Leu Gly Ala Tyr Asn Leu
    205                 210                 215 ctc cag tac acc gag cac tgc gaa ggc atc ctc tac cct ctc ggt ggt           724
Leu Gln Tyr Thr Glu His Cys Glu Gly Ile Leu Tyr Pro Leu Gly Gly
220                 225                 230                 235 ttc ggt cgc atc cct caa acc ctc caa aaa ctc gcc gaa aag agc ggc           772
Phe Gly Arg Ile Pro Gln Thr Leu Gln Lys Leu Ala Glu Lys Ser Gly
                240                 245                 250 gcc aag ttc cgc ttc aac agt ccc gtc aag cgc gtc acg gtg gag aat           820
Ala Lys Phe Arg Phe Asn Ser Pro Val Lys Arg Val Thr Val Glu Asn
```

```
ggc acg gcc aag ggt gtt gaa ctc gag agt ggc gag aag ttg aag gcc    868
Gly Thr Ala Lys Gly Val Glu Leu Glu Ser Gly Glu Lys Leu Lys Ala
        270                 275                 280 gag atc gtc ctc gtc aat gcg gat ttg gtg tgg agt atg gcg cat ttg    916
Glu Ile Val Leu Val Asn Ala Asp Leu Val Trp Ser Met Ala His Leu
285                 290                 295 tac gag gag acg agc tac tcg aag agg ctc gag gag cgc ccc gtc agc    964
Tyr Glu Glu Thr Ser Tyr Ser Lys Arg Leu Glu Glu Arg Pro Val Ser
300                 305                 310                 315 tgc tcg tcc atc tcg ttt tac tgg tcg atg aac cgc aag ata ccc cag   1012
Cys Ser Ser Ile Ser Phe Tyr Trp Ser Met Asn Arg Lys Ile Pro Gln
                320                 325                 330 ctc gac tcg cat acc atc ttc ctc gca gag gag tac cga gag tcc ttc   1060
Leu Asp Ser His Thr Ile Phe Leu Ala Glu Glu Tyr Arg Glu Ser Phe
                335                 340                 345 gac tcg atc ttc cgc gaa cac cgt atc ccg cat gag cct tcc ttc tac   1108
Asp Ser Ile Phe Arg Glu His Arg Ile Pro His Glu Pro Ser Phe Tyr
350                 355                 360 gtc aac gtc ccc agc cgt cac gac cct tct gcc gct ccc gcc gac aaa   1156
Val Asn Val Pro Ser Arg His Asp Pro Ser Ala Ala Pro Ala Asp Lys
365                 370                 375 gac gcc gtc atc gtc ctc gtc ccc gtc ggg cac att tcc gcc gcc ctc   1204
Asp Ala Val Ile Val Leu Val Pro Val Gly His Ile Ser Ala Ala Leu
380                 385                 390                 395 ccc tcc tct tcc gac tgg gac aaa gtg gtc gaa gac acg cgt aac aag   1252
Pro Ser Ser Ser Asp Trp Asp Lys Val Val Glu Asp Thr Arg Asn Lys
                400                 405                 410 att atc ggc gag atc gag cgc cga ctc gac atc aag gac ctc cga ggc   1300
Ile Ile Gly Glu Ile Glu Arg Arg Leu Asp Ile Lys Asp Leu Arg Gly
            415                 420                 425 tgc atc gag cac gag acg atc aac acg cct atc act tgg ggc gag aag   1348
Cys Ile Glu His Glu Thr Ile Asn Thr Pro Ile Thr Trp Gly Glu Lys
            430                 435                 440 ttc aac ttg cac cgc ggc agt atc ctt gga ctc agt cac gac ttc ttc   1396
Phe Asn Leu His Arg Gly Ser Ile Leu Gly Leu Ser His Asp Phe Phe
            445                 450                 455 aac gtc ctc tct ttc cgc ccc aag acc cgc cac ccg agc gtc aag aac   1444
Asn Val Leu Ser Phe Arg Pro Lys Thr Arg His Pro Ser Val Lys Asn
460                 465                 470                 475 gct tac ttc gtc ggc gcg tct gcg cac ccg gga act ggc gtc ccc atc   1492
Ala Tyr Phe Val Gly Ala Ser Ala His Pro Gly Thr Gly Val Pro Ile
                480                 485                 490 gtc ctc gcc ggc gcc cgc ctc gtc gca acc cag atc ctc aac gac ctc   1540
Val Leu Ala Gly Ala Arg Leu Val Ala Thr Gln Ile Leu Asn Asp Leu
                495                 500                 505 ggc atg ccc atc ccc tcg cgc tgg aac gtc tcc tcc tcc gaa ctc gcg   1588
Gly Met Pro Ile Pro Ser Arg Trp Asn Val Ser Ser Ser Glu Leu Ala
        510                 515                 520 acg cac aag acg atc cgc gat gcg gcg gga ggg ttc acc ctc ctc tcg   1636
Thr His Lys Thr Ile Arg Asp Ala Ala Gly Gly Phe Thr Leu Leu Ser
525                 530                 535 gtg ttg ttt ggg ctg atc gcg ttg ttg gtc atg tat ctg cgc gga tga   1684
Val Leu Phe Gly Leu Ile Ala Leu Leu Val Met Tyr Leu Arg Gly
540                 545                 550

<210> SEQ ID NO 2
<211> LENGTH: 554
<212> TYPE: PRT
<213> ORGANISM: Rhodosporidium toruloides
```

<400> SEQUENCE: 2

```
Met Ala Ala Ala Asn Gly His Gly Lys Gly Pro Ser Val Leu Ile
1               5                   10                  15

Val Gly Ala Gly Val Gly Gly Thr Ala Ser Ala Ala Arg Leu Ala Gln
            20                  25                  30

Ser Gly Phe Asp Val Thr Val Leu Glu Lys Asn Asp Phe Ala Gly Gly
            35                  40                  45

Arg Cys Ser Leu Phe Thr Asp Pro Thr Lys Ser Phe Arg Phe Asp Gln
    50                  55                  60

Gly Pro Ser Leu Phe Leu Ile Pro Arg Leu Phe Asp Glu Thr Phe Ser
65                  70                  75                  80

Asp Leu Gly Thr Ser Leu Glu Asn Glu Gly Ile Lys Leu Val Lys Cys
                85                  90                  95

Glu Pro Asn Tyr Arg Ile Val Phe Pro Asp Lys Glu Val Val Glu Met
            100                 105                 110

Ser Ser Asp Leu Thr Arg Met Lys Lys Gln Val Glu Arg Trp Glu Gly
            115                 120                 125

Glu Lys Gly Phe Glu Gly Phe Leu Gly Phe Leu Lys Glu Gly His Ala
130                 135                 140

His Tyr Glu Leu Ser Met Val His Val Leu His Arg Asn Phe Thr Ser
145                 150                 155                 160

Leu Leu Ser Met Val Arg Pro Ser Leu Ile Ile Gln Leu Arg Lys Leu
                165                 170                 175

His Pro Phe Val Ser Val Tyr Ser Arg Ala Thr Lys Tyr Phe Lys Thr
            180                 185                 190

Asp Arg Met Arg Arg Ala Phe Thr Phe Ala Ser Met Tyr Leu Gly Met
            195                 200                 205

Ser Pro Phe Asp Ala Leu Gly Ala Tyr Asn Leu Leu Gln Tyr Thr Glu
210                 215                 220

His Cys Glu Gly Ile Leu Tyr Pro Leu Gly Gly Phe Gly Arg Ile Pro
225                 230                 235                 240

Gln Thr Leu Gln Lys Leu Ala Glu Lys Ser Gly Ala Lys Phe Arg Phe
                245                 250                 255

Asn Ser Pro Val Lys Arg Val Thr Val Glu Asn Gly Thr Ala Lys Gly
            260                 265                 270

Val Glu Leu Glu Ser Gly Glu Lys Leu Lys Ala Glu Ile Val Leu Val
            275                 280                 285

Asn Ala Asp Leu Val Trp Ser Met Ala His Leu Tyr Glu Glu Thr Ser
290                 295                 300

Tyr Ser Lys Arg Leu Glu Glu Arg Pro Val Ser Cys Ser Ser Ile Ser
305                 310                 315                 320

Phe Tyr Trp Ser Met Asn Arg Lys Ile Pro Gln Leu Asp Ser His Thr
                325                 330                 335

Ile Phe Leu Ala Glu Glu Tyr Arg Glu Ser Phe Asp Ser Ile Phe Arg
            340                 345                 350

Glu His Arg Ile Pro His Glu Pro Ser Phe Tyr Val Asn Val Pro Ser
            355                 360                 365

Arg His Asp Pro Ser Ala Ala Pro Ala Asp Lys Asp Ala Val Ile Val
            370                 375                 380

Leu Val Pro Val Gly His Ile Ser Ala Ala Leu Pro Ser Ser Ser Asp
385                 390                 395                 400

Trp Asp Lys Val Val Glu Asp Thr Arg Asn Lys Ile Ile Gly Glu Ile
```

```
                   405                 410                 415
Glu Arg Arg Leu Asp Ile Lys Asp Leu Arg Gly Cys Ile Glu His Glu
            420                 425                 430

Thr Ile Asn Thr Pro Ile Thr Trp Gly Glu Lys Phe Asn Leu His Arg
            435                 440                 445

Gly Ser Ile Leu Gly Leu Ser His Asp Phe Phe Asn Val Leu Ser Phe
450                 455                 460

Arg Pro Lys Thr Arg His Pro Ser Val Lys Asn Ala Tyr Phe Val Gly
465                 470                 475                 480

Ala Ser Ala His Pro Gly Thr Gly Val Pro Ile Val Leu Ala Gly Ala
                485                 490                 495

Arg Leu Val Ala Thr Gln Ile Leu Asn Asp Leu Gly Met Pro Ile Pro
            500                 505                 510

Ser Arg Trp Asn Val Ser Ser Ser Glu Leu Ala Thr His Lys Thr Ile
            515                 520                 525

Arg Asp Ala Ala Gly Gly Phe Thr Leu Leu Ser Val Leu Phe Gly Leu
            530                 535                 540

Ile Ala Leu Leu Val Met Tyr Leu Arg Gly
545                 550

<210> SEQ ID NO 3
<211> LENGTH: 1916
<212> TYPE: DNA
<213> ORGANISM: Rhodosporidium toruloides
<220> FEATURE:
<221> NAME/KEY: CDS
<222> LOCATION: (78)..(1916)

<400> SEQUENCE: 3
gggctgttct cgctattctc gagggggtcgt cctggggctg tctgtgactt gctatcgact      60
gctagactcg cgctcgc atg ggc gga ctg gac tac tgg ctc gtc cac ctc        110
                   Met Gly Gly Leu Asp Tyr Trp Leu Val His Leu
                     1               5                  10 cgc tgg act atc ccg cca gcg cta gtc ctc tgg agc acc ttc aga aag      158
Arg Trp Thr Ile Pro Pro Ala Leu Val Leu Trp Ser Thr Phe Arg Lys
            15                  20                  25 ctt agg aca cgg cgc gat gtc tac aag acg ctc ttc ctc atc acc atc      206
Leu Arg Thr Arg Arg Asp Val Tyr Lys Thr Leu Phe Leu Ile Thr Ile
        30                  35                  40 gca gta acg gcg acg att ccc tgg gac tcg tac ctc atc cgg cac agg      254
Ala Val Thr Ala Thr Ile Pro Trp Asp Ser Tyr Leu Ile Arg His Arg
    45                  50                  55 atc tgg tca tac ccc gag tca tcc gtc gtc ggg ccg acc ctc ttc gcg      302
Ile Trp Ser Tyr Pro Glu Ser Ser Val Val Gly Pro Thr Leu Phe Ala
60                  65                  70                  75 ata ccc tac gaa gag atc ttc ttc ttc ttc gtc caa acc tac atc acc      350
Ile Pro Tyr Glu Glu Ile Phe Phe Phe Phe Val Gln Thr Tyr Ile Thr
                80                  85                  90 gcg acc gtc tac gcc ctc ttc agc cgc cca gtc gtc cac gcc gtc ctc      398
Ala Thr Val Tyr Ala Leu Phe Ser Arg Pro Val Val His Ala Val Leu
                95                 100                 105 ctc cct cgg aaa cct agc gac gga cga gca gcg agg tgg att gga acg      446
Leu Pro Arg Lys Pro Ser Asp Gly Arg Ala Ala Arg Trp Ile Gly Thr
            110                 115                 120 gcg gcg ttc ttg ggc atc ttt gcg ctc gcg tgg gca aag ttg gag gag      494
Ala Ala Phe Leu Gly Ile Phe Ala Leu Ala Trp Ala Lys Leu Glu Glu
        125                 130                 135 gga gga gag ggg acg tac ctc gcg ttg att gtt gga tgg gtg gcg ccg      542
```

```
Gly Gly Glu Gly Thr Tyr Leu Ala Leu Ile Val Gly Trp Val Ala Pro
140             145                 150                 155 ttc ctt gcg ctg ctt tgg ttc att gcc tca acc cac atc ctc gcc atg    590
Phe Leu Ala Leu Leu Trp Phe Ile Ala Ser Thr His Ile Leu Ala Met
                160                 165                 170 ccc cgc tgg gct gtc ggt ctc ccc atc ctc cta ccg acg ctc tac ctg    638
Pro Arg Trp Ala Val Gly Leu Pro Ile Leu Leu Pro Thr Leu Tyr Leu
        175                 180                 185 tgg gag tgc gac gcg cga gct ctg caa cgc ggg act tgg gtc atc gag    686
Trp Glu Cys Asp Ala Arg Ala Leu Gln Arg Gly Thr Trp Val Ile Glu
        190                 195                 200 aag ggc acg aag ctg ggc ttg gct ttc cgc ggt ctc gag att gag gag    734
Lys Gly Thr Lys Leu Gly Leu Ala Phe Arg Gly Leu Glu Ile Glu Glu
205                 210                 215 gcc gtc ttc ttc ctc ttg acg aac gtc atg atc gtc ttc ggc ctg gtc    782
Ala Val Phe Phe Leu Leu Thr Asn Val Met Ile Val Phe Gly Leu Val
220                 225                 230                 235 gcc tgc gac tac tgc ctc gca gtt cac gac ctc cgc tcc tac gac aag    830
Ala Cys Asp Tyr Cys Leu Ala Val His Asp Leu Arg Ser Tyr Asp Lys
        240                 245                 250 cgc acc tca tcc gtc ttc cca ccc ctg cgc gac ttc ctc ccg atc ctc    878
Arg Thr Ser Ser Val Phe Pro Pro Leu Arg Asp Phe Leu Pro Ile Leu
        255                 260                 265 ctc aac tcg ccc gac gcc gca cag cga caa cgc atc gag gac ttg cag    926
Leu Asn Ser Pro Asp Ala Ala Gln Arg Gln Arg Ile Glu Asp Leu Gln
        270                 275                 280 gcg gct atc gag atc ttg tcg att cac tcg aag agc ttc tcg acg gcg    974
Ala Ala Ile Glu Ile Leu Ser Ile His Ser Lys Ser Phe Ser Thr Ala
285                 290                 295 agt cag gtg ttt gag ggc agg ttg agg ctg gac ctc ctc tcg ctc tac    1022
Ser Gln Val Phe Glu Gly Arg Leu Arg Leu Asp Leu Leu Ser Leu Tyr
300                 305                 310                 315 gcc tgg tgc cga gtc tgc gac gac ctg atc gac aac gcc tcg aca gtc    1070
Ala Trp Cys Arg Val Cys Asp Asp Leu Ile Asp Asn Ala Ser Thr Val
        320                 325                 330 gca gca gcc gaa tcc aac atc gac atg att tcg ggc tgc ctc gac ctc    1118
Ala Ala Ala Glu Ser Asn Ile Asp Met Ile Ser Gly Cys Leu Asp Leu
            335                 340                 345 ctc tac cct ccc tcc tcc tcc acg ccc acc tct ctc ccc gtc cgc gtt    1166
Leu Tyr Pro Pro Ser Ser Ser Thr Pro Thr Ser Leu Pro Val Arg Val
        350                 355                 360 tcg aac aag cag atc gag gcg gcc ttg ccc ggc ttg agc gag ccc gaa    1214
Ser Asn Lys Gln Ile Glu Ala Ala Leu Pro Gly Leu Ser Glu Pro Glu
365                 370                 375 cga ggc gca ttc cgc ctc ctc agc ctt ctc cct att gcc cgc ccg ccg    1262
Arg Gly Ala Phe Arg Leu Leu Ser Leu Leu Pro Ile Ala Arg Pro Pro
380                 385                 390                 395 ctt aac gaa ctc ctc gac ggc ttc cgc acc gac ctc tcc ttc ctc gct    1310
Leu Asn Glu Leu Leu Asp Gly Phe Arg Thr Asp Leu Ser Phe Leu Ala
        400                 405                 410 ctc tcc gac tcg aag ggt gtc aag acg aac ggc agc gca aac ggt aac    1358
Leu Ser Asp Ser Lys Gly Val Lys Thr Asn Gly Ser Ala Asn Gly Asn
            415                 420                 425 ggg aac ggc ata tcg agt atc tcc gcc gag ttg ccc atc aag acc gac    1406
Gly Asn Gly Ile Ser Ser Ile Ser Ala Glu Leu Pro Ile Lys Thr Asp
            430                 435                 440 tcg gat ctc ctc gtc tac gcc aat aac gtc gcc tcg tcc gtc gcc gat    1454
Ser Asp Leu Leu Val Tyr Ala Asn Asn Val Ala Ser Ser Val Ala Asp
445                 450                 455
```

```
ctc tgc gtc caa ctc gtc tgg gca cac tgc acg cct tac tcg cgc aca    1502
Leu Cys Val Gln Leu Val Trp Ala His Cys Thr Pro Tyr Ser Arg Thr
460             465                 470                 475 ccc gct caa tca gtc ccg cgc gac ccg acc ctc tca gaa gcg gag aac    1550
Pro Ala Gln Ser Val Pro Arg Asp Pro Thr Leu Ser Glu Ala Glu Asn
                480                 485                 490 gca cat gtt ctc gct gcg gcg agg gag atg gga cag gct ctt cag ctc    1598
Ala His Val Leu Ala Ala Ala Arg Glu Met Gly Gln Ala Leu Gln Leu
        495                 500                 505 gtc aat atc gcg cgg gac gta ccg gcg gat ctg aag att ggg cgg atc    1646
Val Asn Ile Ala Arg Asp Val Pro Ala Asp Leu Lys Ile Gly Arg Ile
            510                 515                 520 tac ctc cct ggt cgc ggg ctc gac acg cct gtg ccc gag ttg acg gcg    1694
Tyr Leu Pro Gly Arg Gly Leu Asp Thr Pro Val Pro Glu Leu Thr Ala
525                 530                 535 gat agg cgg gcc cta ctt gct cgt gcg aac gag atg gct gca cag agt    1742
Asp Arg Arg Ala Leu Leu Ala Arg Ala Asn Glu Met Ala Ala Gln Ser
540                 545                 550                 555 aag gat gcg ata gag aag ttg ccg caa gag gcg aga gga ggg atc agg    1790
Lys Asp Ala Ile Glu Lys Leu Pro Gln Glu Ala Arg Gly Gly Ile Arg
                560                 565                 570 gcg gcg tgt ttg gtt tat ctc agc att ggg gac gcg gtc ggg agg gcc    1838
Ala Ala Cys Leu Val Tyr Leu Ser Ile Gly Asp Ala Val Gly Arg Ala
        575                 580                 585 ttg gac gag ggg agg gtc atg gag cgc gcg agg gtg tcc aag ggg gcg    1886
Leu Asp Glu Gly Arg Val Met Glu Arg Ala Arg Val Ser Lys Gly Ala
            590                 595                 600 agg gcg cgc aaa gcg tgg cag gcg ttg tga                            1916
Arg Ala Arg Lys Ala Trp Gln Ala Leu
605                 610
```

<210> SEQ ID NO 4
<211> LENGTH: 612
<212> TYPE: PRT
<213> ORGANISM: Rhodosporidium toruloides

<400> SEQUENCE: 4

```
Met Gly Gly Leu Asp Tyr Trp Leu Val His Leu Arg Trp Thr Ile Pro
1               5                   10                  15

Pro Ala Leu Val Leu Trp Ser Thr Phe Arg Lys Leu Arg Thr Arg Arg
            20                  25                  30

Asp Val Tyr Lys Thr Leu Phe Leu Ile Thr Ile Ala Val Thr Ala Thr
        35                  40                  45

Ile Pro Trp Asp Ser Tyr Leu Ile Arg His Arg Ile Trp Ser Tyr Pro
    50                  55                  60

Glu Ser Ser Val Val Gly Pro Thr Leu Phe Ala Ile Pro Tyr Glu Glu
65                  70                  75                  80

Ile Phe Phe Phe Val Gln Thr Tyr Ile Thr Ala Thr Val Tyr Ala
                85                  90                  95

Leu Phe Ser Arg Pro Val Val His Ala Val Leu Leu Pro Arg Lys Pro
            100                 105                 110

Ser Asp Gly Arg Ala Ala Arg Trp Ile Gly Thr Ala Ala Phe Leu Gly
        115                 120                 125

Ile Phe Ala Leu Ala Trp Ala Lys Leu Glu Glu Gly Gly Glu Gly Thr
    130                 135                 140

Tyr Leu Ala Leu Ile Val Gly Trp Val Ala Pro Phe Leu Ala Leu Leu
145                 150                 155                 160

Trp Phe Ile Ala Ser Thr His Ile Leu Ala Met Pro Arg Trp Ala Val
```

```
                165                 170                 175
Gly Leu Pro Ile Leu Pro Thr Leu Tyr Leu Trp Glu Cys Asp Ala
            180                 185                 190
Arg Ala Leu Gln Arg Gly Thr Trp Val Ile Glu Lys Gly Thr Lys Leu
        195                 200                 205
Gly Leu Ala Phe Arg Gly Leu Glu Ile Glu Glu Ala Val Phe Phe Leu
    210                 215                 220
Leu Thr Asn Val Met Ile Val Phe Gly Leu Val Ala Cys Asp Tyr Cys
225                 230                 235                 240
Leu Ala Val His Asp Leu Arg Ser Tyr Asp Lys Arg Thr Ser Ser Val
                245                 250                 255
Phe Pro Pro Leu Arg Asp Phe Leu Pro Ile Leu Leu Asn Ser Pro Asp
            260                 265                 270
Ala Ala Gln Arg Gln Arg Ile Glu Asp Leu Gln Ala Ala Ile Glu Ile
        275                 280                 285
Leu Ser Ile His Ser Lys Ser Phe Ser Thr Ala Ser Gln Val Phe Glu
    290                 295                 300
Gly Arg Leu Arg Leu Asp Leu Leu Ser Leu Tyr Ala Trp Cys Arg Val
305                 310                 315                 320
Cys Asp Asp Leu Ile Asp Asn Ala Ser Thr Val Ala Ala Glu Ser
                325                 330                 335
Asn Ile Asp Met Ile Ser Gly Cys Leu Asp Leu Leu Tyr Pro Pro Ser
            340                 345                 350
Ser Ser Thr Pro Thr Ser Leu Pro Val Arg Val Ser Asn Lys Gln Ile
        355                 360                 365
Glu Ala Ala Leu Pro Gly Leu Ser Glu Pro Glu Arg Gly Ala Phe Arg
    370                 375                 380
Leu Leu Ser Leu Leu Pro Ile Ala Arg Pro Pro Leu Asn Glu Leu Leu
385                 390                 395                 400
Asp Gly Phe Arg Thr Asp Leu Ser Phe Leu Ala Leu Ser Asp Ser Lys
                405                 410                 415
Gly Val Lys Thr Asn Gly Ser Ala Asn Gly Asn Gly Asn Gly Ile Ser
            420                 425                 430
Ser Ile Ser Ala Glu Leu Pro Ile Lys Thr Asp Ser Asp Leu Leu Val
        435                 440                 445
Tyr Ala Asn Asn Val Ala Ser Ser Val Ala Asp Leu Cys Val Gln Leu
    450                 455                 460
Val Trp Ala His Cys Thr Pro Tyr Ser Arg Thr Pro Ala Gln Ser Val
465                 470                 475                 480
Pro Arg Asp Pro Thr Leu Ser Glu Ala Glu Asn Ala His Val Leu Ala
                485                 490                 495
Ala Ala Arg Glu Met Gly Gln Ala Leu Gln Leu Val Asn Ile Ala Arg
            500                 505                 510
Asp Val Pro Ala Asp Leu Lys Ile Gly Arg Ile Tyr Leu Pro Gly Arg
        515                 520                 525
Gly Leu Asp Thr Pro Val Pro Glu Leu Thr Ala Asp Arg Arg Ala Leu
    530                 535                 540
Leu Ala Arg Ala Asn Glu Met Ala Ala Gln Ser Lys Asp Ala Ile Glu
545                 550                 555                 560
Lys Leu Pro Gln Glu Ala Arg Gly Gly Ile Arg Ala Ala Cys Leu Val
                565                 570                 575
Tyr Leu Ser Ile Gly Asp Ala Val Gly Arg Ala Leu Asp Glu Gly Arg
            580                 585                 590
```

```
Val Met Glu Arg Ala Arg Val Ser Lys Gly Ala Arg Ala Arg Lys Ala
    595                 600                 605

Trp Gln Ala Leu
    610

<210> SEQ ID NO 5
<211> LENGTH: 1121
<212> TYPE: DNA
<213> ORGANISM: Rhodosporidium toruloides
<220> FEATURE:
<221> NAME/KEY: CDS
<222> LOCATION: (42)..(1121)

<400> SEQUENCE: 5
actcgctccc gctgctctcg ctcgctgctg cttgtctgag g atg tcg ctg gat tgg      56
                                             Met Ser Leu Asp Trp
                                              1               5 tac gac aac ttt atc gac aag gtg cag ggc acg ccg tcg tgg cag ccc      104
Tyr Asp Asn Phe Ile Asp Lys Val Gln Gly Thr Pro Ser Trp Gln Pro
             10                  15                  20 gcg cag gag cag gtc ctg aca gag ccg tac acc tac ctc gcc tcg atc      152
Ala Gln Glu Gln Val Leu Thr Glu Pro Tyr Thr Tyr Leu Ala Ser Ile
         25                  30                  35 ccg ggc aag gag gtg cgc tcg gcg ctc atc gcg gcg ttc aac cag tgg      200
Pro Gly Lys Glu Val Arg Ser Ala Leu Ile Ala Ala Phe Asn Gln Trp
     40                  45                  50 atg ggt gtc gca gac gtc gat ctc gag att gtc aag aaa gtc gtc ggg      248
Met Gly Val Ala Asp Val Asp Leu Glu Ile Val Lys Lys Val Val Gly
 55                  60                  65 atg ctg cac acg gcc agc ctg ctg atg gac gac gtc gag gac gac tcg      296
Met Leu His Thr Ala Ser Leu Leu Met Asp Asp Val Glu Asp Asp Ser
 70                  75                  80                  85 cac ctc cgt cga ggc atg cct gtc gca cac aag atc tac gga atc ccg      344
His Leu Arg Arg Gly Met Pro Val Ala His Lys Ile Tyr Gly Ile Pro
                 90                  95                 100 cag acg atc aac tcg gcc aac tat gtc tac ttt ctc gcg ttt caa gaa      392
Gln Thr Ile Asn Ser Ala Asn Tyr Val Tyr Phe Leu Ala Phe Gln Glu
            105                 110                 115 ctc cag cgg ata cac ccg cgg cca ggc atc aag gtc gaa gag atg gtc      440
Leu Gln Arg Ile His Pro Arg Pro Gly Ile Lys Val Glu Glu Met Val
        120                 125                 130 act gaa gag cta ttg aac ctg cat cgc gga caa ggg atg gac cta ttc      488
Thr Glu Glu Leu Leu Asn Leu His Arg Gly Gln Gly Met Asp Leu Phe
    135                 140                 145 tgg cgc gag aac ctg atc tgt ccg aca gaa ccc gag tac atc gac atg      536
Trp Arg Glu Asn Leu Ile Cys Pro Thr Glu Pro Glu Tyr Ile Asp Met
150                 155                 160                 165 gtc aac aac aag acg gga gga ctg ttc cgc att gcg atc aag ttg atg      584
Val Asn Asn Lys Thr Gly Gly Leu Phe Arg Ile Ala Ile Lys Leu Met
                170                 175                 180 atg gcc gct tcg cct gct cca cca cgg gat tac gtc ccg ctc gcc aac      632
Met Ala Ala Ser Pro Ala Pro Pro Arg Asp Tyr Val Pro Leu Ala Asn
            185                 190                 195 ctg atc ggc atc atc ttc cag atc cgc gac gac tac gtg aac ctg caa      680
Leu Ile Gly Ile Ile Phe Gln Ile Arg Asp Asp Tyr Val Asn Leu Gln
        200                 205                 210 tcc gtc gag tac gca aac aat aag ggc tac tgc gaa gac ttc tcc gaa      728
Ser Val Glu Tyr Ala Asn Asn Lys Gly Tyr Cys Glu Asp Phe Ser Glu
    215                 220                 225 ggc aaa ttc tcc ttc ccc atc gtc cac tcg atc cgc tcc gac acc tcg      776
```

```
Gly Lys Phe Ser Phe Pro Ile Val His Ser Ile Arg Ser Asp Thr Ser
230                 235                 240                 245 aac cgc caa atc ctc aac atc ctg cgc gag cgg cct tcc tct ccc ggt      824
Asn Arg Gln Ile Leu Asn Ile Leu Arg Glu Arg Pro Ser Ser Pro Gly
                250                 255                 260 ccg aaa gag tac gcc gtc agc tac atg gag aca cgg acg ggc tcg ttc      872
Pro Lys Glu Tyr Ala Val Ser Tyr Met Glu Thr Arg Thr Gly Ser Phe
                265                 270                 275 gcg tat acg cgc gag gtg ttg cgc aag ttg acg cag cag gcg agg gac      920
Ala Tyr Thr Arg Glu Val Leu Arg Lys Leu Thr Gln Gln Ala Arg Asp
                280                 285                 290 gag gtt gcg cgg ctg gga ggg aac agg ggc gtc gag gcg att ctc gac      968
Glu Val Ala Arg Leu Gly Gly Asn Arg Gly Val Glu Ala Ile Leu Asp
295                 300                 305 aag ctt gtg ctg gag gaa ccg cag gtg aag gtc aat ggc gtc gag ggc     1016
Lys Leu Val Leu Glu Glu Pro Gln Val Lys Val Asn Gly Val Glu Gly
310                 315                 320                 325 gag gcg atg gag agg aag ctt gag gag gtc gtc aag agc aaa ccg gtc     1064
Glu Ala Met Glu Arg Lys Leu Glu Glu Val Val Lys Ser Lys Pro Val
                330                 335                 340 aag gcg gtg acg aac ggc gtc aac ggc gtc cat gcg cac gcg ctc ccc     1112
Lys Ala Val Thr Asn Gly Val Asn Gly Val His Ala His Ala Leu Pro
                345                 350                 355 aaa gcc tga                                                         1121
Lys Ala <210> SEQ ID NO 6
<211> LENGTH: 359
<212> TYPE: PRT
<213> ORGANISM: Rhodosporidium toruloides

<400> SEQUENCE: 6

Met Ser Leu Asp Trp Tyr Asp Asn Phe Ile Asp Lys Val Gln Gly Thr
1               5                   10                  15

Pro Ser Trp Gln Pro Ala Gln Glu Gln Val Leu Thr Glu Pro Tyr Thr
            20                  25                  30

Tyr Leu Ala Ser Ile Pro Gly Lys Glu Val Arg Ser Ala Leu Ile Ala
        35                  40                  45

Ala Phe Asn Gln Trp Met Gly Val Ala Asp Val Asp Leu Glu Ile Val
    50                  55                  60

Lys Lys Val Val Gly Met Leu His Thr Ala Ser Leu Leu Met Asp Asp
65                  70                  75                  80

Val Glu Asp Asp Ser His Leu Arg Arg Gly Met Pro Val Ala His Lys
                85                  90                  95

Ile Tyr Gly Ile Pro Gln Thr Ile Asn Ser Ala Asn Tyr Val Tyr Phe
            100                 105                 110

Leu Ala Phe Gln Glu Leu Gln Arg Ile His Pro Arg Pro Gly Ile Lys
        115                 120                 125

Val Glu Glu Met Val Thr Glu Glu Leu Leu Asn Leu His Arg Gly Gln
    130                 135                 140

Gly Met Asp Leu Phe Trp Arg Glu Asn Leu Ile Cys Pro Thr Glu Pro
145                 150                 155                 160

Glu Tyr Ile Asp Met Val Asn Asn Lys Thr Gly Gly Leu Phe Arg Ile
                165                 170                 175

Ala Ile Lys Leu Met Met Ala Ala Ser Pro Ala Pro Arg Asp Tyr
            180                 185                 190

Val Pro Leu Ala Asn Leu Ile Gly Ile Ile Phe Gln Ile Arg Asp Asp
        195                 200                 205
```

```
Tyr Val Asn Leu Gln Ser Val Glu Tyr Ala Asn Asn Lys Gly Tyr Cys
            210                 215                 220

Glu Asp Phe Ser Glu Gly Lys Phe Ser Phe Pro Ile Val His Ser Ile
225                 230                 235                 240

Arg Ser Asp Thr Ser Asn Arg Gln Ile Leu Asn Ile Leu Arg Glu Arg
                245                 250                 255

Pro Ser Ser Pro Gly Pro Lys Glu Tyr Ala Val Ser Tyr Met Glu Thr
            260                 265                 270

Arg Thr Gly Ser Phe Ala Tyr Thr Arg Glu Val Leu Arg Lys Leu Thr
            275                 280                 285

Gln Gln Ala Arg Asp Glu Val Ala Arg Leu Gly Gly Asn Arg Gly Val
            290                 295                 300

Glu Ala Ile Leu Asp Lys Leu Val Leu Glu Glu Pro Gln Val Lys Val
305                 310                 315                 320

Asn Gly Val Glu Gly Glu Ala Met Glu Arg Lys Leu Glu Glu Val Val
                325                 330                 335

Lys Ser Lys Pro Val Lys Ala Val Thr Asn Gly Val Asn Gly Val His
            340                 345                 350

Ala His Ala Leu Pro Lys Ala
            355
```

<210> SEQ ID NO 7
<211> LENGTH: 2430
<212> TYPE: DNA
<213> ORGANISM: Rhodosporidium toruloides

<400> SEQUENCE: 7

```
accactcgct agtgaagcaa tggcagctgc gaacggacac ggcaagggaa agccctcggt     60
gctcatcgtc ggagcgggcg tcggaggcac tgcgtccgcc gctcgcctcg cccagtccgg    120
gttcgacgtg acaggtgcgc acactcgtct cctgcgccgt cctgcgtcga tcggggacg    180
tgggagctat gagggtgact gtcgagaggt actgacgagt tcgcctcgtc gacagtcctc    240
gagaagaacg actttgccgg cggacgatgc tccctcttca ccgatccgac caagtccttc    300
cgcttcgacc agggcccgag cctgttcctc atcccgcgac tgttcgacga gaccttcagc    360
gacctcggga cgagccttga gaacgagggc atcaagcttg tcaagtgcga gccaaactac    420
cggatcgtct tccccgacaa ggaggtcgtc gagatgagca gcgacttgac gaggatgaag    480
aagcaggtcg agcggtggga gggagagaag ggctttgaag ggtgagtggc gggcgaagtt    540
gaagcgagac cacgagcgga gatgccccct cgctcgtgtt ccctcgccgc ttttcttcca    600
gttaactgac gttcatgttc gatacagatt tctcggcttc ctgaaggagg acatgcgcca    660
ctacgagctg tcgatggttc acgtcctcca ccgcaacttc acctcgctcc tctcgatggt    720
ccgcccgtct ctgatcatcc agctccgcaa gctccatccc tttgtctctg tcgtacgtca    780
cctcatcaag gctgatacga ctcgctggga acgcaggatt gctgatgagc gtcgcatcga    840
ctcagtattc gcgcgcgacc aagtacttca agacggaccg catgcggaga gcgttcacct    900
ttgcgtccat gtaccttgtg agttggagca cattacaata cgagcgccag ctatggcgcc    960
tcaattgctc gccaagatcc tcctccgctg acccgcacct cctctttcgc agggcatgtc   1020
tcccttcgac gctctcggcg cctacaacct cctccagtac accgagcact gcgaaggcat   1080
cctctaccct ctcggtggtt tcggtcgcat ccctcaaacc ctccaaaaac tcgccgaaaa   1140
gagcggcgcc aagttccgct tcaacagtcc cgtcaagcgc gtcacggtgg agaatggcac   1200
```

-continued

```
ggccaagggt gttgaactcg agagtggcga gaagttgaag gccgagatcg tcctcgtcaa      1260
tgcggatttg gtgtggagta tggcgcattt gtacgaggag acgagctact cgaagaggct      1320
cgaggagcgc cccgtcagct gctcgtccat ctcgttttac tggtcgatga accggtgcgt      1380
tgagattgtc actcttcact tatctcagag cggtggatcc tgacgctgtt cgagccattc      1440
cacagcaaga taccccagct cgactcgcat accatcttcc tcgcagagga gtaccgagag      1500
tgagcacgag atcgctgcgg tactcgacac aagattgact gctgacggat acgcactgtc      1560
caggtccttc gactcgatct tccgcgaaca ccgtatcccg catgagcctt ccttctacgt      1620
caacgtcccc agccgtcacg acccttcgtg cgttttgctc acctcgttag ctcgccctcg      1680
tcgctcactc attgtccgct cgcagtgccg ctcccgccga caaagacgcc gtcatcgtcc      1740
tcgtccccgt cgggcacatt tccgccgccc tcccctcctc ttccgactgg gacaaagtgg      1800
tcgaagacac gcgtaacaag attatcggcg agatcgagcg ccgactcgac atcaaggacc      1860
tccgaggctg catcgagcac gagacgatca acacgcctat cacttggggc gagaagttca      1920
acttgcaccg cggcagtatc cttggactca gtcacgactt cttgtgagtc tcgcgcgcta      1980
gtctctggtc ctgctcgtcg acgttagcgc tgaccttccc aatctttcgt ttctctcagc      2040
aacgtcctct ctttccgccc caagaccgc cacccgagcg tcaagaacgc ttacttcgtc      2100
ggcgcgtctg cgcacccggg aactgggtga gtcacggtgg tcttcgctcg tctcgcttgc      2160
cgttgctccc tgggcagcgc cgcgcgtgtg ggcggaagcc ttgtgactga ctctcgtcgt      2220
cgttgcagcg tccccatcgt cctcgccggc gcccgcctcg tcgcaaccca gatcctcaac      2280
gacctcggca tgcccatccc ctcgcgctgg aacgtctcct cctccgaact cgcgacgcac      2340
aagacgatcc gcgatgcggc gggagggttc accctcctct cggtgttgtt tgggctgatc      2400
gcgttgttgg tcatgtatct gcgcggatga                                       2430
```

<210> SEQ ID NO 8
<211> LENGTH: 2334
<212> TYPE: DNA
<213> ORGANISM: Rhodosporidium toruloides

<400> SEQUENCE: 8

```
gggctgttct cgctattctc gaggggtcgt cctggggctg tctgtgactt gctatcgact       60
gctagactcg cgctcgcatg gcggactgg actactggct cgtgtgcgtc cacctcgctc       120
ccgttcactc gcatcctccg gactcaccct cgtgttgctc gtaacgcgcg acagccacct      180
ccgctggact atcccgccag cgctagtcct ctggagcacc ttcagaaagc ttaggacacg      240
gcgcgatgtc tacaagacgc tcttcctcat caccgtgcgt cctcaccgct tcctccgtcg      300
gctcgatgct ccaatcgcca actgacctct gctcgtcccg cagatcgcag taacggttcg      360
tgcagctcat gtaaaccgga agacgagaga ggctgaccga aagacgcgca ggcgacgatt      420
ccctgggact cgtacctcat ccggcacagg gtgcgccaag tcttgctctg tatccccaaa      480
accgccgtct aacgctcgcg ccggacagat ctggtcatac cccgagtcat ccgtcgtcgg      540
gccgacccctc ttcgcgatac cctacgaaga gatcttcttc ttcttcgtcc aaacctacat      600
caccgcgacc gtctacgccc tcttcagccg cccagtcgtc cacgccgtcc tcctccctcg      660
gaaacctagc gacggacgag cagcgaggtg gattggaacg gcggcgttct ggggcatctt      720
tgcgctcgcg tgggcaaagt tggaggaggg aggagagggg acgtacctcg cgttgattgt      780
tggatggggtg gcgccgttcc ttgcgctgct ttggtgcgtt cagcgagttt ccggacgagg      840
aggatgactg acttgtgtcg cgcaggttca ttgcctcaac ccacatcctc gccatgcccc      900
```

```
gctgggctgt cggtctcccc atcctcctac cgacgctcta cctgtgggag tgcgacgcgc    960
gagctctgca acgcgggact tgggtcatcg agaagggcac gaagctgggc ttggctttcc   1020
gcggtctcga gattgagtgc gtcctgccgt ctttcgtctt tctccgcgct tgctgactgt   1080
acgtgcttca cagggaggcc gtcttcttcc tcttgacgaa cgtcatgatc gtcttcggcc   1140
tggtcgcctg cgactactgc ctcgcagttc acgacctccg ctcctacgac aagcgcacct   1200
catccgtctt cccaccsctg cgcgacttcc tcccgatcct cctcaactcg cccgacgccg   1260
cacagcgaca acgcatcgag gacttgcagg cggctatcga gatcttgtcg attcactcga   1320
agagcttctc gacggcgagt caggtgtttg agggcaggtt gaggctggac ctcctctcgc   1380
tgtgagtgcg gctccttccg aagcaaagac tcgagctgac cttgagagta tcgcagctac   1440
gcctggtgcc gagtctgcga cgacctgatc gacaacgcct cgacagtcgc agcagccgaa   1500
tccaacatcg acatgatttc gggctgcctc gacctcctct accctccctc ctcctccacg   1560
cccacctctc tccccgtccg cgtttcgaac aagcagatcg aggcggcctt gcccggcttg   1620
agcgagcccg aacgaggcgc attccgcctc ctcagccttc tccctattgc ccgcccgccg   1680
cttaacgaac tcctcgacgg cttccgcacc gacctctcct tcctcgctct ctccgactcg   1740
aagggtgtca agacgaacgg cagcgcaaac ggtaacggga acggcatatc gagtatctcc   1800
gccgagttgc ccatcaagac cgactcggat ctcctcgtct acgccaataa cgtcgcctcg   1860
tccgtcgccg atctctgcgt ccaactcgtc tgggcacact gcacgcctta ctcgcgcaca   1920
cccgctcaat cagtcccgcg cgacccgacc ctctcagaag cggagaacgc acatgttctc   1980
gctgcggcga gggagatggg acaggctctt cagctcgtca atatcgcgcg ggacgtaccg   2040
gcggatctga agattgggcg gatctacctc cctggtcgcg gctcgacac gcctgtgccc   2100
gagttgacgg cggataggcg ggccctactt gctcgtgcga acgagatggc tgcacagagt   2160
aaggatgcga tagagaagtt gccgcaagag gcgagaggag ggatcagggc ggcgtgtttg   2220
gtttatctca gcattgggga cgcggtcggg agggccttgg acgaggggag ggtcatggag   2280
cgcgcgaggg tgtccaaggg ggcgagggcg cgcaaagcgt ggcaggcgtt gtga          2334
```

<210> SEQ ID NO 9
<211> LENGTH: 1546
<212> TYPE: DNA
<213> ORGANISM: Rhodosporidium toruloides

<400> SEQUENCE: 9

```
actcgctccc gctgctctcg ctcgctgctg cttgtctgag gatgtcgctg gattggtacg     60
acaactttat cgacaaggtg cagggcacgc cgtcgtggca gcccgcgcag gagcaggtgc    120
gctcgcccgg caccgccgtc gcctccccac atcctcacga gtcgtcgaag ccagcgctga    180
cacgctcgag gacaggtcct gacagagccg tacacctacc tcgcctcgat cccgggcaag    240
gaggtgcgct cggcgctcat cgcggcgttc aaccagtgga tgggtgtcgc agacgtcgat    300
ctcgagattg tcaagaaagt cgtcgggatg ctgcacacgg ccagcctgct gtgcgctatc    360
gagacgccct cgctgtccag ctaccccggg tgctcacgat ccgcgtcgat tccccgcagga   420
tggacgacgt cgaggacgac tcgcacctcc gtcgaggcat gcctggtcag tccccgatct    480
ccgagccgcc tccgtcgca gagactgatc ccgtgtaccg tcgcacagtc gcacacaaga     540
tctacggaat cccgcagacg atcaactcgg ccaactatgt ctactttctc gcgtttcaag    600
aactccagcg gatacacccg cggccaggca tcaaggtcga agagatggtc actggtgggt    660
```

```
ccgccttttc ttgactaaag cttcgggtgc taacgcagtc cccgcagaag agctattgaa    720
cctgcatcgc ggacaaggga tggacctatt ctggcgcgag aacctgatct gtccgacaga    780
acccgagtac atcgacatgg tcaacaacag tgcgtcctgc gaggctgttc tatgcgattt    840
acgctgactc ggtcgcaatc gcagagacgg gaggactgtt ccgcattgcg atcaagttga    900
tgatggccgc ttcgcctgct ccaccacggt gcgctccctg cctcgacttg ctgggactcg    960
cagctgatga ttgcgttgca gggattacgt cccgctcgcc aacctgatcg gcatcatctt   1020
ccagatccgc gacgactacg tgaacctgca atccgtcgag gtgcgtttcg ctctcattat   1080
gggctgctcc aacgctaacg gatcggtcgc acagtacgca aacaataagg gctactgcga   1140
agacttctcc gaaggcaaat tctccttccc catcgtccac tcgatccgct ccgacacctc   1200
gaaccgccaa atcctcaaca tcctgcgcga gcggccttcc tctcccggtc cgaaagagta   1260
cgccgtcagc tacatggaga cacgacgggg ctcgttcgcg tatacgcgcg aggtgttgcg   1320
caagttgacg cagcaggcga gggacgaggt tgcgcggctg ggagggaaca ggggcgtcga   1380
ggcgattctc gacaagcttg tgctggagga accgcaggtg aagtcaatg gcgtcgaggg   1440 cgaggcgatg gagaggaagc ttgaggaggt cgtcaagagc aaaccggtca aggcggtgac   1500
gaacggcgtc aacggcgtcc atgcgcacgc gctccccaaa gcctga               1546

<210> SEQ ID NO 10
<211> LENGTH: 2079
<212> TYPE: DNA
<213> ORGANISM: Rhodosporidium toruloides

<400> SEQUENCE: 10
atggggacga agccccggca cacctacaag caggggaact acctccccgt gcgagaggag     60
cgcacgctcg aggagtgcgc ttgcgaaggt cagctcccgc aagagctcgt cggcgggtgc    120
gtttccgcgc cctttcctgc tcccatacag tgcttacagt gctcctacag gatgtacgtg    180
cggaatgggg gtgagcctgc gctggcagag ttgcgaggag acgactccgc agacggacct    240
gcctaccact gggtgcgttc ggcctcgtcc gcctgcgcat tctacacgag gagctgacac    300
ttgacgacga cagttcgacg gtgacggcat gctgacgggc gtgtacttca agcccgtccc    360
ctcctcctcg cccttcgacc cgaacccgcg tatcgccccg ctcttcgtca acaaatacgt    420
cctcaccgac gtcttcctcg cctgaaaagc gctcggcgtc acacatccca tcctacccctc    480 catcgccaca ctcctcggct caatctggtc cctccacctc atcctctact ccgtctttcg    540
cgccctcttc ctcgccttct gctccttctt caccgaatcg cctttgcgac atctctcagt    600
cgccaacacg tcggtcctgt ggcacgacgg acgggcgttg gcgagttgcg agagcgggcc    660
gttgacatgg gttacgctgc cggagctcga tacggtcggg ttctggagtc tggagggcga    720
caatggcgag aaggggctgc gagagcaggg tggcatgctc ggctggatga aggagtggac    780
gacggcgcat gtgagtcggc tgcttgcctt cgacagtcct cagagttgac cgtctctttg    840
cagccgaagc gcgacccgca caccggcgaa cttatgctct ccacatgtc gttcctcccg    900 ccctacctcc actactccgt catcccttcc actcacgctc ctcctccctc cgcccgttcc    960
gagaaggccg cacccactcc tcgcatcctc gccgcccccg ttcccatcgc cgcacctcgc   1020
atgatgcacg atatggccgc ctctcggacg cactcgatcc tcctcgacat gcccctctcg   1080
ctcgacccgc gcaatctcgc actcggcaag cccgtcatct cctacgaccc gtccaaaccc   1140
gctcgcttcg gcgtcttgcc tcgccacaaa ccgacactcg tcaagtggta catcgccccg   1200
gcgtgcataa tctttcacac cgctttcgcg tacgacgagc cccctcaac ttcccacgac   1260
```

```
gaggtcgagg cagtcaacct cgtctgctgc cgcctcaact ctccccgcct catctactcc    1320
gccggtaacc tcgtcctccc cgagtctcaa tccctcccag caggcgccaa agagtcctgc    1380
gagctctact actaccgctt ccctcttcc tcctccgcct ccgtcaccct cgaaccgtcg    1440
cacgccttcc cctcgccgc gattcccttc gagttcccga ccgtaccgca ggaccgcgcg    1500
gtcggcccgt cgaagtacgt ctatgggtgc tcggtgaagc acgggtcgtt cgatgcggcg    1560
cttgggtcgg cggcgaagat cgactgcctc gtcaaggtca acgtcgactt gctcgtccgg    1620
cagggcaaga agcgcaacga ggcgggcgag ggacagtcgg agcgaccggt cgacgagcga    1680
ggaatcctcg acgtgattgc ccagcagacg ccgagacgag gggaccgcac ctcttcggac    1740
gacgacgagc cgatccggat cttcgagctc cctccgctgc actacgcaca ggagagctcg    1800
ttcgtccctc gccaaaaccc ccggtcagaa gacgacggct acctcctcac ctacgtcttt    1860
gacgaacgcc aactcgaccc ctcgaccggt cgcgctgtcg aaggcgctaa gagcgagttg    1920
tgggtcatcg atgcgtggac gatgaaggac gttgtgtgca gggtcaagtt gccgcagagg    1980
gtgccgtacg ggttgcacgg gcattggttc tcgagggaag agatcgagga gcagcgcagg    2040
gctccctcag tccgctcgcg tcctccgcca aagtcctag                           2079

<210> SEQ ID NO 11
<211> LENGTH: 1911
<212> TYPE: DNA
<213> ORGANISM: Rhodosporidium toruloides
<220> FEATURE:
<221> NAME/KEY: CDS
<222> LOCATION: (1)..(1911)

<400> SEQUENCE: 11 atg ggg acg aag ccc cgg cac acc tac aag cag ggg aac tac ctc ccc     48
Met Gly Thr Lys Pro Arg His Thr Tyr Lys Gln Gly Asn Tyr Leu Pro
1               5                  10                  15 gtg cga gag gag cgc acg ctc gag gag tgc gct tgc gaa ggt cag ctc     96
Val Arg Glu Glu Arg Thr Leu Glu Glu Cys Ala Cys Glu Gly Gln Leu
            20                  25                  30 ccg caa gag ctc gtc ggc ggg atg tac gtg cgg aat ggg ggt gag cct    144
Pro Gln Glu Leu Val Gly Gly Met Tyr Val Arg Asn Gly Gly Glu Pro
        35                  40                  45 gcg ctg gca gag ttg cga gga gac gac tcc gca gac gga cct gcc tac    192
Ala Leu Ala Glu Leu Arg Gly Asp Asp Ser Ala Asp Gly Pro Ala Tyr
    50                  55                  60 cac tgg ttc gac ggt gac ggc atg ctg acg ggc gtg tac ttc aag ccc    240
His Trp Phe Asp Gly Asp Gly Met Leu Thr Gly Val Tyr Phe Lys Pro
65                  70                  75                  80 gtc ccc tcc tcc tcg ccc ttc gac ccg aac ccg cgt atc gcc ccg ctc    288
Val Pro Ser Ser Ser Pro Phe Asp Pro Asn Pro Arg Ile Ala Pro Leu
                85                  90                  95 ttc gtc aac aaa tac gtc ctc acc gac gtc ttc ctc gcc tcg aaa gcg    336
Phe Val Asn Lys Tyr Val Leu Thr Asp Val Phe Leu Ala Ser Lys Ala
            100                 105                 110 ctc ggc gtc aca cat ccc atc cta ccc tcc atc gcc aca ctc ctc ggc    384
Leu Gly Val Thr His Pro Ile Leu Pro Ser Ile Ala Thr Leu Leu Gly
        115                 120                 125 tca atc tgg tcc ctc cac ctc atc ctc tac tcc gtc ttt cgc gcc ctc    432
Ser Ile Trp Ser Leu His Leu Ile Leu Tyr Ser Val Phe Arg Ala Leu
    130                 135                 140 ttc ctc gcc ttc tgc tcc ttc ttc acc gaa tcg cct ttg cga cat ctc    480
Phe Leu Ala Phe Cys Ser Phe Phe Thr Glu Ser Pro Leu Arg His Leu
145                 150                 155                 160
```

```
tca gtc gcc aac acg tcg gtc ctg tgg cac gac gga cgg gcg ttg gcg      528
Ser Val Ala Asn Thr Ser Val Leu Trp His Asp Gly Arg Ala Leu Ala
                    165                 170                 175 agt tgc gag agc ggg ccg ttg aca tgg gtt acg ctg ccg gag ctc gat      576
Ser Cys Glu Ser Gly Pro Leu Thr Trp Val Thr Leu Pro Glu Leu Asp
        180                 185                 190 acg gtc ggg ttc tgg agt ctg gag ggc gac aat ggc gag aag ggg ctg      624
Thr Val Gly Phe Trp Ser Leu Glu Gly Asp Asn Gly Glu Lys Gly Leu
                195                 200                 205 cga gag cag ggt ggc atg ctc ggc tgg atg aag gag tgg acg acg gcg      672
Arg Glu Gln Gly Gly Met Leu Gly Trp Met Lys Glu Trp Thr Thr Ala
    210                 215                 220 cat ccg aag cgc gac ccg cac acc ggc gaa ctt atg ctc ttc cac atg      720
His Pro Lys Arg Asp Pro His Thr Gly Glu Leu Met Leu Phe His Met
225                 230                 235                 240 tcg ttc ctc ccg ccc tac ctc cac tac tcc gtc atc cct tcc act cac      768
Ser Phe Leu Pro Pro Tyr Leu His Tyr Ser Val Ile Pro Ser Thr His
                    245                 250                 255 gct cct cct ccc tcc gcc cgt tcc gag aag gcc gca ccc act cct cgc      816
Ala Pro Pro Pro Ser Ala Arg Ser Glu Lys Ala Ala Pro Thr Pro Arg
                260                 265                 270 atc ctc gcc gcc ccc gtt ccc atc gcc gca cct cgc atg atg cac gat      864
Ile Leu Ala Ala Pro Val Pro Ile Ala Ala Pro Arg Met Met His Asp
            275                 280                 285 atg gcc gcc tct cgg acg cac tcg atc ctc ctc gac atg ccc ctc tcg      912
Met Ala Ala Ser Arg Thr His Ser Ile Leu Leu Asp Met Pro Leu Ser
        290                 295                 300 ctc gac ccg cgc aat ctc gca ctc ggc aag ccc gtc atc tcc tac gac      960
Leu Asp Pro Arg Asn Leu Ala Leu Gly Lys Pro Val Ile Ser Tyr Asp
305                 310                 315                 320 ccg tcc aaa ccc gct cgc ttc ggc gtc ttg cct cgc cac aaa ccg aca     1008
Pro Ser Lys Pro Ala Arg Phe Gly Val Leu Pro Arg His Lys Pro Thr
                    325                 330                 335 ctc gtc aag tgg tac atc gcc ccg gcg tgc ata atc ttt cac acc gct     1056
Leu Val Lys Trp Tyr Ile Ala Pro Ala Cys Ile Ile Phe His Thr Ala
                340                 345                 350 ttc gcg tac gac gag ccc ccc tca act tcc cac gac gag gtc gag gca     1104
Phe Ala Tyr Asp Glu Pro Pro Ser Thr Ser His Asp Glu Val Glu Ala
            355                 360                 365 gtc aac ctc gtc tgc tgc cgc ctc aac tct ccc cgc ctc atc tac tcc     1152
Val Asn Leu Val Cys Cys Arg Leu Asn Ser Pro Arg Leu Ile Tyr Ser
        370                 375                 380 gcc ggt aac ctc gtc ctc ccc gag tct caa tcc ctc cca gca ggc gcc     1200
Ala Gly Asn Leu Val Leu Pro Glu Ser Gln Ser Leu Pro Ala Gly Ala
385                 390                 395                 400 aaa gag tcc tgc gag ctc tac tac tac cgc ttc ccc tct tcc tcc tcc     1248
Lys Glu Ser Cys Glu Leu Tyr Tyr Tyr Arg Phe Pro Ser Ser Ser Ser
                    405                 410                 415 gcc tcc gtc acc ctc gaa ccg tcg cac gcc ttc ccc ctc gcc gcg att     1296
Ala Ser Val Thr Leu Glu Pro Ser His Ala Phe Pro Leu Ala Ala Ile
                420                 425                 430 ccc ttc gag ttc ccg acc gta ccg cag gac cgc gcg gtc ggc ccg tcg     1344
Pro Phe Glu Phe Pro Thr Val Pro Gln Asp Arg Ala Val Gly Pro Ser
            435                 440                 445 aag tac gtc tat ggg tgc tcg gtg aag cac ggg tcg ttc gat gcg gcg     1392
Lys Tyr Val Tyr Gly Cys Ser Val Lys His Gly Ser Phe Asp Ala Ala
        450                 455                 460 ctt ggg tcg gcg gcg aag atc gac tgc ctc gtc aag gtc aac gtc gac     1440
Leu Gly Ser Ala Ala Lys Ile Asp Cys Leu Val Lys Val Asn Val Asp
```

```
                    465                 470                 475                 480
ttg ctc gtc cgg cag ggc aag aag cgc aac gag gcg ggc gag gga cag              1488
Leu Leu Val Arg Gln Gly Lys Lys Arg Asn Glu Ala Gly Glu Gly Gln
                    485                 490                 495 tcg gag cga ccg gtc gac gag cga gga atc ctc gac gtg att gcc cag              1536
Ser Glu Arg Pro Val Asp Glu Arg Gly Ile Leu Asp Val Ile Ala Gln
                500                 505                 510 cag acg ccg aga cga ggg gac cgc acc tct tcg gac gac gac gag ccg              1584
Gln Thr Pro Arg Arg Gly Asp Arg Thr Ser Ser Asp Asp Asp Glu Pro
                515                 520                 525 atc cgg atc ttc gag ctc cct ccg ctg cac tac gca cag gag agc tcg              1632
Ile Arg Ile Phe Glu Leu Pro Pro Leu His Tyr Ala Gln Glu Ser Ser
            530                 535                 540 ttc gtc cct cgc caa aac ccc cgg tca gaa gac gac ggc tac ctc ctc              1680
Phe Val Pro Arg Gln Asn Pro Arg Ser Glu Asp Asp Gly Tyr Leu Leu
545                 550                 555                 560 acc tac gtc ttt gac gaa cgc caa ctc gac ccc tcg acc ggt cgc gct              1728
Thr Tyr Val Phe Asp Glu Arg Gln Leu Asp Pro Ser Thr Gly Arg Ala
                565                 570                 575 gtc gaa ggc gct aag agc gag ttg tgg gtc atc gat gcg tgg acg atg              1776
Val Glu Gly Ala Lys Ser Glu Leu Trp Val Ile Asp Ala Trp Thr Met
                580                 585                 590 aag gac gtt gtg tgc agg gtc aag ttg ccg cag agg gtg ccg tac ggg              1824
Lys Asp Val Val Cys Arg Val Lys Leu Pro Gln Arg Val Pro Tyr Gly
                595                 600                 605 ttg cac ggg cat tgg ttc tcg agg gaa gag atc gag gag cag cgc agg              1872
Leu His Gly His Trp Phe Ser Arg Glu Glu Ile Glu Glu Gln Arg Arg
            610                 615                 620 gct ccc tca gtc cgc tcg cgt cct ccg cca aag tcc tag                          1911
Ala Pro Ser Val Arg Ser Arg Pro Pro Pro Lys Ser
625                 630                 635

<210> SEQ ID NO 12
<211> LENGTH: 636
<212> TYPE: PRT
<213> ORGANISM: Rhodosporidium toruloides

<400> SEQUENCE: 12

Met Gly Thr Lys Pro Arg His Thr Tyr Lys Gln Gly Asn Tyr Leu Pro
1               5                   10                  15

Val Arg Glu Glu Arg Thr Leu Glu Glu Cys Ala Cys Glu Gly Gln Leu
            20                  25                  30

Pro Gln Glu Leu Val Gly Gly Met Tyr Val Arg Asn Gly Gly Glu Pro
        35                  40                  45

Ala Leu Ala Glu Leu Arg Gly Asp Asp Ser Ala Asp Gly Pro Ala Tyr
    50                  55                  60

His Trp Phe Asp Gly Asp Gly Met Leu Thr Gly Val Tyr Phe Lys Pro
65                  70                  75                  80

Val Pro Ser Ser Ser Pro Phe Asp Pro Asn Pro Arg Ile Ala Pro Leu
                85                  90                  95

Phe Val Asn Lys Tyr Val Leu Thr Asp Val Phe Leu Ala Ser Lys Ala
            100                 105                 110

Leu Gly Val Thr His Pro Ile Leu Pro Ser Ile Ala Thr Leu Leu Gly
        115                 120                 125

Ser Ile Trp Ser Leu His Leu Ile Leu Tyr Ser Val Phe Arg Ala Leu
    130                 135                 140

Phe Leu Ala Phe Cys Ser Phe Phe Thr Glu Ser Pro Leu Arg His Leu
145                 150                 155                 160
```

```
Ser Val Ala Asn Thr Ser Val Leu Trp His Asp Gly Arg Ala Leu Ala
                165                 170                 175

Ser Cys Glu Ser Gly Pro Leu Thr Trp Val Thr Leu Pro Glu Leu Asp
                180                 185                 190

Thr Val Gly Phe Trp Ser Leu Glu Gly Asp Asn Gly Glu Lys Gly Leu
                195                 200                 205

Arg Glu Gln Gly Gly Met Leu Gly Trp Met Lys Glu Trp Thr Thr Ala
                210                 215                 220

His Pro Lys Arg Asp Pro His Thr Gly Glu Leu Met Leu Phe His Met
225                 230                 235                 240

Ser Phe Leu Pro Pro Tyr Leu His Tyr Ser Val Ile Pro Ser Thr His
                245                 250                 255

Ala Pro Pro Pro Ser Ala Arg Ser Glu Lys Ala Ala Pro Thr Pro Arg
                260                 265                 270

Ile Leu Ala Ala Pro Val Pro Ile Ala Ala Pro Arg Met Met His Asp
                275                 280                 285

Met Ala Ala Ser Arg Thr His Ser Ile Leu Leu Asp Met Pro Leu Ser
                290                 295                 300

Leu Asp Pro Arg Asn Leu Ala Leu Gly Lys Pro Val Ile Ser Tyr Asp
305                 310                 315                 320

Pro Ser Lys Pro Ala Arg Phe Gly Val Leu Pro Arg His Lys Pro Thr
                325                 330                 335

Leu Val Lys Trp Tyr Ile Ala Pro Ala Cys Ile Ile Phe His Thr Ala
                340                 345                 350

Phe Ala Tyr Asp Glu Pro Pro Ser Thr Ser His Asp Glu Val Glu Ala
                355                 360                 365

Val Asn Leu Val Cys Cys Arg Leu Asn Ser Pro Arg Leu Ile Tyr Ser
370                 375                 380

Ala Gly Asn Leu Val Leu Pro Glu Ser Gln Ser Leu Pro Ala Gly Ala
385                 390                 395                 400

Lys Glu Ser Cys Glu Leu Tyr Tyr Arg Phe Pro Ser Ser Ser Ser
                405                 410                 415

Ala Ser Val Thr Leu Glu Pro Ser His Ala Phe Pro Leu Ala Ala Ile
                420                 425                 430

Pro Phe Glu Phe Pro Thr Val Pro Gln Asp Arg Ala Val Gly Pro Ser
                435                 440                 445

Lys Tyr Val Tyr Gly Cys Ser Val Lys His Gly Ser Phe Asp Ala Ala
                450                 455                 460

Leu Gly Ser Ala Ala Lys Ile Asp Cys Leu Val Lys Val Asn Val Asp
465                 470                 475                 480

Leu Leu Val Arg Gln Gly Lys Lys Arg Asn Glu Ala Gly Glu Gly Gln
                485                 490                 495

Ser Glu Arg Pro Val Asp Glu Arg Gly Ile Leu Asp Val Ile Ala Gln
                500                 505                 510

Gln Thr Pro Arg Arg Gly Asp Arg Thr Ser Ser Asp Asp Glu Pro
                515                 520                 525

Ile Arg Ile Phe Glu Leu Pro Pro Leu His Tyr Ala Gln Glu Ser Ser
530                 535                 540

Phe Val Pro Arg Gln Asn Pro Arg Ser Glu Asp Gly Tyr Leu Leu
545                 550                 555                 560

Thr Tyr Val Phe Asp Glu Arg Gln Leu Asp Pro Ser Thr Gly Arg Ala
                565                 570                 575
```

Val Glu Gly Ala Lys Ser Glu Leu Trp Val Ile Asp Ala Trp Thr Met
            580                 585                 590

Lys Asp Val Val Cys Arg Val Lys Leu Pro Gln Arg Val Pro Tyr Gly
        595                 600                 605

Leu His Gly His Trp Phe Ser Arg Glu Glu Ile Glu Glu Gln Arg Arg
    610                 615                 620

Ala Pro Ser Val Arg Ser Arg Pro Pro Lys Ser
625                 630                 635

<210> SEQ ID NO 13
<211> LENGTH: 793
<212> TYPE: DNA
<213> ORGANISM: Rhodosporidium toruloides

<400> SEQUENCE: 13
atgctccacc ctctcgcacg cctccgcgcc gcctcgctcg tcctgctcgc aaccctcaca      60
cccctcgcac tcggaaacac cgaaatcctc gtctcacgct tgccgttcga gcttgcggat     120
cttccgaaag ctgcgcacag tgcatcagtg tacgtacacg cccgtacact ccctcttgcg     180
cggtcgaggg ctcaccaact cttcatcagt tctccccaca tcctcgaact ttattcgccg     240
caaacgctct ctatccgcct gactgagggt caggatgttc cgacagagct catcataccg     300
ctcgatgcag ctggaaaagc gccgacgggc ttgctcggcc gactggacag gcttgagcgg     360
gcgatgggac tggaaatgcg aactgtaagg ctgtcgtggc ctgcttcggt gcgtacagct     420
tactgtctcc tcttgttgtg aaccagctaa cctcgtagcc gcacagcacc cgaccacctt     480
ccacctctcg acccaccgcg ctccctcatc ctcgcctgac ccttccctcc ctcacctcct     540
catctccgcc actccatcct tcgtctcccc tcctgtgaca caaaccctct acgtcccctt     600
caccatcctt tcgaaccaa tccacttcgg cggcgtgccg aatcgacgc tgccgtttgt     660 tctggtactg gttgggttgg tgggagtgat gggagtgagt ggagtggcgg agggatggg     720 gaggtggttg gaggagctgg cagaggccga ttggaagctt ggtcgggcgg agaagacga     780 gaaggcggat tga                                                       793

<210> SEQ ID NO 14
<211> LENGTH: 675
<212> TYPE: DNA
<213> ORGANISM: Rhodosporidium toruloides
<220> FEATURE:
<221> NAME/KEY: CDS
<222> LOCATION: (1)..(675)

<400> SEQUENCE: 14 atg ctc cac cct ctc gca cgc ctc cgc gcc gcc tcg ctc gtc ctg ctc        48
Met Leu His Pro Leu Ala Arg Leu Arg Ala Ala Ser Leu Val Leu Leu
1               5                   10                  15 gca acc ctc aca ccc ctc gca ctc gga aac acc gaa atc ctc gtc tca        96
Ala Thr Leu Thr Pro Leu Ala Leu Gly Asn Thr Glu Ile Leu Val Ser
            20                  25                  30 cgc ttg ccg ttc gag ctt gcg gat ctt ccg aaa gct gcg cac agt gca       144
Arg Leu Pro Phe Glu Leu Ala Asp Leu Pro Lys Ala Ala His Ser Ala
        35                  40                  45 tca gtg tct ccc cac atc ctc gaa ctt tat tcg ccg caa acg ctc tct       192
Ser Val Ser Pro His Ile Leu Glu Leu Tyr Ser Pro Gln Thr Leu Ser
    50                  55                  60 atc cgc ctg act gag ggt cag gat gtt ccg aca gag ctc atc ata ccg       240
Ile Arg Leu Thr Glu Gly Gln Asp Val Pro Thr Glu Leu Ile Ile Pro
65                  70                  75                  80

```
ctc gat gca gct gga aaa gcg ccg acg ggc ttg ctc ggc cga ctg gac    288
Leu Asp Ala Ala Gly Lys Ala Pro Thr Gly Leu Leu Gly Arg Leu Asp
                85                  90                  95 agg ctt gag cgg gcg atg gga ctg gaa atg cga act gta agg ctg tcg    336
Arg Leu Glu Arg Ala Met Gly Leu Glu Met Arg Thr Val Arg Leu Ser
            100                 105                 110 tgg cct gct tcg cac ccg acc acc ttc cac ctc tcg acc cac cgc gct    384
Trp Pro Ala Ser His Pro Thr Thr Phe His Leu Ser Thr His Arg Ala
        115                 120                 125 ccc tca tcc tcg cct gac cct tcc ctc cct cac ctc ctc atc tcc gcc    432
Pro Ser Ser Ser Pro Asp Pro Ser Leu Pro His Leu Leu Ile Ser Ala
    130                 135                 140 act cca tcc ttc gtc tcc ccc tcc tgt gac caa acc ctc tac gtc ccc    480
Thr Pro Ser Phe Val Ser Pro Ser Cys Asp Gln Thr Leu Tyr Val Pro
145                 150                 155                 160 ttc acc atc ctt ctc gaa cca atc cac ttc ggc ggc gtg ccg gaa tcg    528
Phe Thr Ile Leu Leu Glu Pro Ile His Phe Gly Gly Val Pro Glu Ser
                165                 170                 175 acg ctg ccg ttt gtt ctg gta ctg gtt ggg ttg gtg gga gtg atg gga    576
Thr Leu Pro Phe Val Leu Val Leu Val Gly Leu Val Gly Val Met Gly
            180                 185                 190 gtg agt gga gtg gcg gga ggg atg ggg agg tgg ttg gag gag ctg gca    624
Val Ser Gly Val Ala Gly Gly Met Gly Arg Trp Leu Glu Glu Leu Ala
        195                 200                 205 gag gcc gat tgg aag ctt ggt cgg gcg gga gaa gac gag aag gcg gat    672
Glu Ala Asp Trp Lys Leu Gly Arg Ala Gly Glu Asp Glu Lys Ala Asp
    210                 215                 220 tga                                                                 675
```

<210> SEQ ID NO 15
<211> LENGTH: 224
<212> TYPE: PRT
<213> ORGANISM: Rhodosporidium toruloides

<400> SEQUENCE: 15

```
Met Leu His Pro Leu Ala Arg Leu Arg Ala Ala Ser Leu Val Leu Leu
1               5                   10                  15

Ala Thr Leu Thr Pro Leu Ala Leu Gly Asn Thr Glu Ile Leu Val Ser
            20                  25                  30

Arg Leu Pro Phe Glu Leu Ala Asp Leu Pro Lys Ala Ala His Ser Ala
        35                  40                  45

Ser Val Ser Pro His Ile Leu Glu Leu Tyr Ser Pro Gln Thr Leu Ser
    50                  55                  60

Ile Arg Leu Thr Glu Gly Gln Asp Val Pro Thr Glu Leu Ile Ile Pro
65                  70                  75                  80

Leu Asp Ala Ala Gly Lys Ala Pro Thr Gly Leu Leu Gly Arg Leu Asp
                85                  90                  95

Arg Leu Glu Arg Ala Met Gly Leu Glu Met Arg Thr Val Arg Leu Ser
            100                 105                 110

Trp Pro Ala Ser His Pro Thr Thr Phe His Leu Ser Thr His Arg Ala
        115                 120                 125

Pro Ser Ser Ser Pro Asp Pro Ser Leu Pro His Leu Leu Ile Ser Ala
    130                 135                 140

Thr Pro Ser Phe Val Ser Pro Ser Cys Asp Gln Thr Leu Tyr Val Pro
145                 150                 155                 160

Phe Thr Ile Leu Leu Glu Pro Ile His Phe Gly Gly Val Pro Glu Ser
                165                 170                 175

Thr Leu Pro Phe Val Leu Val Leu Val Gly Leu Val Gly Val Met Gly
```

|  | 180 |  |  | 185 |  |  |  | 190 |  |  |  |
|---|---|---|---|---|---|---|---|---|---|---|---|
| Val | Ser | Gly | Val | Ala | Gly | Gly | Met | Gly | Arg | Trp | Leu | Glu | Glu | Leu | Ala |

|  | 195 |  |  | 200 |  |  |  | 205 |  |  |  |
|---|---|---|---|---|---|---|---|---|---|---|---|
| Glu | Ala | Asp | Trp | Lys | Leu | Gly | Arg | Ala | Gly | Glu | Asp | Glu | Lys | Ala | Asp |

|  | 210 |  |  | 215 |  |  |  | 220 |  |  |  |

<210> SEQ ID NO 16
<211> LENGTH: 2565
<212> TYPE: DNA
<213> ORGANISM: Rhodosporidium toruloides

<400> SEQUENCE: 16

```
cgctcgacga tggccgccat gcaggacact cccatcgaca gcatccccca ggtacatccc      60
acgctgaccc gcgcttctct cgctcgcttg cgtgtcgtcc tcgctttcgg agcttcgaaa     120
caggcgggac gaggggatcg tggtgcagcg cgcgcctggg gaggattcgc tggacatcgg     180
ggatattgct ggaggatact caggactttc tggattggtc ccgcccttcc cgcgcccgtc     240
gtcgctctcc agcatccatt ccccactcga cactccggca aactcgccgc tgactctccc     300
cttcgctcat tccgcaggct tacgacaccg tcaccaaggc gttcttgtcg ggaaagacta     360
ggcccatcgc ctggcgcaag gcgcagatca agaaactcgg gttccttgtc gtgagttcgc     420
ggttctttcg cgcggtcttt gcgacggctc gtccagtgca ggtcgcgctg gtgcgcgtcg     480
tcaatgtagt tgcgatgaaa cctgacccag caactccccc tcccacagca agacaacgaa     540
gacgccttcg tccgcgctct cgagcaagac tttggccgtc ccgctttcga gacaatcaca     600
gccgagatca accccgtcaa ggctgagatt aacgaggtct acgaccacct cgagaagtgg     660
gccaagccga ggcgcgtcaa gacttcggcg acgtggtacg ctaccaagcc gacggtctac     720
tcggagccta agggtgtcac gctcgttatc gggacgtgga actgtgcgtg cacttgtttt     780
gtacgaggtt gagtgtgtgt actgacggaa gatgtcgccg cagacccgat cacgctcctc     840
ctcgtcccgc ttctcggcgc catctctgcc ggctgcaccg cgctcgtcaa ggtgcgttgc     900
cgttcgaagt ccgtcgtact gcatgtctca ctgacactcg tcgctcccac agcccgctga     960
gcaagcccct cacgtcgccg cgctcgtcgc cgacctcctg cccaagtacc tcgaccccac    1020
cgccttcatc tgcatcaacg gcgccatccc tcaagcgacc gctctcctca aactcaagtt    1080
cgatcacatc ttctacaccg gttcgggaac ggtcggcaag atcgttgcgc gtgcggcggc    1140
ggagcacctt tgcccggtta cgcttgagtt gggggggaaag agtccggcgg ttgtgctgga    1200
tgatgcggat attgaggttg tggcgaggag gatcgtttgg gccaagttta ccaacgctgg    1260
gcaggtgcgt cgcgagaacc gggttgtgtc gttggtctcg ccgaagcggg cgcagatgct    1320
tagtcatccg cttgttgttg cgcacagatc tgcatctcga cagactacgt cctcacgacc    1380
ccgcagaccg agcccaagct cctcgaagcc ctcaagcgcg ctctcgccgc cttctccgcc    1440
aaccccgccg cctcctcctc ctcggaaaag tcgtcaacct cgctcgtgca aacccgaac     1500
tactcgcgca tcatcaacca gaaccactac aaccgcgttt cgaagttgct tgatgcgact    1560
aagggcgagg tggttgttgg aggcgggagg gacgagaagg agcgcaagat tgaggttacg    1620
attgtgaggg gcgtcaagcc ggatgactcg ctcatgtcgg gtgcgcactg cggctctccc    1680
cctgaagaac gaatgtggct gacgaatgcg accgagcaga ggagattttc ggccccgtcc    1740
tcccgatcat gaccctccca acgctcgacg acatggtcaa gttcatccag tcgcgcgaca    1800
ccctctcgc gctctacgtc ttcacgcaga gcaagaagaa ccgcgacttc agtgcgttcc    1860
ccgcctctct ctcgctcgct gaccttcgac tgactcggtg gtggatgcag tctttgagcg    1920
```

-continued

```
cactcgctcg ggaggattcg tccagaacga tgtgctcgtt cagttcatga tccctgggct    1980
gccgttcggc ggtacgggcg cggcgggtta cggaaactac cacggcaggc ggtgcgtccc    2040
gcttcttcgg caccgtgctt ccccgagtcc ggctgacctg ctcgcacgca gcaccttcga    2100
cacgttctcg cacgagcgcg cgtcggccaa tgtccccacc tggatggaca tgatcatggc    2160
gtcgcggtac cctccctaca cccgttcgtc cgggtcgtcc cttcctctct gtgctcgcta    2220
acacactcgt cccacacgtg cagagaagaa gctgaagatg ctcctgttcg cgaccaaggc    2280
ggtgatcaag aagcccagca agtttggctc gatctcgcgc ttgctcaagg tgattgccgc    2340
gatggtcgct ctcttggctg tcagggccag gctctgactg accgtcgtc gtcccacccc    2400
tccccttctc caccactcct cttcctctcg ggtcttggga atcgtgtgcg ctgggcagaa    2460
gttgacggga caggcgtgag gcgggacagg gttgatccaa cccctcagat ctttcactcc    2520
ttccacaagt gttgtctgta ccctctcctc accctctccc aatca                    2565

<210> SEQ ID NO 17
<211> LENGTH: 1628
<212> TYPE: DNA
<213> ORGANISM: Rhodosporidium toruloides
<220> FEATURE:
<221> NAME/KEY: CDS
<222> LOCATION: (28)..(1542)

<400> SEQUENCE: 17
actcgctcac gcttgctacg ctcgacg atg gcc gcc atg cag gac act ccc atc        54
                                Met Ala Ala Met Gln Asp Thr Pro Ile
                                 1               5 gac agc atc ccc cag gct tac gac acc gtc acc aag gcg ttc ttg tcg        102
Asp Ser Ile Pro Gln Ala Tyr Asp Thr Val Thr Lys Ala Phe Leu Ser
 10              15                  20                  25 gga aag act agg ccc atc gcc tgg cgc aag gcg cag atc aag aaa ctc        150
Gly Lys Thr Arg Pro Ile Ala Trp Arg Lys Ala Gln Ile Lys Lys Leu
             30                  35                  40 ggg ttc ctt gtc caa gac aac gaa gac gcc ttc gtc cgc gct ctc gag        198
Gly Phe Leu Val Gln Asp Asn Glu Asp Ala Phe Val Arg Ala Leu Glu
         45                  50                  55 caa gac ttt ggc cgt ccc gct ttc gag aca atc aca gcc gag atc aac        246
Gln Asp Phe Gly Arg Pro Ala Phe Glu Thr Ile Thr Ala Glu Ile Asn
     60                  65                  70 ccc gtc aag gct gag att aac gag gtc tac gac cac ctc gag aag tgg        294
Pro Val Lys Ala Glu Ile Asn Glu Val Tyr Asp His Leu Glu Lys Trp
 75                  80                  85 gcc aag ccg agg cgc gtc aag act tcg gcg acg tgg tac gct acc aag        342
Ala Lys Pro Arg Arg Val Lys Thr Ser Ala Thr Trp Tyr Ala Thr Lys
 90                  95                 100                 105 ccg acg gtc tac tcg gag cct aag ggt gtc acg ctc gtt atc ggg acg        390
Pro Thr Val Tyr Ser Glu Pro Lys Gly Val Thr Leu Val Ile Gly Thr
            110                 115                 120 tgg aac tac ccg atc acg ctc ctc ctc gtc ccg ctt ctc ggc gcc atc        438
Trp Asn Tyr Pro Ile Thr Leu Leu Leu Val Pro Leu Leu Gly Ala Ile
        125                 130                 135 tct gcc ggc tgc acc gcg ctc gtc aag ccc gct gag caa gcc cct cac        486
Ser Ala Gly Cys Thr Ala Leu Val Lys Pro Ala Glu Gln Ala Pro His
    140                 145                 150 gtc gcc gcg ctc gtc gcc gac ctc ctg ccc aag tac ctc gac ccc acc        534
Val Ala Ala Leu Val Ala Asp Leu Leu Pro Lys Tyr Leu Asp Pro Thr
155                 160                 165 gcc ttc atc tgc atc aac ggc gcc atc cct caa gcg acc gct ctc ctc        582
```

```
Ala Phe Ile Cys Ile Asn Gly Ala Ile Pro Gln Ala Thr Ala Leu Leu
170                 175                 180                 185 aaa ctc aag ttc gat cac atc ttc tac acc ggt tcg gga acg gtc ggc        630
Lys Leu Lys Phe Asp His Ile Phe Tyr Thr Gly Ser Gly Thr Val Gly
                190                 195                 200 aag atc gtt gcg cgt gcg gcg gcg gag cac ctt tgc ccg gtt acg ctt        678
Lys Ile Val Ala Arg Ala Ala Ala Glu His Leu Cys Pro Val Thr Leu
            205                 210                 215 gag ttg ggg gga aag agt ccg gcg gtt gtg ctg gat gat gcg gat att        726
Glu Leu Gly Gly Lys Ser Pro Ala Val Val Leu Asp Asp Ala Asp Ile
        220                 225                 230 gag gtt gtg gcg agg agg atc gtt tgg gcc aag ttt acc aac gct ggg        774
Glu Val Val Ala Arg Arg Ile Val Trp Ala Lys Phe Thr Asn Ala Gly
    235                 240                 245 cag atc tgc atc tcg aca gac tac gtc ctc acg acc ccg cag acc gag        822
Gln Ile Cys Ile Ser Thr Asp Tyr Val Leu Thr Thr Pro Gln Thr Glu
250                 255                 260                 265 ccc aag ctc ctc gaa gcc ctc aag cgc gct ctc gcc gcc ttc tcc gcc        870
Pro Lys Leu Leu Glu Ala Leu Lys Arg Ala Leu Ala Ala Phe Ser Ala
                270                 275                 280 aac ccc gcc gcc tcc tcc tcc tcg gaa aag tcg tca acc tcg ctc gtg        918
Asn Pro Ala Ala Ser Ser Ser Ser Glu Lys Ser Ser Thr Ser Leu Val
            285                 290                 295 cac aac ccg aac tac tcg cgc atc atc aac cag aac cac tac aac cgc        966
His Asn Pro Asn Tyr Ser Arg Ile Ile Asn Gln Asn His Tyr Asn Arg
        300                 305                 310 gtt tcg aag ttg ctt gat gcg act aag ggc gag gtg gtt gtt gga ggc       1014
Val Ser Lys Leu Leu Asp Ala Thr Lys Gly Glu Val Val Val Gly Gly
    315                 320                 325 ggg agg gac gag aag gag cgc aag att gag gtt acg att gtg agg ggc       1062
Gly Arg Asp Glu Lys Glu Arg Lys Ile Glu Val Thr Ile Val Arg Gly
330                 335                 340                 345 gtc aag ccg gat gac tcg ctc atg tcg gag gag att ttc ggc ccc gtc       1110
Val Lys Pro Asp Asp Ser Leu Met Ser Glu Glu Ile Phe Gly Pro Val
                350                 355                 360 ctc ccg atc atg acc ctc cca acg ctc gac gac atg gtc aag ttc atc       1158
Leu Pro Ile Met Thr Leu Pro Thr Leu Asp Asp Met Val Lys Phe Ile
            365                 370                 375 cag tcg cgc gac acc cct ctc gcg ctc tac gtc ttc acg cag agc aag       1206
Gln Ser Arg Asp Thr Pro Leu Ala Leu Tyr Val Phe Thr Gln Ser Lys
        380                 385                 390 aag aac cgc gac ttc atc ttt gag cgc act cgc tcg gga gga ttc gtc       1254
Lys Asn Arg Asp Phe Ile Phe Glu Arg Thr Arg Ser Gly Gly Phe Val
    395                 400                 405 cag aac gat gtg ctc gtt cag ttc atg atc cct ggg ctg ccg ttc ggc       1302
Gln Asn Asp Val Leu Val Gln Phe Met Ile Pro Gly Leu Pro Phe Gly
410                 415                 420                 425 ggt acg ggc gcg gcg ggt tac gga aac tac cac ggc agg cgc acc ttc       1350
Gly Thr Gly Ala Ala Gly Tyr Gly Asn Tyr His Gly Arg Arg Thr Phe
                430                 435                 440 gac acg ttc tcg cac gag cgc gcg tcg gcc aat gtc ccc acc tgg atg       1398
Asp Thr Phe Ser His Glu Arg Ala Ser Ala Asn Val Pro Thr Trp Met
            445                 450                 455 gac atg atc atg gcg tcg cgg tac cct ccc tac acc cag aag aag ctg       1446
Asp Met Ile Met Ala Ser Arg Tyr Pro Pro Tyr Thr Gln Lys Lys Leu
        460                 465                 470 aag atg ctc ctg ttc gcg acc aag gcg gtg atc aag aag ccc agc aag       1494
Lys Met Leu Leu Phe Ala Thr Lys Ala Val Ile Lys Lys Pro Ser Lys
    475                 480                 485
```

```
                                                                      -continued ttt ggc tcg atc tcg cgc ttg ctc aag aag ttg acg gga cag gcg tga      1542
Phe Gly Ser Ile Ser Arg Leu Leu Lys Lys Leu Thr Gly Gln Ala
490             495                 500 ggcgggacag ggttgatcca acccctcaga tctttcactc cttccacaag tgttgtctgt    1602
accctctcct caccctctcc caatca                                         1628
```

<210> SEQ ID NO 18
<211> LENGTH: 504
<212> TYPE: PRT
<213> ORGANISM: Rhodosporidium toruloides

<400> SEQUENCE: 18

```
Met Ala Ala Met Gln Asp Thr Pro Ile Asp Ser Ile Pro Gln Ala Tyr
1               5                   10                  15

Asp Thr Val Thr Lys Ala Phe Leu Ser Gly Lys Thr Arg Pro Ile Ala
            20                  25                  30

Trp Arg Lys Ala Gln Ile Lys Lys Leu Gly Phe Leu Val Gln Asp Asn
        35                  40                  45

Glu Asp Ala Phe Val Arg Ala Leu Glu Gln Asp Phe Gly Arg Pro Ala
    50                  55                  60

Phe Glu Thr Ile Thr Ala Glu Ile Asn Pro Val Lys Ala Glu Ile Asn
65                  70                  75                  80

Glu Val Tyr Asp His Leu Glu Lys Trp Ala Lys Pro Arg Arg Val Lys
                85                  90                  95

Thr Ser Ala Thr Trp Tyr Ala Thr Lys Pro Thr Val Tyr Ser Glu Pro
            100                 105                 110

Lys Gly Val Thr Leu Val Ile Gly Thr Trp Asn Tyr Pro Ile Thr Leu
        115                 120                 125

Leu Leu Val Pro Leu Leu Gly Ala Ile Ser Ala Gly Cys Thr Ala Leu
    130                 135                 140

Val Lys Pro Ala Glu Gln Ala Pro His Val Ala Ala Leu Val Ala Asp
145                 150                 155                 160

Leu Leu Pro Lys Tyr Leu Asp Pro Thr Ala Phe Ile Cys Ile Asn Gly
                165                 170                 175

Ala Ile Pro Gln Ala Thr Ala Leu Leu Lys Leu Lys Phe Asp His Ile
            180                 185                 190

Phe Tyr Thr Gly Ser Gly Thr Val Gly Lys Ile Val Ala Arg Ala Ala
        195                 200                 205

Ala Glu His Leu Cys Pro Val Thr Leu Glu Leu Gly Gly Lys Ser Pro
    210                 215                 220

Ala Val Val Leu Asp Asp Ala Asp Ile Glu Val Val Ala Arg Arg Ile
225                 230                 235                 240

Val Trp Ala Lys Phe Thr Asn Ala Gly Gln Ile Cys Ile Ser Thr Asp
                245                 250                 255

Tyr Val Leu Thr Thr Pro Gln Thr Glu Pro Lys Leu Leu Glu Ala Leu
            260                 265                 270

Lys Arg Ala Leu Ala Ala Phe Ser Ala Asn Pro Ala Ala Ser Ser Ser
        275                 280                 285

Ser Glu Lys Ser Ser Thr Ser Leu Val His Asn Pro Asn Tyr Ser Arg
    290                 295                 300

Ile Ile Asn Gln Asn His Tyr Asn Arg Val Lys Leu Leu Asp Ala
305                 310                 315                 320

Thr Lys Gly Glu Val Val Gly Gly Gly Arg Asp Glu Lys Glu Arg
                325                 330                 335

Lys Ile Glu Val Thr Ile Val Arg Gly Val Lys Pro Asp Asp Ser Leu
```

```
                340             345             350
Met Ser Glu Glu Ile Phe Gly Pro Val Leu Pro Ile Met Thr Leu Pro
            355                 360                 365

Thr Leu Asp Asp Met Val Lys Phe Ile Gln Ser Arg Asp Thr Pro Leu
        370                 375                 380

Ala Leu Tyr Val Phe Thr Gln Ser Lys Lys Asn Arg Asp Phe Ile Phe
385                 390                 395                 400

Glu Arg Thr Arg Ser Gly Gly Phe Val Gln Asn Asp Val Leu Val Gln
                405                 410                 415

Phe Met Ile Pro Gly Leu Pro Phe Gly Gly Thr Gly Ala Ala Gly Tyr
            420                 425                 430

Gly Asn Tyr His Gly Arg Arg Thr Phe Asp Thr Phe Ser His Glu Arg
                435                 440                 445

Ala Ser Ala Asn Val Pro Thr Trp Met Asp Met Ile Met Ala Ser Arg
            450                 455                 460

Tyr Pro Pro Tyr Thr Gln Lys Lys Leu Lys Met Leu Leu Phe Ala Thr
465                 470                 475                 480

Lys Ala Val Ile Lys Lys Pro Ser Lys Phe Gly Ser Ile Ser Arg Leu
                485                 490                 495

Leu Lys Lys Leu Thr Gly Gln Ala
            500

<210> SEQ ID NO 19
<211> LENGTH: 3136
<212> TYPE: DNA
<213> ORGANISM: Rhodosporidium toruloides

<400> SEQUENCE: 19
cagccccggt ctacctttcg ccgacctcgt cctcagctcc ctcgcccatg gacgcgctcg      60
ctgccacgat ctgagcaacc acgcatgtcg actctagcca tcagacccga cgaaccaccg     120
aacgagcgac ttcgcgacac cgtccccgac ctcgacccgt ctggcggagg agtgcgtccg     180
gcgatgtctc ctcgagatcg gtcgcctgcc agctctcgtg gctcgcagga cgacagctcg     240
tcgacattgt cggatcgtgg gcgacagcgc aggcgttcgg caagctcgga acggtcggat     300
cagcctgaag aagcggagaa gactgcggat ccacctcagg cttcaggtgc gtccggctcg     360
ctctcctgac gctcgcgccg ctcccagacg ttggtactga ctgtgtggtc atcgcgtcga     420
caggcctggc gcatcccgct ctcccgaggc acctcatcc gatcgccagg tcctcctccg     480
ccaccacgtc tgtccccgcg ccttctgctt ccgtgcgcgc cgatcgcctc gaccaccagc     540
ttcagaccac gtctccagat tgccccgccc catctcgcat gcgccgcgtc gctcgtgtct     600
ctcccaattc ccgcaacgag cgccccgtgc cgtccgccat cccttcctcc aacttctccg     660
cccaccatcg accagcccac ggtctgcgtc gacaatcctc cctccctcca tcgagccgcc     720
gcgcgagggc gagctcgctg agccgccgt cgacctcgtc aggtctcgct tcttcctcgt     780
accgtccgtc ccggcacctg gatcctgacc agcattggct ttcagaggac gaggcgcacg     840
acgccgtcag ggttgcggat cggccgcgtc ggccacggcg gacgaggtcg agcaggagcg     900
acgactcgga aggtcccgag cgcgacagcc caagctcct cgccgcgtcg ggccttggcg     960
aagacccgac gtcggctcac cacatccaca accgaccctc caaggcgttc agaccgtcgg    1020
cgacgccgcc gatggcagag ttgacggacg ggcgatcgct gtacgctgtc gtcccggacc    1080
tcgctcgcct cctcctctgc ccgtcctgcc accgcctcta caccgatccc gccacactcg    1140
cctgcggtca ctcgcgctgc ctcgtctgct cgggagcgtc agataccctc gccacccgc    1200
```

| | |
|---|---|
| cgatcgagac ggcgtcgatg acgaccacga ccgccttcac cttcactccg cccgccgtcg | 1260 |
| cgcggcatac ggccggcatc gcctcgcctc tcccttcgcc ccccgtcgtc gcacacctcg | 1320 |
| acaacaacca gctgtatcgc accttgtcgg cgacatcgac gacttcgaca ccttccgtcg | 1380 |
| cctcgaccgc tcagacgcac atccccgtcg atcttcccaa tctcacctgc cccgactcgt | 1440 |
| cgtgcgacta caacttctcg cacctcatcg tcccccacct cccgcttcat gtcgactaca | 1500 |
| ccctgcgcaa ggtcagcgag atgctgcaga aggctgtgcc tggactggca gcatgggcga | 1560 |
| cgcgtcttgc gtcgaagaac gacccgcatc tcgcgccgtt gttctcggat gtgcgattgg | 1620 |
| cgagtgaggc gccgaccgat gtcgaggaga acggcgagca gccgatggtc gagggcgacg | 1680 |
| tccagcctgg tgcggtatcg cgcacgagca gcggcagcag tggcggcggc gacgaggaga | 1740 |
| cgatcgaagg gcacgacgac agcaagcggg cgcacaagtc gcgcaagtcg tggcaggcga | 1800 |
| gcaagaagac gcgaacggtg tcgttcagcg acgtctcgat ggcttcgcct gccgtcggtc | 1860 |
| catctcgcac gtcgacgccg acgccgcacg ccgcacaacg agacgacaag cacctcgaca | 1920 |
| tcgctggctt gtcgccgtcg ttcctcaccg acctgcacaa cgagtgcgag tgtcaagtgt | 1980 |
| gcttccagct cttccacgag ccggtcacct cgccttgcgg ccactcgttc tgccgacaat | 2040 |
| gcctcgcccg ctcgtacgat cactccgaca agtgccctct ctgccgcgcc gacctcccgc | 2100 |
| ccctcgccta cttccgctgg caacgaccca acatcgcgct caccaagatt atcgagaccg | 2160 |
| ctctccctca acaagccgct gagcgcgccg cgaccgtcaa ggaggaagaa cttgcgctgc | 2220 |
| ttgcgtcggt ccccgtgttc gtctgtacga ccgcatggcc aggcatcaag tgcttcctgc | 2280 |
| acatcttcga gcctcggtat cgcctcatgg tccgccgcgt gctcgagacg cccgaacgtt | 2340 |
| cgttcggcat ggtccttcct ctccgcagcg ccggacccga cgctgtcaac gagtatggca | 2400 |
| ccatgttgcg cgtcacgagc tgtcagatgc tcgaggacgg ccgcctcatc ctcgagacga | 2460 |
| tcggacgta ccgcttccgc ctcctcgagc gcagcatggt cgacgggtac aacgtcggca | 2520 |
| aggtcgaacg tgtcgacgac gtctcgccgg aacaagaagc ggagcttgag cgggtcgcgc | 2580 |
| tcgcgaggaa cgatacccatc caagacgagt acgccgaccc tgaaccagtc ggaccggaca | 2640 |
| gcgtgcccct ctcgagaccg cccatgaccg gcaacgtcga gttgtcgacc gaccagctca | 2700 |
| tgcagatctg cctcgacttc ctcaccacgc tgcgcgctag ctcggcgccg tggattatcg | 2760 |
| agcggctgaa ccgacgggt gcgtctccat tcacttgct gcatctcttg ccggtactga | 2820 |
| ccttcgttct gcagtcggcg aggtgcccaa caccgcac gacttcagct ggttcgccgc | 2880 |
| cgaggtcttc cccgtcgaag atcacgtcaa ggtcacgctt ctccagtgcg tcgtccgtcg | 2940 |
| ttcgccatcc ttcttcgtcg cgctgatttc accgctgcgc aggatcacga gtgtccgcga | 3000 |
| acgactgcgc ttgatcgtct tctggatcga gcagttcagg tcgtcgtggt ggtactcccg | 3060 |
| aggctgtgcg ttccgtttcc tcttcctccg cctgacgttg ctgacgcctc tccgatgcac | 3120 |
| aggcaacatc gcctag | 3136 |

<210> SEQ ID NO 20
<211> LENGTH: 2889
<212> TYPE: DNA
<213> ORGANISM: Rhodosporidium toruloides
<220> FEATURE:
<221> NAME/KEY: CDS
<222> LOCATION: (85)..(2889)

<400> SEQUENCE: 20

| | |
|---|---|
| cagccccggt ctacctttcg ccgacctcgt cctcagctcc ctcgcccatg gacgcgctcg | 60 |

-continued

```
ctgccacgat ctgagcaacc acgc atg tcg act cta gcc atc aga ccc gac     111
                         Met Ser Thr Leu Ala Ile Arg Pro Asp
                         1               5 gaa cca ccg aac gag cga ctt cgc gac acc gtc ccc gac ctc gac ccg     159
Glu Pro Pro Asn Glu Arg Leu Arg Asp Thr Val Pro Asp Leu Asp Pro
10              15                  20                  25 tct ggc gga gga gtg cgt ccg gcg atg tct cct cga gat cgg tcg cct     207
Ser Gly Gly Gly Val Arg Pro Ala Met Ser Pro Arg Asp Arg Ser Pro
                30                  35                  40 gcc agc tct cgt ggc tcg cag gac gac agc tcg aca ttg tcg gat         255
Ala Ser Ser Arg Gly Ser Gln Asp Asp Ser Ser Thr Leu Ser Asp
            45                  50                  55 cgt ggg cga cag cgc agg cgt tcg gca agc tcg gaa cgg tcg gat cag     303
Arg Gly Arg Gln Arg Arg Arg Ser Ala Ser Ser Glu Arg Ser Asp Gln
        60                  65                  70 cct gaa gaa gcg gag aag act gcg gat cca cct cag gct tca ggc ctg     351
Pro Glu Glu Ala Glu Lys Thr Ala Asp Pro Pro Gln Ala Ser Gly Leu
75                  80                  85 gcg cat ccc gct tct ccc gag gca cct cat ccg atc gcc agg tcc tcc     399
Ala His Pro Ala Ser Pro Glu Ala Pro His Pro Ile Ala Arg Ser Ser
90                  95                  100                 105 tcc gcc acc acg tct gtc ccc gcg cct tct gct tcc gtg cgc gcc gat     447
Ser Ala Thr Thr Ser Val Pro Ala Pro Ser Ala Ser Val Arg Ala Asp
                110                 115                 120 cgc ctc gac cac cag ctt cag acc acg tct cca gat tgc ccc gcc cca     495
Arg Leu Asp His Gln Leu Gln Thr Thr Ser Pro Asp Cys Pro Ala Pro
            125                 130                 135 tct cgc atg cgc cgc gtc gct cgt gtc tct ccc aat tcc cgc aac gag     543
Ser Arg Met Arg Arg Val Ala Arg Val Ser Pro Asn Ser Arg Asn Glu
        140                 145                 150 cgc ccc gtg ccg tcc gcc atc cct tcc tcc aac ttc tcc gcc cac cat     591
Arg Pro Val Pro Ser Ala Ile Pro Ser Ser Asn Phe Ser Ala His His
155                 160                 165 cga cca gcc cac ggt ctg cgt cga caa tcc tcc ctc cct cca tcg agc     639
Arg Pro Ala His Gly Leu Arg Arg Gln Ser Ser Leu Pro Pro Ser Ser
170                 175                 180                 185 cgc cgc gcg agg gcg agc tcg ctg agc ccg ccg tcg acc tcg tca ggt     687
Arg Arg Ala Arg Ala Ser Ser Leu Ser Pro Pro Ser Thr Ser Ser Gly
                190                 195                 200 ctc gct tct tcc tcg tac cgt ccg tcc cgg cac ctg gat cct gac cag     735
Leu Ala Ser Ser Ser Tyr Arg Pro Ser Arg His Leu Asp Pro Asp Gln
            205                 210                 215 cat tgg ctt tca gag gac gag gcg cac gac gcc gtc agg gtt gcg gat     783
His Trp Leu Ser Glu Asp Glu Ala His Asp Ala Val Arg Val Ala Asp
        220                 225                 230 cgg ccg cgt cgg cca cgg cgg acg agg tcg agc agg agc gac gac tcg     831
Arg Pro Arg Arg Pro Arg Arg Thr Arg Ser Ser Arg Ser Asp Asp Ser
235                 240                 245 gaa ggt ccc gag cgc gac agc ccc aag ctc ctc gcc gcg tcg ggc ctt     879
Glu Gly Pro Glu Arg Asp Ser Pro Lys Leu Leu Ala Ala Ser Gly Leu
250                 255                 260                 265 ggc gaa gac ccg acg tcg gct cac cac atc cac aac cga ccc tcc aag     927
Gly Glu Asp Pro Thr Ser Ala His His Ile His Asn Arg Pro Ser Lys
                270                 275                 280 gcg ttc aga ccg tcg gcg acg ccg ccg atg gca gag ttg acg gac ggg     975
Ala Phe Arg Pro Ser Ala Thr Pro Pro Met Ala Glu Leu Thr Asp Gly
            285                 290                 295 cga tcg ctg tac gct gtc gtc ccg gac ctc gct cgc ctc ctc ctc tgc    1023
Arg Ser Leu Tyr Ala Val Val Pro Asp Leu Ala Arg Leu Leu Leu Cys
```

|       |       |       |       |       | 300   |       |       |       |       | 305   |       |       |       |       | 310   |       |      |
|-------|-------|-------|-------|-------|-------|-------|-------|-------|-------|-------|-------|-------|-------|-------|-------|-------|------|
| ccg   | tcc   | tgc   | cac   | cgc   | ctc   | tac   | acc   | gat   | ccc   | gcc   | aca   | ctc   | gcc   | tgc   | ggt   |       | 1071 |
| Pro   | Ser   | Cys   | His   | Arg   | Leu   | Tyr   | Thr   | Asp   | Pro   | Ala   | Thr   | Leu   | Ala   | Cys   | Gly   |       |      |
|       | 315   |       |       |       |       | 320   |       |       |       |       | 325   |       |       |       |       |       |      |

| cac | tcg | cgc | tgc | ctc | gtc | tgc | tcg | gga | gcg | tca | gat | acc | ctc | gcc | acc | | 1119 |
|---|---|---|---|---|---|---|---|---|---|---|---|---|---|---|---|---|---|
| His | Ser | Arg | Cys | Leu | Val | Cys | Ser | Gly | Ala | Ser | Asp | Thr | Leu | Ala | Thr | | |
| 330 | | | | | 335 | | | | | 340 | | | | | 345 | | |

| ccg | ccg | atc | gag | acg | gcg | tcg | atg | acg | acc | acg | acc | gcc | ttc | acc | ttc | | 1167 |
|---|---|---|---|---|---|---|---|---|---|---|---|---|---|---|---|---|---|
| Pro | Pro | Ile | Glu | Thr | Ala | Ser | Met | Thr | Thr | Thr | Thr | Ala | Phe | Thr | Phe | | |
| | | | | 350 | | | | | 355 | | | | | 360 | | | |

| act | ccg | ccc | gcc | gtc | gcg | cgg | cat | acg | gcc | ggc | atc | gcc | tcg | cct | ctc | | 1215 |
|---|---|---|---|---|---|---|---|---|---|---|---|---|---|---|---|---|---|
| Thr | Pro | Pro | Ala | Val | Ala | Arg | His | Thr | Ala | Gly | Ile | Ala | Ser | Pro | Leu | | |
| | | 365 | | | | | 370 | | | | | 375 | | | | | |

| cct | tcg | ccc | ccc | gtc | gtc | gca | cac | ctc | gac | aac | aac | cag | ctg | tat | cgc | | 1263 |
|---|---|---|---|---|---|---|---|---|---|---|---|---|---|---|---|---|---|
| Pro | Ser | Pro | Pro | Val | Val | Ala | His | Leu | Asp | Asn | Asn | Gln | Leu | Tyr | Arg | | |
| | 380 | | | | | 385 | | | | | 390 | | | | | | |

| acc | ttg | tcg | gcg | aca | tcg | acg | act | tcg | aca | cct | tcc | gtc | gcc | tcg | acc | | 1311 |
|---|---|---|---|---|---|---|---|---|---|---|---|---|---|---|---|---|---|
| Thr | Leu | Ser | Ala | Thr | Ser | Thr | Thr | Ser | Thr | Pro | Ser | Val | Ala | Ser | Thr | | |
| | 395 | | | | | 400 | | | | | 405 | | | | | | |

| gct | cag | acg | cac | atc | ccc | gtc | gat | ctt | ccc | aat | ctc | acc | tgc | ccc | gac | | 1359 |
|---|---|---|---|---|---|---|---|---|---|---|---|---|---|---|---|---|---|
| Ala | Gln | Thr | His | Ile | Pro | Val | Asp | Leu | Pro | Asn | Leu | Thr | Cys | Pro | Asp | | |
| 410 | | | | | 415 | | | | | 420 | | | | | 425 | | |

| tcg | tcg | tgc | gac | tac | aac | ttc | tcg | cac | ctc | atc | gtc | ccc | cac | ctc | ccg | | 1407 |
|---|---|---|---|---|---|---|---|---|---|---|---|---|---|---|---|---|---|
| Ser | Ser | Cys | Asp | Tyr | Asn | Phe | Ser | His | Leu | Ile | Val | Pro | His | Leu | Pro | | |
| | | | | 430 | | | | | 435 | | | | | 440 | | | |

| ctt | cat | gtc | gac | tac | acc | ctg | cgc | aag | gtc | agc | gag | atg | ctg | cag | aag | | 1455 |
|---|---|---|---|---|---|---|---|---|---|---|---|---|---|---|---|---|---|
| Leu | His | Val | Asp | Tyr | Thr | Leu | Arg | Lys | Val | Ser | Glu | Met | Leu | Gln | Lys | | |
| | | | 445 | | | | | 450 | | | | | 455 | | | | |

| gct | gtg | cct | gga | ctg | gca | gca | tgg | gcg | acg | cgt | ctt | gcg | tcg | aag | aac | | 1503 |
|---|---|---|---|---|---|---|---|---|---|---|---|---|---|---|---|---|---|
| Ala | Val | Pro | Gly | Leu | Ala | Ala | Trp | Ala | Thr | Arg | Leu | Ala | Ser | Lys | Asn | | |
| | | 460 | | | | | 465 | | | | | 470 | | | | | |

| gac | ccg | cat | ctc | gcg | ccg | ttg | ttc | tcg | gat | gtg | cga | ttg | gcg | agt | gag | | 1551 |
|---|---|---|---|---|---|---|---|---|---|---|---|---|---|---|---|---|---|
| Asp | Pro | His | Leu | Ala | Pro | Leu | Phe | Ser | Asp | Val | Arg | Leu | Ala | Ser | Glu | | |
| | 475 | | | | | 480 | | | | | 485 | | | | | | |

| gcg | ccg | acc | gat | gtc | gag | gag | aac | ggc | gag | cag | ccg | atg | gtc | gag | ggc | | 1599 |
|---|---|---|---|---|---|---|---|---|---|---|---|---|---|---|---|---|---|
| Ala | Pro | Thr | Asp | Val | Glu | Glu | Asn | Gly | Glu | Gln | Pro | Met | Val | Glu | Gly | | |
| 490 | | | | | 495 | | | | | 500 | | | | | 505 | | |

| gac | gtc | cag | cct | ggt | gcg | gta | tcg | cgc | acg | agc | agc | ggc | agc | agt | ggc | | 1647 |
|---|---|---|---|---|---|---|---|---|---|---|---|---|---|---|---|---|---|
| Asp | Val | Gln | Pro | Gly | Ala | Val | Ser | Arg | Thr | Ser | Ser | Gly | Ser | Ser | Gly | | |
| | | | 510 | | | | | 515 | | | | | 520 | | | | |

| ggc | ggc | gac | gag | gag | acg | atc | gaa | ggg | cac | gac | gac | agc | aag | cgg | gcg | | 1695 |
|---|---|---|---|---|---|---|---|---|---|---|---|---|---|---|---|---|---|
| Gly | Gly | Asp | Glu | Glu | Thr | Ile | Glu | Gly | His | Asp | Asp | Ser | Lys | Arg | Ala | | |
| | | | 525 | | | | | 530 | | | | | 535 | | | | |

| cac | aag | tcg | cgc | aag | tcg | tgg | cag | gcg | agc | aag | aag | acg | cga | acg | gtg | | 1743 |
|---|---|---|---|---|---|---|---|---|---|---|---|---|---|---|---|---|---|
| His | Lys | Ser | Arg | Lys | Ser | Trp | Gln | Ala | Ser | Lys | Lys | Thr | Arg | Thr | Val | | |
| | | 540 | | | | | 545 | | | | | 550 | | | | | |

| tcg | ttc | agc | gac | gtc | tcg | atg | gct | tcg | cct | gcc | gtc | ggt | cca | tct | cgc | | 1791 |
|---|---|---|---|---|---|---|---|---|---|---|---|---|---|---|---|---|---|
| Ser | Phe | Ser | Asp | Val | Ser | Met | Ala | Ser | Pro | Ala | Val | Gly | Pro | Ser | Arg | | |
| | 555 | | | | | 560 | | | | | 565 | | | | | | |

| acg | tcg | acg | ccg | acg | ccg | cac | gcc | gca | caa | cga | gac | gac | aag | cac | ctc | | 1839 |
|---|---|---|---|---|---|---|---|---|---|---|---|---|---|---|---|---|---|
| Thr | Ser | Thr | Pro | Thr | Pro | His | Ala | Ala | Gln | Arg | Asp | Asp | Lys | His | Leu | | |
| 570 | | | | | 575 | | | | | 580 | | | | | 585 | | |

| gac | atc | gct | ggc | ttg | tcg | ccg | tcg | ttc | ctc | acc | gac | ctg | cac | aac | gag | | 1887 |
|---|---|---|---|---|---|---|---|---|---|---|---|---|---|---|---|---|---|
| Asp | Ile | Ala | Gly | Leu | Ser | Pro | Ser | Phe | Leu | Thr | Asp | Leu | His | Asn | Glu | | |
| | | | | 590 | | | | | 595 | | | | | 600 | | | |

| tgc | gag | tgt | caa | gtg | tgc | ttc | cag | ctc | ttc | cac | gag | ccg | gtc | acc | tcg | | 1935 |
|---|---|---|---|---|---|---|---|---|---|---|---|---|---|---|---|---|---|
| Cys | Glu | Cys | Gln | Val | Cys | Phe | Gln | Leu | Phe | His | Glu | Pro | Val | Thr | Ser | | |
| | | | 605 | | | | | 610 | | | | | 615 | | | | |

| cct | tgc | ggc | cac | tcg | ttc | tgc | cga | caa | tgc | ctc | gcc | cgc | tcg | tac | gat | | 1983 |
|---|---|---|---|---|---|---|---|---|---|---|---|---|---|---|---|---|---|

```
                Pro Cys Gly His Ser Phe Cys Arg Gln Cys Leu Ala Arg Ser Tyr Asp
                                620                 625                 630 cac tcc gac aag tgc cct ctc tgc cgc gcc gac ctc ccg ccc ctc gcc         2031
His Ser Asp Lys Cys Pro Leu Cys Arg Ala Asp Leu Pro Pro Leu Ala
635                 640                 645 tac ttc cgc tgg caa cga ccc aac atc gcg ctc acc aag att atc gag         2079
Tyr Phe Arg Trp Gln Arg Pro Asn Ile Ala Leu Thr Lys Ile Ile Glu
650                 655                 660                 665 acc gct ctc cct caa caa gcc gct gag cgc gcc gcg acc gtc aag gag         2127
Thr Ala Leu Pro Gln Gln Ala Ala Glu Arg Ala Ala Thr Val Lys Glu
                670                 675                 680 gaa gaa ctt gcg ctg ctt gcg tcg gtc ccc gtg ttc gtc tgt acg acc         2175
Glu Glu Leu Ala Leu Leu Ala Ser Val Pro Val Phe Val Cys Thr Thr
                685                 690                 695 gca tgg cca ggc atc aag tgc ttc ctg cac atc ttc gag cct cgg tat         2223
Ala Trp Pro Gly Ile Lys Cys Phe Leu His Ile Phe Glu Pro Arg Tyr
        700                 705                 710 cgc ctc atg gtc cgc cgc gtg ctc gag acg ccc gaa cgt tcg ttc ggc         2271
Arg Leu Met Val Arg Arg Val Leu Glu Thr Pro Glu Arg Ser Phe Gly
715                 720                 725 atg gtc ctt cct ctc cgc agc gcc gga ccc gac gct gtc aac gag tat         2319
Met Val Leu Pro Leu Arg Ser Ala Gly Pro Asp Ala Val Asn Glu Tyr
730                 735                 740                 745 ggc acc atg ttg cgc gtc acg agc tgt cag atg ctc gag gac ggc cgc         2367
Gly Thr Met Leu Arg Val Thr Ser Cys Gln Met Leu Glu Asp Gly Arg
                750                 755                 760 ctc atc ctc gag acg atc ggg acg tac cgc ttc cgc ctc ctc gag cgc         2415
Leu Ile Leu Glu Thr Ile Gly Thr Tyr Arg Phe Arg Leu Leu Glu Arg
                765                 770                 775 agc atg gtc gac ggg tac aac gtc ggc aag gtc gaa cgt gtc gac gac         2463
Ser Met Val Asp Gly Tyr Asn Val Gly Lys Val Glu Arg Val Asp Asp
                780                 785                 790 gtc tcg ccg gaa caa gaa gcg gag ctt gag cgg gtc gcg ctc gcg agg         2511
Val Ser Pro Glu Gln Glu Ala Glu Leu Glu Arg Val Ala Leu Ala Arg
795                 800                 805 aac gat acc ctc caa gac gag tac gcc gac cct gaa cca gtc gga ccg         2559
Asn Asp Thr Leu Gln Asp Glu Tyr Ala Asp Pro Glu Pro Val Gly Pro
810                 815                 820                 825 gac agc gtg ccc ctc tcg aga ccg ccc atg acc ggc aac gtc gag ttg         2607
Asp Ser Val Pro Leu Ser Arg Pro Pro Met Thr Gly Asn Val Glu Leu
                830                 835                 840 tcg acc gac cag ctc atg cag atc tgc ctc gac ttc ctc acc acg ctg         2655
Ser Thr Asp Gln Leu Met Gln Ile Cys Leu Asp Phe Leu Thr Thr Leu
                845                 850                 855 cgc gct agc tcg gcg ccg tgg att atc gag cgg ctg aac cgg acg gtc         2703
Arg Ala Ser Ser Ala Pro Trp Ile Ile Glu Arg Leu Asn Arg Thr Val
                860                 865                 870 ggc gag gtg ccc aac aac ccg cac gac ttc agc tgg ttc gcc gcc gag         2751
Gly Glu Val Pro Asn Asn Pro His Asp Phe Ser Trp Phe Ala Ala Glu
875                 880                 885 gtc ttc ccc gtc gaa gat cac gtc aag gtc acg ctt ctc cag atc acg         2799
Val Phe Pro Val Glu Asp His Val Lys Val Thr Leu Leu Gln Ile Thr
890                 895                 900                 905 agt gtc cgc gaa cga ctg cgc ttg atc gtc ttc tgg atc gag cag ttc         2847
Ser Val Arg Glu Arg Leu Arg Leu Ile Val Phe Trp Ile Glu Gln Phe
                910                 915                 920 agg tcg tcg tgg tgg tac tcc cga ggc tgc aac atc gcc tag             2889
Arg Ser Ser Trp Trp Tyr Ser Arg Gly Cys Asn Ile Ala
                925                 930
```

<210> SEQ ID NO 21
<211> LENGTH: 934
<212> TYPE: PRT
<213> ORGANISM: Rhodosporidium toruloides

<400> SEQUENCE: 21

```
Met Ser Thr Leu Ala Ile Arg Pro Asp Glu Pro Pro Asn Glu Arg Leu
1               5                   10                  15

Arg Asp Thr Val Pro Asp Leu Asp Pro Ser Gly Gly Gly Val Arg Pro
            20                  25                  30

Ala Met Ser Pro Arg Asp Arg Ser Pro Ala Ser Ser Arg Gly Ser Gln
        35                  40                  45

Asp Asp Ser Ser Ser Thr Leu Ser Asp Arg Gly Arg Gln Arg Arg Arg
    50                  55                  60

Ser Ala Ser Ser Glu Arg Ser Asp Gln Pro Glu Ala Glu Lys Thr
65                  70                  75                  80

Ala Asp Pro Pro Gln Ala Ser Gly Leu Ala His Pro Ala Ser Pro Glu
            85                  90                  95

Ala Pro His Pro Ile Ala Arg Ser Ser Ser Ala Thr Thr Ser Val Pro
        100                 105                 110

Ala Pro Ser Ala Ser Val Arg Ala Asp Arg Leu Asp His Gln Leu Gln
    115                 120                 125

Thr Thr Ser Pro Asp Cys Pro Ala Pro Ser Arg Met Arg Arg Val Ala
130                 135                 140

Arg Val Ser Pro Asn Ser Arg Asn Glu Arg Pro Val Pro Ser Ala Ile
145                 150                 155                 160

Pro Ser Ser Asn Phe Ser Ala His His Arg Pro Ala His Gly Leu Arg
                165                 170                 175

Arg Gln Ser Ser Leu Pro Pro Ser Arg Arg Ala Arg Ala Ser Ser
            180                 185                 190

Leu Ser Pro Pro Ser Thr Ser Ser Gly Leu Ala Ser Ser Ser Tyr Arg
    195                 200                 205

Pro Ser Arg His Leu Asp Pro Asp Gln His Trp Leu Ser Glu Asp Glu
210                 215                 220

Ala His Asp Ala Val Arg Val Ala Asp Arg Pro Arg Arg Pro Arg Arg
225                 230                 235                 240

Thr Arg Ser Ser Arg Ser Asp Asp Ser Glu Gly Pro Glu Arg Asp Ser
                245                 250                 255

Pro Lys Leu Leu Ala Ala Ser Gly Leu Gly Glu Asp Pro Thr Ser Ala
            260                 265                 270

His His Ile His Asn Arg Pro Ser Lys Ala Phe Arg Pro Ser Ala Thr
    275                 280                 285

Pro Pro Met Ala Glu Leu Thr Asp Gly Arg Ser Leu Tyr Ala Val Val
290                 295                 300

Pro Asp Leu Ala Arg Leu Leu Cys Pro Ser Cys His Arg Leu Tyr
305                 310                 315                 320

Thr Asp Pro Ala Thr Leu Ala Cys Gly His Ser Arg Cys Leu Val Cys
                325                 330                 335

Ser Gly Ala Ser Asp Thr Leu Ala Thr Pro Ile Gly Thr Ala Ser
            340                 345                 350

Met Thr Thr Thr Thr Ala Phe Thr Phe Thr Pro Ala Val Ala Arg
    355                 360                 365

His Thr Ala Gly Ile Ala Ser Pro Leu Pro Ser Pro Val Val Ala
370                 375                 380
```

His Leu Asp Asn Asn Gln Leu Tyr Arg Thr Leu Ser Ala Thr Ser Thr
385                 390                 395                 400

Thr Ser Thr Pro Ser Val Ala Ser Thr Ala Gln Thr His Ile Pro Val
            405                 410                 415

Asp Leu Pro Asn Leu Thr Cys Pro Asp Ser Ser Cys Asp Tyr Asn Phe
            420                 425                 430

Ser His Leu Ile Val Pro His Leu Pro Leu His Val Asp Tyr Thr Leu
        435                 440                 445

Arg Lys Val Ser Glu Met Leu Gln Lys Ala Val Pro Gly Leu Ala Ala
    450                 455                 460

Trp Ala Thr Arg Leu Ala Ser Lys Asn Asp Pro His Leu Ala Pro Leu
465                 470                 475                 480

Phe Ser Asp Val Arg Leu Ala Ser Glu Ala Pro Thr Asp Val Glu Glu
                485                 490                 495

Asn Gly Glu Gln Pro Met Val Glu Gly Asp Val Gln Pro Gly Ala Val
            500                 505                 510

Ser Arg Thr Ser Ser Gly Ser Gly Gly Asp Glu Glu Thr Ile
        515                 520                 525

Glu Gly His Asp Asp Ser Lys Arg Ala His Lys Ser Arg Lys Ser Trp
530                 535                 540

Gln Ala Ser Lys Lys Thr Arg Thr Val Ser Phe Ser Asp Val Ser Met
545                 550                 555                 560

Ala Ser Pro Ala Val Gly Pro Ser Arg Thr Ser Thr Pro Thr Pro His
                565                 570                 575

Ala Ala Gln Arg Asp Asp Lys His Leu Asp Ile Ala Gly Leu Ser Pro
            580                 585                 590

Ser Phe Leu Thr Asp Leu His Asn Glu Cys Glu Cys Gln Val Cys Phe
        595                 600                 605

Gln Leu Phe His Glu Pro Val Thr Ser Pro Cys Gly His Ser Phe Cys
    610                 615                 620

Arg Gln Cys Leu Ala Arg Ser Tyr Asp His Ser Asp Lys Cys Pro Leu
625                 630                 635                 640

Cys Arg Ala Asp Leu Pro Pro Leu Ala Tyr Phe Arg Trp Gln Arg Pro
                645                 650                 655

Asn Ile Ala Leu Thr Lys Ile Ile Glu Thr Ala Leu Pro Gln Gln Ala
            660                 665                 670

Ala Glu Arg Ala Ala Thr Val Lys Glu Glu Glu Leu Ala Leu Leu Ala
        675                 680                 685

Ser Val Pro Val Phe Val Cys Thr Thr Ala Trp Pro Gly Ile Lys Cys
    690                 695                 700

Phe Leu His Ile Phe Glu Pro Arg Tyr Arg Leu Met Val Arg Arg Val
705                 710                 715                 720

Leu Glu Thr Pro Glu Arg Ser Phe Gly Met Val Leu Pro Leu Arg Ser
                725                 730                 735

Ala Gly Pro Asp Ala Val Asn Glu Tyr Gly Thr Met Leu Arg Val Thr
            740                 745                 750

Ser Cys Gln Met Leu Glu Asp Gly Arg Leu Ile Leu Glu Thr Ile Gly
        755                 760                 765

Thr Tyr Arg Phe Arg Leu Leu Glu Arg Ser Met Val Asp Gly Tyr Asn
    770                 775                 780

Val Gly Lys Val Glu Arg Val Asp Asp Val Ser Pro Glu Gln Glu Ala
785                 790                 795                 800

```
Glu Leu Glu Arg Val Ala Leu Ala Arg Asn Asp Thr Leu Gln Asp Glu
            805                 810                 815

Tyr Ala Asp Pro Glu Pro Val Gly Pro Asp Ser Val Pro Leu Ser Arg
            820                 825                 830

Pro Pro Met Thr Gly Asn Val Glu Leu Ser Thr Asp Gln Leu Met Gln
            835                 840                 845

Ile Cys Leu Asp Phe Leu Thr Thr Leu Arg Ala Ser Ser Ala Pro Trp
            850                 855                 860

Ile Ile Glu Arg Leu Asn Arg Thr Val Gly Glu Val Pro Asn Asn Pro
865                 870                 875                 880

His Asp Phe Ser Trp Phe Ala Ala Glu Val Phe Pro Val Glu Asp His
            885                 890                 895

Val Lys Val Thr Leu Leu Gln Ile Thr Ser Val Arg Glu Arg Leu Arg
            900                 905                 910

Leu Ile Val Phe Trp Ile Glu Gln Phe Arg Ser Ser Trp Trp Tyr Ser
            915                 920                 925

Arg Gly Cys Asn Ile Ala
    930
```

<210> SEQ ID NO 22
<211> LENGTH: 2357
<212> TYPE: DNA
<213> ORGANISM: Rhodosporidium toruloides

<400> SEQUENCE: 22

```
tcctctggcc tctctcgctc cgttcgcctg gccgcgcgcc caaaccgctt tgttgacgct    60
atcagcctcc cgcgagcgct agcaggctct cttagccgcc tcacgcctac ctcgcgaatg   120
tcctccccac ctcgcttcgc gcccggttcg acctcgccca cgcagtcgag gccgcgtgcg   180
acgcacagca gcccaacaca aggtcccttc gcaacgcctg cgcgcccagg tgcgagctca   240
gcggcgcacc aacccgatcc ttcaacctcg acagcaggcg ccgcctccct cctcacgtct   300
tctcctcact acacgacttc gctgcgctct cgacactcgc tttacggcac ggaagaccgt   360
gttgtgctgg atctcggctc gcggatatgg aaggtcgggt tcagcgggga gccgcagccg   420
cgcgagtgcc ggagcgtcgt gagcgagttg gcgcatgagc gggctgggcg aagagcaggg   480
ccgtccatag cgcgcgagagg ggacgacgac gaagaggact gcttttgggc gctcgagaag   540
gccgagccga gcgaggagga gtggttgatt cgcgaggaga gggtgaagcg attactgcgc   600
aagatctggt tcgagtgagt tcaaccggtc tttcttttga taccaggact tgcgctcgcc   660
aacctgggcg gcgcttttctg ctaagaggct cgagtacgaa ccggacaagc ggagtctttt   720
ccgccggctg acttcgttct cccgcagaaa cctcatgatc gacccgaaga cgcgcaaagt   780
catcgtcgtg gagaacccac tgctgtcgac gcgcgtgaag gagatgatcg cgcgggtctt   840
gttcgacaac ttgcaggtaa gccatccgcc gcttcgccag gccgttcacc cgtactgacc   900
gcttcgctac gcagatcccg tgctcagctc tcgcttccgc ccccttgctc gccttgatgg   960
cggccggcac agtgaccggt cttgtggtcg acgtcggaaa cctcgagacg accgttcttc  1020
ccgtgagttc gccttccgct ctcgcctgct tactaaactt gcgctgatgt agagctacaa  1080
caggtctttc acgtcgcccc gctctttccc tccctcacca caactcctcg cgcgggctct  1140
cgcctgaacc gccgcctccg ctctctcctc ctcgcattcg gctcatacgc acctcctccc  1200
tcctccctca actccatgac gcctcccgct atcggacgga taccgaagga gctcttgacg  1260
gaggagctca tagaggagat caagacgcgg ctgtgttttg tcggtgagga ggtcccgctc  1320
```

-continued

```
gatgcgagcc ggggcgagag ggaggcgtcc gcgttcagcg gatcggccat gagcgtcgac    1380
actgcatcag cacgcgacaa ctttgacgac ccttccgacc ccgacaacgc actactaaag    1440
gagctttact cccgcttcgc cgcgacatcg accgccaaac ccgtttcctt ccggataccc    1500
aacttgtccc aacctgcgat cgcgaacggt acaggtcgag ggtggatcca ggtgcccggc    1560
tggatcaggg agcgcgccgc cgaggtgttg tgggaggagg atggtgatgg agacgagcgt    1620
gggcttgccg ccgttgtcct tgactgccta ttgaaggtgc gcaagctgac cacttcgctc    1680
gagcgaagta gctgacactg cacccgttcc cccagctccc ccttgacctt cgaaagccga    1740
tggcctcgtc aatcctcctc acgggcggca ccgccatgct ccccggcttc ttcccacgct    1800
tcaaggccgc tcttcttgcc cagctcgacc gctcgcatcc tccttcccct ccgccttccc    1860
cgcctctgcc agcagcatcc gtcgaacctc cttcttccga ccctgccgga cccatgtcga    1920
cggacacggc ggcatcgcct gcgccctctc gctcgagcga agtcaatgcg aagcggcggc    1980
gaaagcatgc cctcgcgact cgactgcaca acctgcggca ttcgcctcga tacgccccgc    2040
ttgtccctct cgctcgacac ctcgccatct tgaaccaccc atctccgaac tcctcggcat    2100
cgtcgacggc gccctcatca accctcgctc gacagcgcga aggttcggct ccgtctttct    2160
cgcccgcctt gcaaagctgg atcggcggca gcctcgcagg agcgctcaag acgggcgggc    2220
ctgagattgc gagggagcag tgggatgcag ggttgcggtt tgcggaggca gaagaggcgg    2280
agggagagga aggagaggag tttgaggagc gggaagtgat ccggccggct ctgccggact    2340
ggacgaggat cgcgtag                                                   2357
```

<210> SEQ ID NO 23
<211> LENGTH: 2046
<212> TYPE: DNA
<213> ORGANISM: Rhodosporidium toruloides
<220> FEATURE:
<221> NAME/KEY: CDS
<222> LOCATION: (118)..(2046)

<400> SEQUENCE: 23

```
tcctctggcc tctctcgctc cgttcgcctg gccgcgcgcc caaaccgctt tgttgacgct     60
atcagcctcc cgcgagcgct agcaggtctct cttagccgcc tcacgcctac ctcgcga       117
```

| | | | | | | | | | | | | | | | | |
|---|---|---|---|---|---|---|---|---|---|---|---|---|---|---|---|---|
| atg | tcc | tcc | cca | cct | cgc | ttc | gcg | ccc | ggt | tcg | acc | tcg | ccc | acg | cag | 165 |
| Met | Ser | Ser | Pro | Pro | Arg | Phe | Ala | Pro | Gly | Ser | Thr | Ser | Pro | Thr | Gln | |
| 1 | | | | 5 | | | | | 10 | | | | | 15 | | |

| tcg | agg | ccg | cgt | gcg | acg | cac | agc | agc | cca | aca | caa | ggt | ccc | ttc | gca | 213 |
|---|---|---|---|---|---|---|---|---|---|---|---|---|---|---|---|---|
| Ser | Arg | Pro | Arg | Ala | Thr | His | Ser | Ser | Pro | Thr | Gln | Gly | Pro | Phe | Ala | |
| | | 20 | | | | | 25 | | | | | 30 | | | | |

| acg | cct | gcg | cgc | cca | ggt | gcg | agc | tca | gcg | gcg | cac | caa | ccc | gat | cct | 261 |
|---|---|---|---|---|---|---|---|---|---|---|---|---|---|---|---|---|
| Thr | Pro | Ala | Arg | Pro | Gly | Ala | Ser | Ser | Ala | Ala | His | Gln | Pro | Asp | Pro | |
| | | | 35 | | | | | 40 | | | | | 45 | | | |

| tca | acc | tcg | aca | gca | ggc | gcc | gcc | tcc | ctc | ctc | acg | tct | tct | cct | cac | 309 |
|---|---|---|---|---|---|---|---|---|---|---|---|---|---|---|---|---|
| Ser | Thr | Ser | Thr | Ala | Gly | Ala | Ala | Ser | Leu | Leu | Thr | Ser | Ser | Pro | His | |
| 50 | | | | | 55 | | | | | 60 | | | | | | |

| tac | acg | act | tcg | ctg | cgc | tct | cga | cac | tcg | ctt | tac | ggc | acg | gaa | gac | 357 |
|---|---|---|---|---|---|---|---|---|---|---|---|---|---|---|---|---|
| Tyr | Thr | Thr | Ser | Leu | Arg | Ser | Arg | His | Ser | Leu | Tyr | Gly | Thr | Glu | Asp | |
| 65 | | | | 70 | | | | | 75 | | | | | 80 | | |

| cgt | gtt | gtg | ctg | gat | ctc | ggc | tcg | cgg | ata | tgg | aag | gtc | ggg | ttc | agc | 405 |
|---|---|---|---|---|---|---|---|---|---|---|---|---|---|---|---|---|
| Arg | Val | Val | Leu | Asp | Leu | Gly | Ser | Arg | Ile | Trp | Lys | Val | Gly | Phe | Ser | |
| | | | | 85 | | | | | 90 | | | | | 95 | | |

| ggg | gag | ccg | cag | ccg | cgc | gag | tgc | cgg | agc | gtc | gtg | agc | gag | ttg | gcg | 453 |
|---|---|---|---|---|---|---|---|---|---|---|---|---|---|---|---|---|
| Gly | Glu | Pro | Gln | Pro | Arg | Glu | Cys | Arg | Ser | Val | Val | Ser | Glu | Leu | Ala | |
| | | | 100 | | | | | 105 | | | | | 110 | | | |

```
cat gag cgg gct ggg cga aga gca ggg ccg tcc ata ggc gcg aga ggg      501
His Glu Arg Ala Gly Arg Arg Ala Gly Pro Ser Ile Gly Ala Arg Gly
            115                 120                 125 gac gac gac gaa gag gac tgc ttt tgg gcg ctc gag aag gcc gag ccg      549
Asp Asp Asp Glu Glu Asp Cys Phe Trp Ala Leu Glu Lys Ala Glu Pro
    130                 135                 140 agc gag gag gag tgg ttg att cgc gag gag agg gtg aag cga tta ctg      597
Ser Glu Glu Glu Trp Leu Ile Arg Glu Glu Arg Val Lys Arg Leu Leu
145                 150                 155                 160 cgc aag atc tgg ttc gaa aac ctc atg atc gac ccg aag acg cgc aaa      645
Arg Lys Ile Trp Phe Glu Asn Leu Met Ile Asp Pro Lys Thr Arg Lys
                165                 170                 175 gtc atc gtc gtg gag aac cca ctg ctg tcg acg cgc gtg aag gag atg      693
Val Ile Val Val Glu Asn Pro Leu Leu Ser Thr Arg Val Lys Glu Met
            180                 185                 190 atc gcg cgg gtc ttg ttc gac aac ttg cag atc ccg tcg ctc agc ttc      741
Ile Ala Arg Val Leu Phe Asp Asn Leu Gln Ile Pro Ser Leu Ser Phe
    195                 200                 205 gct tcc gcc ccc ttg ctc gcc ttg atg gcg gcc ggc aca gtg acc ggt      789
Ala Ser Ala Pro Leu Leu Ala Leu Met Ala Ala Gly Thr Val Thr Gly
210                 215                 220 ctt gtg gtc gac gtc gga aac ctc gag acg acc gtt ctt ccc gtc ttt      837
Leu Val Val Asp Val Gly Asn Leu Glu Thr Thr Val Leu Pro Val Phe
225                 230                 235                 240 cac gct cgc ccg ctc ttt ccc tcc ctc acc aca act cct cgc gcg ggc      885
His Ala Arg Pro Leu Phe Pro Ser Leu Thr Thr Thr Pro Arg Ala Gly
                245                 250                 255 tct cgc ctg aac cgc cgc ctc cgc tct ctc ctc ctc gca ttc ggc tca      933
Ser Arg Leu Asn Arg Arg Leu Arg Ser Leu Leu Leu Ala Phe Gly Ser
            260                 265                 270 tac gca cct cct ccc tcc tcc ctc aac tcc atg acg cct ccc gct atc      981
Tyr Ala Pro Pro Pro Ser Ser Leu Asn Ser Met Thr Pro Pro Ala Ile
    275                 280                 285 gga cgg ata ccg aag gag ctc ttg acg gag gag ctc ata gag gag atc     1029
Gly Arg Ile Pro Lys Glu Leu Leu Thr Glu Glu Leu Ile Glu Glu Ile
290                 295                 300 aag acg cgg ctg tgt ttt gtc ggt gag gag gtc ccg ctc gat gcg agc     1077
Lys Thr Arg Leu Cys Phe Val Gly Glu Glu Val Pro Leu Asp Ala Ser
305                 310                 315                 320 cgg ggc gag agg gag gcg tcc gcg ttc agc gga tcg gcc atg agc gtc     1125
Arg Gly Glu Arg Glu Ala Ser Ala Phe Ser Gly Ser Ala Met Ser Val
                325                 330                 335 gac act gca tca gca cgc gac aac ttt gac gac cct tcc gac ccc gac     1173
Asp Thr Ala Ser Ala Arg Asp Asn Phe Asp Asp Pro Ser Asp Pro Asp
            340                 345                 350 aac gca cta cta aag gag ctt tac tcc cgc ttc gcc gcg aca tcg acc     1221
Asn Ala Leu Leu Lys Glu Leu Tyr Ser Arg Phe Ala Ala Thr Ser Thr
    355                 360                 365 gcc aaa ccc gtt tcc ttc cgg ata ccc aac ttg tcc caa cct gcg atc     1269
Ala Lys Pro Val Ser Phe Arg Ile Pro Asn Leu Ser Gln Pro Ala Ile
370                 375                 380 gcg aac ggt aca ggt cga ggg tgg atc cag gtg ccc ggc tgg atc agg     1317
Ala Asn Gly Thr Gly Arg Gly Trp Ile Gln Val Pro Gly Trp Ile Arg
385                 390                 395                 400 gag cgc gcc gcc gag gtg ttg tgg gag gag gat ggt gat gga gac gag     1365
Glu Arg Ala Ala Glu Val Leu Trp Glu Glu Asp Gly Asp Gly Asp Glu
                405                 410                 415 cgt ggg ctt gcc gcc gtt gtc ctt gac tgc cta ttg aag ctc ccc ctt     1413
Arg Gly Leu Ala Ala Val Val Leu Asp Cys Leu Leu Lys Leu Pro Leu
            420                 425                 430
```

```
gac ctt cga aag ccg atg gcc tcg tca atc ctc ctc acg ggc ggc acc      1461
Asp Leu Arg Lys Pro Met Ala Ser Ser Ile Leu Leu Thr Gly Gly Thr
            435                 440                 445 gcc atg ctc ccc ggc ttc ttc cca cgc ttc aag gcc gct ctt ctt gcc      1509
Ala Met Leu Pro Gly Phe Phe Pro Arg Phe Lys Ala Ala Leu Leu Ala
    450                 455                 460 cag ctc gac cgc tcg cat cct cct tcc cct ccg cct tcc ccg cct ctg      1557
Gln Leu Asp Arg Ser His Pro Pro Ser Pro Pro Pro Ser Pro Pro Leu
465                 470                 475                 480 cca gca gca tcc gtc gaa cct cct tct tcc gac cct gcc gga ccc atg      1605
Pro Ala Ala Ser Val Glu Pro Pro Ser Ser Asp Pro Ala Gly Pro Met
                485                 490                 495 tcg acg gac acg gcg gca tcg cct gcg ccc tct cgc tcg agc gaa gtc      1653
Ser Thr Asp Thr Ala Ala Ser Pro Ala Pro Ser Arg Ser Ser Glu Val
            500                 505                 510 aat gcg aag cgg cgg cga aag cat gcc ctc gcg act cga ctg cac aac      1701
Asn Ala Lys Arg Arg Arg Lys His Ala Leu Ala Thr Arg Leu His Asn
        515                 520                 525 ctg cgg cat tcg cct cga tac gcc ccg ctt gtc cct ctc gct cga cac      1749
Leu Arg His Ser Pro Arg Tyr Ala Pro Leu Val Pro Leu Ala Arg His
    530                 535                 540 ctc gcc atc ttg aac cac cca tct ccg aac tcc tcg gca tcg tcg acg      1797
Leu Ala Ile Leu Asn His Pro Ser Pro Asn Ser Ser Ala Ser Ser Thr
545                 550                 555                 560 gcg ccc tca tca acc ctc gct cga cag cgc gaa ggt tcg gct ccg tct      1845
Ala Pro Ser Ser Thr Leu Ala Arg Gln Arg Glu Gly Ser Ala Pro Ser
                565                 570                 575 ttc tcg ccc gcc ttg caa agc tgg atc ggc ggc agc ctc gca gga gcg      1893
Phe Ser Pro Ala Leu Gln Ser Trp Ile Gly Gly Ser Leu Ala Gly Ala
            580                 585                 590 ctc aag acg ggc ggg cct gag att gcg agg gag cag tgg gat gca ggg      1941
Leu Lys Thr Gly Gly Pro Glu Ile Ala Arg Glu Gln Trp Asp Ala Gly
        595                 600                 605 ttg cgg ttt gcg gag gca gaa gag gcg gag gga gag gaa gga gag gag      1989
Leu Arg Phe Ala Glu Ala Glu Glu Ala Glu Gly Glu Glu Gly Glu Glu
    610                 615                 620 ttt gag gag cgg gaa gtg atc cgg ccg gct ctg ccg gac tgg acg agg      2037
Phe Glu Glu Arg Glu Val Ile Arg Pro Ala Leu Pro Asp Trp Thr Arg
625                 630                 635                 640 atc gcg tag                                                          2046
Ile Ala <210> SEQ ID NO 24
<211> LENGTH: 642
<212> TYPE: PRT
<213> ORGANISM: Rhodosporidium toruloides

<400> SEQUENCE: 24

Met Ser Ser Pro Pro Arg Phe Ala Pro Gly Ser Thr Ser Pro Thr Gln
1               5                   10                  15

Ser Arg Pro Arg Ala Thr His Ser Pro Thr Gln Gly Pro Phe Ala
            20                  25                  30

Thr Pro Ala Arg Pro Gly Ala Ser Ser Ala Ala His Gln Pro Asp Pro
        35                  40                  45

Ser Thr Ser Thr Ala Gly Ala Ala Ser Leu Leu Thr Ser Ser Pro His
    50                  55                  60

Tyr Thr Thr Ser Leu Arg Ser Arg His Ser Leu Tyr Gly Thr Glu Asp
65                  70                  75                  80

Arg Val Val Leu Asp Leu Gly Ser Arg Ile Trp Lys Val Gly Phe Ser
```

```
            85                  90                  95
Gly Glu Pro Gln Pro Arg Glu Cys Arg Ser Val Val Ser Glu Leu Ala
            100                 105                 110

His Glu Arg Ala Gly Arg Arg Ala Gly Pro Ser Ile Gly Ala Arg Gly
            115                 120                 125

Asp Asp Asp Glu Glu Asp Cys Phe Trp Ala Leu Glu Lys Ala Glu Pro
            130                 135                 140

Ser Glu Glu Glu Trp Leu Ile Arg Glu Arg Val Lys Arg Leu Leu
145                 150                 155                 160

Arg Lys Ile Trp Phe Glu Asn Leu Met Ile Asp Pro Lys Thr Arg Lys
            165                 170                 175

Val Ile Val Val Glu Asn Pro Leu Leu Ser Thr Arg Val Lys Glu Met
            180                 185                 190

Ile Ala Arg Val Leu Phe Asp Asn Leu Gln Ile Pro Ser Leu Ser Phe
            195                 200                 205

Ala Ser Ala Pro Leu Leu Ala Leu Met Ala Ala Gly Thr Val Thr Gly
            210                 215                 220

Leu Val Val Asp Val Gly Asn Leu Glu Thr Thr Val Leu Pro Val Phe
225                 230                 235                 240

His Ala Arg Pro Leu Phe Pro Ser Leu Thr Thr Thr Pro Arg Ala Gly
            245                 250                 255

Ser Arg Leu Asn Arg Arg Leu Arg Ser Leu Leu Leu Ala Phe Gly Ser
            260                 265                 270

Tyr Ala Pro Pro Pro Ser Ser Leu Asn Ser Met Thr Pro Pro Ala Ile
            275                 280                 285

Gly Arg Ile Pro Lys Glu Leu Leu Thr Glu Glu Leu Ile Glu Glu Ile
            290                 295                 300

Lys Thr Arg Leu Cys Phe Val Gly Glu Glu Val Pro Leu Asp Ala Ser
305                 310                 315                 320

Arg Gly Glu Arg Glu Ala Ser Ala Phe Ser Gly Ser Ala Met Ser Val
            325                 330                 335

Asp Thr Ala Ser Ala Arg Asp Asn Phe Asp Asp Pro Ser Asp Pro Asp
            340                 345                 350

Asn Ala Leu Leu Lys Glu Leu Tyr Ser Arg Phe Ala Ala Thr Ser Thr
            355                 360                 365

Ala Lys Pro Val Ser Phe Arg Ile Pro Asn Leu Ser Gln Pro Ala Ile
            370                 375                 380

Ala Asn Gly Thr Gly Arg Gly Trp Ile Gln Val Pro Gly Trp Ile Arg
385                 390                 395                 400

Glu Arg Ala Ala Glu Val Leu Trp Glu Glu Asp Gly Asp Gly Asp Glu
            405                 410                 415

Arg Gly Leu Ala Ala Val Val Leu Asp Cys Leu Leu Lys Leu Pro Leu
            420                 425                 430

Asp Leu Arg Lys Pro Met Ala Ser Ser Ile Leu Leu Thr Gly Gly Thr
            435                 440                 445

Ala Met Leu Pro Gly Phe Phe Pro Arg Phe Lys Ala Ala Leu Leu Ala
            450                 455                 460

Gln Leu Asp Arg Ser His Pro Pro Ser Pro Pro Ser Pro Pro Leu
465                 470                 475                 480

Pro Ala Ala Ser Val Glu Pro Pro Ser Ser Asp Pro Ala Gly Pro Met
            485                 490                 495

Ser Thr Asp Thr Ala Ala Ser Pro Ala Pro Ser Arg Ser Ser Glu Val
            500                 505                 510
```

-continued

```
Asn Ala Lys Arg Arg Lys His Ala Leu Ala Thr Arg Leu His Asn
        515                 520                 525

Leu Arg His Ser Pro Arg Tyr Ala Pro Leu Val Pro Leu Ala Arg His
    530                 535                 540

Leu Ala Ile Leu Asn His Pro Ser Pro Asn Ser Ser Ala Ser Ser Thr
545                 550                 555                 560

Ala Pro Ser Ser Thr Leu Ala Arg Gln Arg Glu Gly Ser Ala Pro Ser
                565                 570                 575

Phe Ser Pro Ala Leu Gln Ser Trp Ile Gly Gly Ser Leu Ala Gly Ala
            580                 585                 590

Leu Lys Thr Gly Gly Pro Glu Ile Ala Arg Glu Gln Trp Asp Ala Gly
        595                 600                 605

Leu Arg Phe Ala Glu Ala Glu Ala Glu Gly Glu Gly Glu Glu
    610                 615                 620

Phe Glu Glu Arg Glu Val Ile Arg Pro Ala Leu Pro Asp Trp Thr Arg
625                 630                 635                 640

Ile Ala

<210> SEQ ID NO 25
<211> LENGTH: 45
<212> TYPE: PRT
<213> ORGANISM: Aspergillus fumigatus Af293

<400> SEQUENCE: 25

Leu Ile Gln Cys Ser His Cys Leu Arg Pro Leu Arg Ser Pro Leu Arg
1               5                   10                  15

Leu Pro Cys Gly Asn Thr Phe Cys Arg Ala Cys Leu Pro Pro Leu Tyr
                20                  25                  30

Glu Arg Lys Gly Ile Thr Tyr Pro Ala Asp Glu Gly Arg
            35                  40                  45

<210> SEQ ID NO 26
<211> LENGTH: 44
<212> TYPE: PRT
<213> ORGANISM: Blakeslea trispora

<400> SEQUENCE: 26

Ser Thr Glu Cys Pro Ile Cys Cys Ser Arg Phe Asn Asn Pro Thr Thr
1               5                   10                  15

Thr Pro Cys Gly His Thr Phe Cys Arg Asn Cys Leu Ile Arg Ser Leu
                20                  25                  30

Asp His Gln Arg Ser Cys Pro Phe Cys Arg Asp Asn
            35                  40

<210> SEQ ID NO 27
<211> LENGTH: 45
<212> TYPE: PRT
<213> ORGANISM: Fusarium fujikuroi

<400> SEQUENCE: 27

Leu Phe Gln Cys Gln Ile Cys Ser Leu Pro Leu Asp Glu Pro Ile Ser
1               5                   10                  15

Leu Pro Cys Gly Lys Ser Leu Cys Arg Arg Cys Leu Pro Gly Thr His
                20                  25                  30

Met Arg Ala Asn Ile Thr Tyr Pro Ala Ala Pro Glu Arg
            35                  40                  45
```

<210> SEQ ID NO 28
<211> LENGTH: 44
<212> TYPE: PRT
<213> ORGANISM: Mucor circinelloides

<400> SEQUENCE: 28

Pro Thr Glu Cys Pro Ile Cys Cys Thr Arg Phe Thr Asn Ala Thr Thr
1               5                   10                  15

Thr Pro Cys Gly His Val Phe Cys Arg Asn Cys Leu Val Arg Ser Leu
            20                  25                  30

Asp His Gln Arg Ser Cys Pro Phe Cys Arg Asp Ser
        35                  40

<210> SEQ ID NO 29
<211> LENGTH: 47
<212> TYPE: PRT
<213> ORGANISM: Phycomyces blakesleeanus

<400> SEQUENCE: 29

Thr Ser His Gly Val Glu Arg Arg Ile Arg Glu Lys Asp Pro Thr Leu
1               5                   10                  15

Leu Thr Phe Gly Pro Asp Pro Cys Lys Thr Ile Phe Gly Arg Ile Gln
            20                  25                  30

Ser Val Tyr His His Ile Ser Lys Phe Gly Ala Asn Ala Gln Ile
        35                  40                  45

<210> SEQ ID NO 30
<211> LENGTH: 64
<212> TYPE: PRT
<213> ORGANISM: Rhodosporidium toruloides

<400> SEQUENCE: 30

Leu Leu Leu Cys Pro Ser Cys His Arg Leu Tyr Thr Asp Pro Ala Thr
1               5                   10                  15

Leu Ala Cys Gly His Ser Arg Cys Leu Val Cys Ser Gly Ala Ser Asp
            20                  25                  30

Thr Leu Ala Thr Pro Pro Ile Glu Thr Ala Ser Met Thr Thr Thr Thr
        35                  40                  45

Ala Phe Thr Phe Thr Pro Pro Ala Val Ala Arg His Thr Ala Gly Ile
    50                  55                  60

<210> SEQ ID NO 31
<211> LENGTH: 74
<212> TYPE: PRT
<213> ORGANISM: Ustilago maydis 521

<400> SEQUENCE: 31

Tyr Ala Ser Ser Pro Leu Pro Arg Ser Pro His Gln Arg Pro Ser Leu
1               5                   10                  15

Pro Ala Ser Ser Gly Ala Ser Val Ala Ser Pro Arg Ser His His Ala
            20                  25                  30

Arg Val Arg Arg Thr Ala Ala Ala Ser Ser Val Leu Ser Thr Ser Ile
        35                  40                  45

Arg Pro Ser Thr Gly Ser Arg Ala Arg Ala Thr Arg Arg Arg
    50                  55                  60

Arg Ser Pro Leu Asp Arg Ser Ser Val Arg
65                  70

<210> SEQ ID NO 32
<211> LENGTH: 29

```
<212> TYPE: DNA
<213> ORGANISM: Artificial Sequence
<220> FEATURE:
<223> OTHER INFORMATION: synthetic oligonucleotide

<400> SEQUENCE: 32
tttactagtg acggcttgt tctctcctg                                      29

<210> SEQ ID NO 33
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 33
tttccatggt gagtgatctg gtgttgttc                                     29

<210> SEQ ID NO 34
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 34
tttactagtg acggcttgt tctctcctg                                      29

<210> SEQ ID NO 35
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 35
tttccatggt gagtgatctg gtgttgttc                                     29

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
ggaactcatc cgctcgatcg                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
caggccttcg ccatcggatt                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
```
tcctcttccg actgggacaa                                              20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
cccaaacaac accgagagga                                              20

<210> SEQ ID NO 40
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 40
aaacactgat agtttttgga agggtgacgc acctc                             35

<210> SEQ ID NO 41
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 41
tcgagctcgg tacccaggag gagaagaagg tgatgg                            36

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
tcgctggatt ggtacgacaa c                                            21

<210> SEQ ID NO 43
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 43
ccaccagtga ccatctcttc g                                            21

<210> SEQ ID NO 44
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 44
aaaggtaccg acttgtccga gcgagagac                                    29

<210> SEQ ID NO 45
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 45
aaaaagctta gactccagaa cccgaccgta          30

<210> SEQ ID NO 46
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 46
tttggatccc gagtctcaat ccctccca          28

<210> SEQ ID NO 47
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 47
tttaggcctg gaggacgggc gatacaactc          30

<210> SEQ ID NO 48
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 48
gtctttcgcg ccctcttcct c          21

<210> SEQ ID NO 49
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 49
cgtaggagat gacgggcttg c          21

<210> SEQ ID NO 50
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 50
tttaggcctc tcgctctcct gcacacttcg          30

<210> SEQ ID NO 51
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 51
tttaagcttc gcatttccag tcccatcgc          29

<210> SEQ ID NO 52
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 52
tttggatcca ccctctacgt cccccttcacc          30

<210> SEQ ID NO 53
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 53
tttgagctca acgcctcgat cctgacttgc          30

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
gtcctgctcg caaccctcac          20

<210> SEQ ID NO 55
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 55
gagacgaagg atggagtggc g          21

<210> SEQ ID NO 56
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 56
cacccgtcct ctccgcttc          19

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
cctcgctctt tcgctggttc          20

<210> SEQ ID NO 58
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 58
cagccacatt cgttcttcag g    21

<210> SEQ ID NO 59
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 59
tggatgatgc ggatattgag g    21

<210> SEQ ID NO 60
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 60
tttccatgga ggacactccc atcgacagc    29

<210> SEQ ID NO 61
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 61
tttggatccc ctgtcccgtc aacttctgc    29

<210> SEQ ID NO 62
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 62
tttaggcctc agccaagttc aagcacaacc    30

<210> SEQ ID NO 63
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 63
tttaagcttc gaccgatctc gaggagacat    30

<210> SEQ ID NO 64
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 64
aaaggatccg gaacgatacc ctccaagacg    30

<210> SEQ ID NO 65

```
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 65
aaagagctct gggagttgcg aggtcataga                                    30

<210> SEQ ID NO 66
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 66
ttgttctcgg atgtgcgatt gg                                            22

<210> SEQ ID NO 67
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 67
ataatcttgg tgagcgcgat gtt                                           23

<210> SEQ ID NO 68
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 68
tttccatggc gactctagcc atcagacc                                      28

<210> SEQ ID NO 69
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 69
tttgatatcg aggctaggcg atgttgcag                                     29

<210> SEQ ID NO 70
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 70
tttactagtc aagatctacg aggcgac                                       27

<210> SEQ ID NO 71
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 71
```
tttgtttaaa cgagtgccca acgactttct ac         32

<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72
cgctgacctt cccaatcttt c                     21

<210> SEQ ID NO 73
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 73
ctttccgacc gacttcttgc t                     21

<210> SEQ ID NO 74
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 74
gaaccgcagg tgaaggtcaa t                     21

<210> SEQ ID NO 75
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 75
tatcggcaag gtacgtctct cttc                  24

<210> SEQ ID NO 76
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 76
caggtttcat cgcaactaca ttga                  24

<210> SEQ ID NO 77
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 77
aacagagcga gttgaagagt agcc                  24

<210> SEQ ID NO 78
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 78
gcgacgacta cgtgaacctg                                               20

<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 79
cgatggggaa ggagaatttg                                               20

<210> SEQ ID NO 80
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 80
gcacactgca cgccttactc                                               20

<210> SEQ ID NO 81
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 81
acgagctgaa gagcctgtcc                                               20

<210> SEQ ID NO 82
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 82
gcaagatacc ccagctcgac                                               20

<210> SEQ ID NO 83
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 83
ggggacgttg acgtagaagg                                               20

<210> SEQ ID NO 84
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 84
ggctggatga aggagtggac                                               20
```

<210> SEQ ID NO 85
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 85
aggaggagcg tgagtggaag                                                    20

<210> SEQ ID NO 86
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 86
atgggactgg aaatgcgaac                                                    20

<210> SEQ ID NO 87
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 87
gggagacgaa ggatggagtg                                                    20

<210> SEQ ID NO 88
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 88
tcgtgcacaa cccgaactac                                                    20

<210> SEQ ID NO 89
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 89
atcttgcgct ccttctcgtc                                                    20

<210> SEQ ID NO 90
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 90
accagcttca gaccacgtct c                                                  21

<210> SEQ ID NO 91
<211> LENGTH: 21
<212> TYPE: DNA
<213> ORGANISM: Artificial Sequence
<220> FEATURE:

```
<223> OTHER INFORMATION: synthetic oligonucleotide

<400> SEQUENCE: 91
agaagttgga ggaagggatg g                                              21

<210> SEQ ID NO 92
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 92
cgacaacttt gacgacccct c                                              21

<210> SEQ ID NO 93
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 93 caggtttggga caagttgggt a                                             21

<210> SEQ ID NO 94
<211> LENGTH: 597
<212> TYPE: DNA
<213> ORGANISM: Ustilago maydis

<400> SEQUENCE: 94
gattagatct tgctgatagg caggtttgct tggagaatgg ggggaaaaga ctgaccgaag     60
aaacagcgag atctagaagt gataagcgga agaatctga cttgctgtga tcagcagcca    120
attttttttt cgtttttttt ttttcactcc acatcgtcgt gcgtgcacgg tctgcatgtg    180
taaattgtat tcatcgaaag ccacagttga atacatcagc ccgatgtgga tttcgaaaac    240
caattaatct tggaattcac gcgctcagat cagtccatag agtcgacttc ggctgtttcc    300
aagagcttct tctctgcgag gtggttgccc gtgtttctcg ctgggaaaaa aggatcgatt    360
attattcgct tctacctcgc tcgcacccct tggcctgctga aggaaacagc gccgagactc    420
ggtcacggtt gctgggctcc gtgttgatgc tgggacggcg caaagtgggg cccgcgcact    480
cttcgagcca aggacctcac tcttcaagaa caagcgctgt cgccatcgtc ttcttctttc    540
tgctccacca tcgaatcttt cttttctcgtt tcgaaaccaa acactcttc caccatg      597

<210> SEQ ID NO 95
<211> LENGTH: 1434
<212> TYPE: DNA
<213> ORGANISM: Rhodosporidium toruloides

<400> SEQUENCE: 95
ctgcagaact acgccctctc acacccaact tccgactcga ccggcggtac gagcacgacc     60
tacttctact gcctgccatc gacatccggg cgggtcgctg cctaccctgt gcgttctgcg    120
ccctccctcg tctcgggagg cagtgtctga cagaagcttt gcgcgcagta ccccgtcaag    180
atgcaactct acgcaacgtt cggcacagaa gtcgccaagc tccgcgcatc gccgcctcaa    240
gctctcgcgc tgcccgacgg tgtcgtctat tacgaggcgg agaagctcga gttgccggct    300
ttgccagcgg cggtcaaggt tgaggtgag acgagaagg cggagtagc gggggaggac       360
aatgaggcga agggtgagat ggtgctggtg gagactctta cggtggagca ggaggagatt    420
```

```
gaattgggct cgggagtcgt gcagattgag gagtcgttgc tcgtcaagct ggaggtcagc    480
ggctgatcct tccgttcgtt gcaaggatcg tctgcatgtt tcgcttctct caatgacaca    540
acctggagag cgctcccgtc agcgagaatc gaggacattc cgcagctcgt gagcaagcgg    600
aggtgcgagg ctccctcgaa agctgcgcct cttgttctct cctgctctgg                660
tgggctggcc tgacatgtaa tgtgctccgc cgcaagtccg tcgtcggtct caattcgacg    720
ttgaaagggc atagcgcaag gaagaaccct ctgcggacat gcagaattac tggctcgcct    780
gctccttcgt ctactggaat aagtcctgtc tcgttaaagc cccaacgtcg tttttcgacg    840
tttgtaaggc gcaagaggtg ctatgggcta cgcaggaagc tgagaggaca tagaagtcgg    900
gggaggaacg gcgcagagcg gcagttgcgg aagcatgagg aaagcgagac ggtccagcat    960
ctgcagcgcc aatccgcaat ctcctggttg agcctgcacc ggaagcgtcg gaacagtatg   1020
cgcagagtcg aacgcaagta agaaagacgc accctcacac tcgcttactt cgagccatac   1080
aacggatcaa agctgcgcgt atctcggctt gtaagggccg gaaagcaacc tcggagatgg   1140
acacgtcaca tcaccaactt atcgatctcg gccgtcgacg tcgcagagag ggcgagagaa   1200
gcggtgaagg agggaaacaa cccctcgaga gcatgatccg accgaatctg cagcgcagga   1260
agccgttaca agcccgcctc gagcgcaggt cgggtccagc cggggacga aacgcgcgag     1320 gctgattcgt gagcgaagga agccgcatcg acaagttcgc tcccctttgc cctctttccc   1380
atcacccgtt ctcgccttac ccgctcagaa caacaccaga tcactcacaa tgtc         1434

<210> SEQ ID NO 96
<211> LENGTH: 888
<212> TYPE: DNA
<213> ORGANISM: Aspergillus nidulans

<400> SEQUENCE: 96
ctgtacagtg accggtgact ctttctggca tgcggagaga cggacggacg cagagagaag     60
ggctgagtaa taagcgccac tgcgccagac agctctggcg gctctgaggt gcagtggatg    120
attattaatc cgggaccggc cgcccctccg ccccgaagtg gaaaggctgg tgtgcccctc    180
gttgaccaag aatctattgc atcatcggag aatatggagc ttcatcgaat caccggcagt    240
aagcgaagga gaatgtgaag ccaggggtgt atagccgtcg gcgaaatagc atgccattaa    300
cctaggtaca gaagtccaat tgcttccgat ctggtaaaag attcacgaga tagtaccttc    360
tccgaagtag gtagagcgag tacccggcgc gtaagctccc taattggccc atccggcatc    420
tgtagggcgt ccaaatatcg tgcctctcct gctttgcccg gtgtatgaaa ccggaaaggc    480
cgctcaggag ctggccagcg gcgcagaccg ggaacacaag ctggcagtcg acccatccgg    540
tgctctgcac tcgacctgct gaggtccctc agtccctggt aggcagcttt gccccgtctg    600
tccgcccggt gtgtcggcgg ggttgacaag gtcgttgcgt cagtccaaca tttgttgcca    660
tattttcctg ctctccccac cagctgctct tttcttttct cttctttttc ccatcttcag    720
tatattcatc ttcccatcca agaaccttta tttcccctaa gtaagtactt tgctacatcc    780
atactccatc cttcccatcc cttattcctt tgaacctttc agttcgagct ttcccacttc    840
atcgcagctt gactaacagc taccccgctt gagcagacat caccatgg                 888

<210> SEQ ID NO 97
<211> LENGTH: 617
<212> TYPE: DNA
<213> ORGANISM: Aspergillus niger
```

<400> SEQUENCE: 97

```
gtcgacgaga tcgtaggagt gagtacccgg cgtgatggag ggggagcacg ctcattggtc     60
cgtacggcag ctgccgaggg ggagcaggag atccaaatat cgtgagtctc ctgctttgcc    120
cggtgtatga aaccggaaag gactgctggg gaactgggga gcggcgcaag ccgggaatcc    180
cagctgacaa ttgacccatc ctcatgccgt ggcagagctt gaggtagctt ttgccccgtc    240
tgtctcccg gtgtgcgcat tcgactgggc gcggcatctg tgcctcctcc aggagcggag     300
gacccagtag taagtaggcc tgacctggtc gttgcgtcag tccagaggtt ccctccccta    360
cccttttttct acttcccctc ccccgccgct caacttttct ttcccttttta ctttctctct    420
ctcttcctct tcatccatcc tctcttcatc acttccctct tcccttcatc caattcatct    480
tccaagtgag tcttcctccc catctgtccc tccatctttc ccatcatcat ctcccctccc    540
agctcctccc ctcctctcgt ctcctcacga agcttgacta accattaccc cgccacatag    600
acacatctaa accatgg                                                    617
```

<210> SEQ ID NO 98
<211> LENGTH: 388
<212> TYPE: DNA
<213> ORGANISM: Ashibia gossipii

<400> SEQUENCE: 98

```
cactatacgt gcctcgtccc cgccgggtca cccggccagc gacatggagg cccagaatac     60
cctccttgac agtcttgacg tgcgcagctc aggggcatga tgtgactgtc gcccgtacat    120
ttagcccata catccccatg tataatcatt tgcatccata cattttgatg gccgcacggc    180
gcgaagcaaa aattacggct cctcgctgca gacctgcgag cagggaaacg ctcccctcac    240
agacgcgttg aattgtcccc acgccgcgcc cctgtagaga aatataaaag gttaggattt    300
gccactgagg ttcttctttc atatacttcc ttttaaaatc ttgctaggat acagttctca    360
catcacatcc gaacataaac aaccatgg                                        388
```

<210> SEQ ID NO 99
<211> LENGTH: 963
<212> TYPE: DNA
<213> ORGANISM: Rhodoturula grammis

<400> SEQUENCE: 99

```
ggcgcgccta cgtctacgtc aagggcaatg ccgacgtgac caaggccatc ggccaggacc     60
tcgccttctt ctcggtccct gtcgagctcg gcgtgcgtcc cgccgctctc tctctctctt    120
tctctcggcc gcgcctcacg tgatccacga cgtcgtactg acccttgcga atgtgcgcgc    180
ccgcagccca acggcgtcga aaggtgcac ccgctcggcg acctgacggc gttcgagaag     240
gagctcctcg aggcgtgcct cggcgagctg cccgggtcca tctccaaggg cgagtcgttc    300
atccagggct ccaagctctg actgccggc gcatcgacgg gcgcgagcca caaggcgagg    360
atgtgagagg aggcgtttcc tccaccttgg accccatctg ccgcctccct ttctctctct    420
ttcttccct tcctctctct ctctctctct ctcgttctcc tccttctggg cctctcggac    480
ctcttcctcg ccgtcgactc gtgaaaatgc agtgcgcgtt tctgtacctt gtcctgcgag    540
agagatctgg ttctgcgagg gtgagtcgtt gccttggccg tggcacgcct cgccgcagcg    600
agagagaaga ggccacggtc caggacgacg acgacgagga ggaagcgcaa aaggcgagac    660
accgagtgcc atcgattccc cgctcgaacc tgctcacggc tgtcgaaggc ggtgcgccac    720
ggtgcttgcg ggagcgaaag caagctggcg tcgtcctctt gaactggttc gagtccgtga    780
```

```
gggcggcgac gagaactcag gcgaggtgct cgcgtcggaa caagccgggc ttgtggtcga    840
gggagcgaga gcgaggcagc gccgtcgtcg ccgaggcaag agcggcatcg acaagttggc    900
ccgtcgcctc tcgctccctc ttctcctcct cccaccacca cctttctcca gctcgaacca    960
tgg                                                                  963
```

<210> SEQ ID NO 100
<211> LENGTH: 1009
<212> TYPE: DNA
<213> ORGANISM: Sporobolomyces roseus

<400> SEQUENCE: 100

```
ggcgcgccga agttatacct cagaggtctc aaaaacgaaa aagtcatgca agaatctcct     60
ttgacgtgag ggttatttct cttcctctag tagtctacga gaatcgcaaa gatcggaaaa    120
ctgatgcatc tttgtgttca cgggttagcg atttgatctt ttcgattccc aaaatcgtat    180
cgttcctgtc gcagggaact acgctcaaag ccggcactct gatcatcacg ggagtgagtt    240
ttgagctctc cctctatgag agtgcaaggt tcgtcgctga tggtgtaatc cgctcatgcc    300
ttcccctcta ccttctcctt tgtccattct ctctactacg gttgtcacat cttccttctc    360
cgacagaccc cgcacggaat tggagcgtac tcgaatcctc cggaattctt caaggacgga    420
gacgtcttca gggtcgagat ctcggggaggc atcgggagtt tggtcaacaa gatcgaatat    480
gaaaagtaga taatccgtta ctcaggtcaa tggtatggct tcgaagatgc tggaatcagc    540
cggaaagcaa agctggagag aaaaatcgag attgcgaaac gtgcgatgtc atttcgtttc    600
gagctcgcaa ccatctcgta tccctctgag ctacatacaa acgtcactac ggcctcggag    660
tgactccctg cgagcggatt gaaggagatc acggtcgaat cagctagacc ttcgcaacgt    720
tttcgcgctc gcacgttctt atcgatctac tgagattgac tcgaaaaagt cttctctcac    780
ggtcgattga actttgaatg aactctcagg ttgcgcgaga gccaatacga ccgaccaga    840 ggcaattcgg agcttccgg aacgttccaa ggagagggat tttccgagag attacgattg    900
cgagatagaa aaaaggctag ctttcgattt cgagagagat tactttcaag ttcgctgctt    960
ccaactcttg ctccaacccc ctccactcct tctctacaaa acaccatgg              1009
```

<210> SEQ ID NO 101
<211> LENGTH: 2148
<212> TYPE: DNA
<213> ORGANISM: Rhodotorula glutinis ATCC 204091

<400> SEQUENCE: 101

```
ggcgcgccac catctcctcg tcgcttcttc cctctccttc ggcgcccaca ccgcttcgca     60
gggctcacgg actgctcaca tcgtttgtgt gcgtcgctgt gcatgtccac gcaccactcc    120
cagcccccac gagcgcctca aaagacgcgg acgcagacgc ccgccgaacg acggcacgcc    180
cctcttctca ctagcgcgac gaaccagctg cgacgattcg tgcgcttatg ttagccggac    240
ttctggcttg cttttgcgctg ctgcgtccgt cttgtggtgc ggatcggctc gatgggggtt    300
tgctcgtttg ctgggagacg gtcgcctctc cctcctcctc ttcactcctc gttagctttc    360
tacgctcatt ggtctgcga accatctaca tcacgctcgc tcgtcatgct cgtactacga    420
tcaacacccc tgctcgtcgt gctttccctc ctctccgtcc tctcggccgc gtccagcgac    480
ttgcccagcc aacttccccc gcacgccggt gagtctccca cacttccttg cgaccccaac    540
ccagcatctg acatccgcat cacgcagccc tcccgccttc ccactcctcc ctcttcaccg    600
```

| | |
|---|---|
| actcctcctc ctcctcccct gattcctcgt ccctcaaagc cccgcagcct cttcccttca | 660 |
| aaatcaagcg cccccgctcg ctcgaacaag tgcagcagaa cctcgggaag aggctggcga | 720 |
| agcgcggcga ggaggggagt aagacggaga gggtgccgtt tggtcagagg agtgcgacgg | 780 |
| cggcgagtgc gggtggacaa ggtggagcgg ggacggggag ggcgacgcag cgcgttacgg | 840 |
| gcggaggaag cagaggtgca ggaggaggcg gagggagtgt cgcggctgct cagcctgtcc | 900 |
| cttcgactac ccagacggtc gagacaggct ctaagatcgt ctcgactggt cttctgaccg | 960 |
| tagcgtcgcc gtcgacggca gatggaggag gcgggacggt cacccaggtc gagacggcct | 1020 |
| cctcaggggt attgatcacc agcacggcg gagcggcgag ttcagcggcg cgtcggacg | 1080 |
| tcgctagcgc acaggcagcg gaggcgacgt cgagtacgag catgatcagc ggaggagcgg | 1140 |
| cggctggcgg gagtttaagc aggatgctgg cgggaggagt tgcgggtgca gccctgatcc | 1200 |
| tcctcgtgcg gtgagcaggc gaagcgagga gctcatgtag atacagcata gacagtatat | 1260 |
| atcgccagga tagcttgcaa cagccgccgg tcggtttatt ccattgtcct cgaccccatg | 1320 |
| cgaaggcgag ctctgctcgt cagctggcca agctggccag cagacgagcg ttggggtggc | 1380 |
| ggaacgccaa cggcatggag taaagcagcc gtgaggatga cggaggagct cgggcgaggt | 1440 |
| gatgggatt ctagcaggaa cagcagagcg cgcgaggagga gaggaaccgg aagcacagtc | 1500 |
| tcgtggccgc ttgttgcaga tcccagtgtc gctagagtgc tcgtcgtcat cagagcgagt | 1560 |
| gaacaaagcg atgccctgaa gaacgatgag cgaatgagtc gaagcggcgt ctaccggtga | 1620 |
| actcggggtg tggcaaatga gcgagacgag gagtgcccgc cagagttgcc acgtcgaccc | 1680 |
| cacgtcggaa tcgacgttga tagagtgaac gaagccattg cagaccccag aaggtggcca | 1740 |
| tgttgtggaa gcgagggcag gagcgagggg agaaggcgag gaggaggagg ggctggggaa | 1800 |
| gcccgtccgg gaatggcgca gctgggtgcc ggggatgtgc gcgagtggcg gaggagtcga | 1860 |
| gcgtgagagt tctggaacac ggggcgcgca aagggtcga gggccgtgac gagttcgccg | 1920 |
| ggcggtggtc gggctgaggg cgagcgcgcg ttggggacga cgacgcccga cgccctcgct | 1980 |
| cttcgtcctc accgcttccc ggagaacttt gctgtactct gcttctccct tcacactctc | 2040 |
| acacccactc acacacccctt ccatccacac acaagctatc cgcacacctc tcacacccga | 2100 |
| ccccagctcg ccccatcctc ttcgcacccg gctcatcgaa aaccatgg | 2148 |

<210> SEQ ID NO 102
<211> LENGTH: 1015
<212> TYPE: DNA
<213> ORGANISM: Rhodotorula glutinis ATCC 204091

<400> SEQUENCE: 102

| | |
|---|---|
| gtgcgagaag aagcgaggca cgcgaagcgg tagaagcaat gaagcgaggc gagagcgaga | 60 |
| gaggcagggc ttcagccatg tccagctgat cggctgtaac gtcgcgccgg gccagtctgt | 120 |
| tgaatttgtt gcgtcgcctg agcgtaatag aagtgcagta gtctactccg catgccgaga | 180 |
| acgtcgaaga gcgcgaagta gggagtcgag ggaagcgagg gtggcaaaca cagcaacgac | 240 |
| aagcggttcc gcttcgctca aaagctcgtt gacgttgttt tgacgttttg aagacagtac | 300 |
| aacagcagca agaggcgtgc gaagcgttgg tggcgagagc agcgacaagg agggaggaat | 360 |
| gagggagtgg tggcgagggc tcgcaaacgg gcgtacgcct cgaatggaga cgtgcgagtc | 420 |
| gttcttcgac gtccgaggga tgccgagcgc cgagacggag cacgcaacga gcgagaggag | 480 |
| agcagccgcg caaggtgatt cgagtggcgc aagcggagga cgacgaggag acggacgagg | 540 |
| gaggaggagg gatggcgagc gagcatcgga cggcggggcg cgagagacgg cgtgaggagc | 600 |

```
cgggtgtgga gagtttgagg aggcgcggga tgcgaagtgg ctgggtgtgc ggagtgagcg      660
gtggcaaaga gcgcacttag agtctagagc gaggcagtag tagtagagct gtatgaatga      720
atacaaagtg tgaatacaac agtttgtaat gcgattctga gcttggacgt gtgcgcgcga      780
gagggcgact tgcaagccag cgcccgctcg ctcttcttcc ttctgcacct cgcgtcaacc      840
ctcgcatctc acacctacac tcgcattcaa agtgcgtaca ctctcccacg acacacgggg      900
acggcgcaca ccaccgcgcg tcgcttgaac ggcgtcgcca cttcgagccg tcactgactt      960
cgtcctcgtc ctccctcctc tactctcttg tactgtactg tgtactgggg gggaa         1015
```

<210> SEQ ID NO 103
<211> LENGTH: 944
<212> TYPE: DNA
<213> ORGANISM: Rhodotorula glutinis ATCC 204091

<400> SEQUENCE: 103

```
catgctgctg ctgcccctca aaggtcctct cgtccacgtc cgacgagtct ggacagcttt       60
cacagtcccg agagtgcaag agcgaggcgg gctcacggtt ccgcaaagga gcgcgaggtc      120
cgaccgccgg ccggtctcct tgcccgcctc gcctcacctc ctcttgcagc aggttcacct      180
cttcgaggtc actcgatcgc tcgcagcgat gcgcaggtac aagtacgcta ggcgagagcg      240
tcgaaagcgg ggttctgcga gggactggac gctgcagagc gcggtcgaga gaggctcgag      300
tggcgctttg accgctcgac gcaaggcatg cgctcctccg tttgagctcg cagatactgc      360
cgtgcgaaga cgagcatagg ctgtggctgc ggtagcaagg agccggcgag agaaagctgt      420
gctcgagcag gacgagagac ggtccgcgcg cttgagaagg tcgaggtgag gcgtcgcaac      480
cgggttggat ctcgattctc ggcgaactac ggcttcggcg agggccaaag cgacggcagg      540
ccgcgcaagc tggccaggcg agagcgcgag agtcgcgagc tgaagcgggc gcggggtaga      600
gcaagctggg gaagcgagag agggagagag agagagtgag ggggtggcga ggtggagacg      660
aggcgagcgg ttggcttgcg cgcgcgcgag agggatcgag gcgagaggcg agccccgaga      720
gtggaaggaa ggacgaggaa acctgcgtgc ggaggcgccg cgcgcgcgtg ccacctggct      780
gagcacgggc ccgagcttga gggagctggg ggcgcgcgag cgagacgagg gcagggcgag      840
cccgcgcgtg gcggccgcct cgcaacccaa ggctcgccct ggccgccgct cttgctctct      900
ttcctccacc ttcgcgtctc accactcgaa tctcacttca tcca                      944
```

<210> SEQ ID NO 104
<211> LENGTH: 1462
<212> TYPE: DNA
<213> ORGANISM: Rhodotorula graminis strain WP1

<400> SEQUENCE: 104

```
caaagggaga ggagcgggcg gaggatggtg gtgccggaca gggcgagagg gaaggtcgag       60
ggagagatgg gagcgcgaaa ggtcgaggcg gggagaggga gggtggggtc gggaccaagg      120
gggcagagag gctcacaagg acggaggagc ttactccgcc ttgaccttgc gggtggcggt      180
ggtgccctcg cggaagctgc ggcgcgagga aggtcgtcag ggccgggccc aggggaggaa      240
cgaggacggc gacgacgacg cacccgttct tgaagcggcg cgagacgccc ttcaggtgct      300
gcatgcggcc agtgccagtg gtgtggcggc gcttggcctt ctgtccccac tcgtctgcgc      360
ggcgagggag aaggcgaggt gagcacgacg gcgcgcgagg gccggacgag gctgagaggg      420
ggacgcacac gagcggagct tggccgcggg gtagccgcac gaagcgcacg acttgtgctg      480
```

```
cttgtggaac gagcggcggc cgcagcgacg gcacagactg tgggaccacg agggtcaacc      540
gggtgctcgc gagacaggag cgcggcttgt ctcgaagcac gggcaaagag agcgttggac      600
gcacgtgtga ctcttggtgt ggcggagacc gaacgaggtg gtaccttcg tctgtggggc       660 gcaaggagga gtgggtcagc gtcgggcctc gaggcgcctg ggtcgtcgac ctcgcccgct      720
cccgatcctc gcgccgtcct gctcctcctc tctccaaccc tgcgacgtgt tgcggcagca     780
gcagcttgct gggacatgtg gggagggcgg caaggcgagg ggaggtcgag gtgcgaatgt      840
gggtggtcgc gcttggcggg gcagcatgtc gtcgcggcct cgagccgggc gggcgacctg      900
gtggccgggt cgagcgagag gcgtgggagg gagtggcgca aatggcgtgc gctcagaggc      960
gggttgtcga ggcgtcgagg cggacgaggt cgaggaggtc gaggtgggaa gctgctgctg     1020
ctgctcgggc gtcgtcgccg cgtcccgagt gccccgtgcg cgcccctgct gccgctcctt     1080
gggccgtcct ggtcccacct gcccgtgccg tcctccacga gagcgcgagt ggggctgtgc     1140
gccgggttgc gctccaactt tgcgagagag cgaggacggg ggcatggctc gctcgccggc     1200
ctcgggtcgt tcgaggggtc gggggcgggt tgcgggaggg tggtgcgagg tggcgggctt     1260
accattgtcg cgtcggagag gggggtttgg cctgcgagaa gacgaggaga cgagaggccg     1320
ggggaggcga ggcggcgagg cggcgagacg gctcggacca agcgcgcgcc gccaaagtct     1380
gcctcgccgc tcgcgctcgc ctccctcttg ctctccacct cctcctagga ccacaaaggc     1440
acccttgtgt aggcgtaggt ca                                              1462

<210> SEQ ID NO 105
<211> LENGTH: 1315
<212> TYPE: DNA
<213> ORGANISM: Rhodotorula glutinis ATCC 204091

<400> SEQUENCE: 105
tgagcgggcg agccgcgagc gaggagcgtt gaggaggaag ggagggaggg aggagggaga       60
gggagggagg ggaccccccat ctttctattc attcacaaag acgacggtgc ggaggggtcc    120
ctcgagtgtt tgggctgggc ttcggagtct cgtagcgagc aagtagtgtt tctctccgtt     180
tcgacagctc gtattgtcat ttcttgttca ttgtcgtttc cggcgactgc aggtacgctg    240
attttcggcg gagacgacaa gcacgtgggt tgtgagcagc gagttgagca agaaaaagcg     300
gacgaaggcc ctcgtcgggg gcttcaagtc aagattctgc ggagattctg cgagagactg     360
caagcgttga acctgttgag atctcgtcgg acgacagcac agtgtccgtc tcgctcaatg     420
cgataggaag cgagagagag gaggaggata tcggaggaag gcgtgtttgc gttcgctcca     480
ggcgtcgcaa gatccggcgt agagcacaat cgtcgttggt tcgacgtttg tagttcgtca    540
cgagtgaggg cgaagcctgg caagcaaaga aggggacgag cgactcggca gctatcgctg     600
gaggagggcg actttgtggc ccgtttccgt cgagctcgac gcgagtgagc gcagggtcgg     660
tccgaaccga tgccatggac gcagtgagcg aggccggatg tgcgatgctg tttcaagcga     720
gcgaaggaag ggagaaagcg agcgagaggt cctcctcctg tcttcctcac gccttccgaa     780
ggccgacaag aggcgtagac gtcgacgagt caacggtttg acgtcgctca ggcctgtagc     840
gggtcgtcgg aagctgggaa agagaggaac caacgagtaa caagcgcgag agtctcctca     900
aggcggacaa ttgcctcgct tcggtcccgg tcgagctctt ccagtaccag cgagggcgaa     960
agtcgtcgat gcgtgcgcat ccaaggccaa gcgtcgcagt cgagaagagc gagagtgaag    1020
cgagtgaagc gggagagtga gagcgggtaa tccgcgtact tacgagtggg ttgtattcct    1080
tcttgtaatg gcagattacc tcgattggcc acgtcacgtt ccgggagtgc ccgggcgtgg    1140
```

| | |
|---|---|
| gcaaaagggc gagcgcggcg cctctctctc ttgcttcctc agcagagcag ctctcccctc | 1200 |
| gagtacgtcg acgggctcac tacagctagc aacagcaagg ctaccacgcc agctacacgc | 1260 |
| cagctcaccc aactcacacc gctcgttgtc gccgcgcgcc gcaggaaaac tttgt | 1315 |

<210> SEQ ID NO 106
<211> LENGTH: 1497
<212> TYPE: DNA
<213> ORGANISM: Rhodotorula glutinis ATCC 204091

<400> SEQUENCE: 106

| | |
|---|---|
| gctcatcatc gagcgagggc agcagcgacc tgcggactgg ccgaagaact tccccggcca | 60 |
| gcgcttcgag gacaaggaca ttcgcacgcc tcgctctcag tggcggtaca tcaagctggc | 120 |
| gaccacagac gacctctcgc cgactgagga gaacacgacg tcctgcgccg tccgtacgg | 180 |
| cgaggactcg cagctcgcca tcttccacgt tcccggcaag gggtacttct gcacgcagca | 240 |
| gatgtgtcct cgtgcgtcgc gcctgctctc tctttctta tttgctggct gactcgtgct | 300 |
| gactcgcccg aaacctcaga caagcgcgcc ttcatcctcg agcatggcat cgtctcggac | 360 |
| gacgggagtg gccacctcta cgtctcctgc ccgctccaca agcgcaactt ccgcctcgac | 420 |
| aacggcgact gcctcaacga cgaggagtac aagatcctcg cgtttgatgt caaggaggag | 480 |
| aacggcgact gctcgttca ggttcctccg cctgacgagc tcgacgcttt gattgggtgc | 540 |
| gtctcgctta gccctctctc aaagacctga gctgacccctt ctgattgtcc gcagctcgtc | 600 |
| gaagtggatg tgcgcaaag cgaccgccga agccttcggt cgcaacgcag cgacagccat | 660 |
| cgagtgcgtc ccctccaagc ttctgttttc cgcgcgcaca ctaggctgac gacaagtctc | 720 |
| tgcaggatcg tcggaccgtc aggcgaggtt gacgaggaca agaaggcagc gggaacagag | 780 |
| tgcggcgaag cggataagtc ttgcgggacg cacaagctcg agtggtgatt cttgcgggtc | 840 |
| cgtcacagcc aatgtatcta tctctagatg tccttctcgg gtatatcagt tgttcgtgca | 900 |
| tcgtagacgt cgtttagcag ctctcgttca gccacttgcg aaggcccgct tcttcgacga | 960 |
| caaggacggc ttcgcttcct ttacctcgtc gtctgagcgt tctcaaggga ccctcctacg | 1020 |
| cccttcttcg cacaggagcg gccgacgagg cagccttgct ggcttatcgt cgcttccgcc | 1080 |
| tttcatgctc gagcaagtcc tcctgcgagt gtcccgacgt cggccgcct tgcccaaggt | 1140 |
| cgccgactgt cctatcgcga cactgcgaat gcactgctgt ccgcgccgga gactgtgcgg | 1200 |
| cgcgaattga gggcaaagtc gtgcatttgc gaaacggtat ccgctcgaag ggcccacgat | 1260 |
| agacctccac cggcctcaaa cttggcgaca gggtcgcttc cgacggcgga cagcaagtta | 1320 |
| ggctttggcg tcgtcgctgc gatccgcttt gcgggacccc ttatcgcgac tgccggattc | 1380 |
| gattggcgat atctctcgct cgctggcctc gctggacagc tggacagtct ctgcagcgtc | 1440 |
| gaagcgacgt cgataaagtc agcgacgtcc tcgcgaacca agaagaatca cccgccg | 1497 |

<210> SEQ ID NO 107
<211> LENGTH: 1594
<212> TYPE: DNA
<213> ORGANISM: Rhodotorula glutinis ATCC 204091

<400> SEQUENCE: 107

| | |
|---|---|
| cgccagggaa cgcagagaag gcgggacgag cgagggtgag tcgcgcaagt cgacgaagaa | 60 |
| gccgaggtca acgtcgaggg ttgtcaagtt ctggcagacg gacagcagcc acactaatcg | 120 |
| ctgccgactt ctgatgcatc gtcgcgcggg tgtcagctcc tagccgtgga aggaggaagc | 180 |

```
caggacgttc tcaccgggcg acgcattgct tgtgccagac ctcgaggcga gcttgtcgcg    240
tcgaaagacc ggcgacctcg tccggctcaa attccagccc gagtgattgc cctgacaaca    300
aaggcgaaaa gctgaagccg gtaccaaagg tcggtccatc gaaagtcgcg ctccgaagac    360
tggcgtcgac ggatctgacc atcgctgccc ctcctgcgtc tgctttgagg caccttacag    420
cctgctcgtc tcgttcggag cctccgcatc cgcttggcag gaccacctcg cgaccagtga    480
cctcccttgc gatggctcgc caagtcttgc atactccggc gacgttgcgg aaggcgcagg    540
tggggcagga gatgcggagc gttgtgaact gtccgttgac gaggagtgtc ggcgaaagaa    600
gggcggtggt gagagagtag gtgaggatct tgaggaggag ttcaggagga agtgaggaaa    660
ggtctgccgg tgactggtaa ggctgaagca tgatggcgag tgtagccaag tgatccgagc    720
gacgatcaag agacgaagga cgagacaacg cttcagcgcg cgaagagagc gagcgaggac    780
cctcctggtc gagaggctat ccagtcgcca accggtaccc atccagtttg cagggttgaa    840
acacagctga gaggatcagc gagtggtagc gcaaactcct aaggcgctga acgtcaagga    900
cagcgagcgt gagcgtgtgg aagcgacttg cgaaggccaa actcgtgtcg cgctggccaa    960
ccgccgtgcc gctttgacgc gcttctgcgc cctccgccta ttcagagagt atgcttcgtc   1020
acggcgtggg cgccaacatc ggcgcaggag ctggcggcac gggaagaaag ccgcaaccgc   1080
ggtcctcgac cttcaacgtc ccgggaggcc cgtccacgac tcccagacgt ctctgcttgt   1140
tgttctacgt cgtcgcggcg ttgtgcagag tccagcgcgc gcccgtcgtc gacttctgac   1200
aagcgataaa ttccgagacc agcgggagaa ggcggaacga gaggaggagg cgagctggcg   1260
tccttgcgac ctcgttgagc agttcaagcg agcagattga gcagcagtgc gtcgagtgag   1320
ccaactcacg ttctcatatc ggtccctgag cgatatcgat gaggcgaagg acgacgacga   1380
gcgaactgat ctcgcgctct ccctcttccc cttcactctt tccactcaga aacaacacgt   1440
gcgtcttctc tgaacgctat cagacaatcc aggaccatcg ctgaccgcgc gctcactcgt   1500
cgcctgactt catcgcccaa ccaacccgct cgtcaccgac tggatctctc cctcccctca   1560
caccacctgt tgcgctgcga tactcctctc acag                                1594
```

<210> SEQ ID NO 108
<211> LENGTH: 1396
<212> TYPE: DNA
<213> ORGANISM: Rhodotorula glutinis ATCC 204091

<400> SEQUENCE: 108

```
cggcgaagag gagggtgtt aggagggaga gctgtgcgag ggggagaggt cagtccgagc     60
acgatacgcg agcaggccaa gcggcttcat gttcactcca agctcgatgc ggtcgagaag    120
tacgagctcc ttgacgagtg aaagggagag aagagagact caccaacccc ggcgcgacct    180
tcacgaaccg caacttcccc tcacacgcct cactacacgc cctctcaaac acctcgagcg    240
tcgcgtagtg cgagagcttg aagaataggt aggcgaggaa ggaggaggcg aagagggcgg    300
ccatctagcg aacaagttgg gttagctggg tgggggaaag ggaagagggg aggaagaggg    360
ggagggtacc atgatccagc ctatgtcgac ttgcagttgg aggggcatcc tgtgcgcgta    420
ctggcgtcag cggcggacga caaggcaggt agacgagaga gggggccggg gaacgcactc    480
gcagttgcgc acgtccgaga ggaacatgta cgagtagccg gcccacatga cgctcagcag    540
cgccgcaagc gtgtagtgga agatgagcct gcccattggc agtcagcgcc gacgcggaca    600
aactctgggt gaagagaaag gagagaacgc accacttctc ctccttcagc actcccctcg    660
cccagaccgc ccccaacaca atacagacga gatcgatagt tgccccagtc acagcgagcg    720
```

```
cgagttggct gtagacgagg tgtttgagcc gtctgtgggc gggagaggtg cggatgcgct    780
ggatctgcgc gggggagagt tttgggacga agttggggtc gtcggccatg gtgagcccgt    840
cgtagtagct gtctgagcga gcctagtagt gcgctggacg agcagagccc agagtcgaga    900
cgagcgtgag caggagacga ggttcggagt gtccgcggag ggcgacgaga cgacgagcga    960
gcttgggaga agcgcgagca tgtccagcag cgtagtctcg aggccgccag cagtagtaga   1020
gcacagcaat gaggcaggaa ggagcgcaag ggagggaaag agcgcgacga agggtcgagg   1080
tgatgaagtc caaggacagg gggaccaccc tcgcccgctt ctccctcgct ctccccacga   1140
agtgaccact tgtaaggctg gtaattcatt ccatacagtc tacatacact tgcagccatc   1200
cgcttcccct gcgatgccag tttcggtcac cgtgggactc cgatgcgatg atgcggccga   1260
gttggcttcc tcgacccgct ctcacacgct cataccagcc tctcccagcc tgctaccgct   1320
ctctggctct gccaaacacc cactcgagca cacccaccca accagcgaac tcgcccagcc   1380
tttgaaccgc aatggc                                                   1396
```

<210> SEQ ID NO 109
<211> LENGTH: 1468
<212> TYPE: DNA
<213> ORGANISM: Rhodotorula graminis strain WP1

<400> SEQUENCE: 109

```
cgtgcagaag gaacccgagg aggtcagtgc gcggtcgaga gaggaaaagg agagagagac     60
gcaccgagcg aggcattgcg cgtgccagcg ctcagcctgt acctcgcgac tgctgatgaa    120
agcgtcgtcg ccgcccgaca tgaccgccgc ctcgctcgac tggtcgccga cgacgtcgac    180
gccggaagga ggtgcgcccc agccgcaggc ggcgcgcctc aggctcacgt cgacgtgccg    240
gacgttcgac gctcgccacg ggtcgtgctc gagggctttg acgacgagct cgtcgcgctc    300
ggcgctgccg cacccattgg cgaacgtgac gtcctggccg agcacctcct gcgcgatggc    360
gcgccacagg cggcagacgg acgcgacctg gcggtaggcg cacgtgcgac aggtgaccgt    420
gaggtgcgca aactggccgt ggacgaggag aggctcagag atgagcgagg tcgtgagggc    480
gtggcggatg accttgagga ggagctcgtg cggcacggca gagagggtcg gcatgatggt    540
gtgcggcgcg gtcggcagtc tcgagagaga tgtgtagagg aagaacgatg tcgccagatc    600
ggtcgagcag gagccggtgc gaggcggctc gaggaccgtc gcggtcgagg accggtcacg    660
gctggacgat cgaggagacg cgcccccgtc gagcgcagcg ccagacgca agcgagcacc    720 tttgaggctg tactccaaaa cccggagcgc cggctcggga gccgtgtcct cgcaggatcc    780
tcggtcgaca gcgccgagtc ggagagggcc agccgacctc gggccgcccg acgcccggcc    840
gcagctcctc cggtccgacc tgcagctcat cccagcagat cgactttgag agcgaagccc    900
ccaggaagct gcctgagcga cctcgaggct tgggaaggtc gccgagccac ggctgggaga    960
gcgagctccc tcacagtcga gaccggctcc aagtcgaatc gcacactcgt agctgcaccg   1020
caaaagtgtg tgcagagctg gagcgagcga ccgcgcgagg cgcgagggtc gcgagaaagc   1080
gggcgagcgg tgcgagtgcg cccgagacgc cgagagaggg cgcgagggcg agcgggcctc   1140
gcgagccctc tggagcgtgc agaggcggcg gggaggagca gagtgaggga gggaagaccc   1200
tccagagctg gcaggagcca acggagcgcg gaaatcagtg agatcgatgc ggttctcgag   1260
acgattcgac cgcccctcgtc gtcaacgtcg cgccctcgtc cctctcctct tccaccacc   1320 tctccggtac ctctacacga gtgcgttctg tcccgagatc tgatctcgac gccgcacggc   1380
```

```
actgactgac cgcccacctc gtctccctcg cccgtcccac actctcccct ccgacctccc   1440
acctcctcgc tcaacccctc tcgcctcg                                      1468

<210> SEQ ID NO 110
<211> LENGTH: 1520
<212> TYPE: DNA
<213> ORGANISM: Rhodotorula graminis strain WP1

<400> SEQUENCE: 110
cgggaggatt gatgatcggg ttgcggtaca aggcgaggcc gaggacgagc tggagggcgc     60
cgaggacgag ggtcgagatg ccgagctgcg aggggacgag gccgccaatc gaggtcgtgt    120
cagacggccg taccgagtga tctcatagcg ggtccgccga cgcagaaaga cgaagagaaa    180
ctcacgacga gggggctcag cttgacaaag ttgagctttg tcgtgcagcc agacgagctg    240
cgataggagc gagggtcagt gcgcccgctc tcggatgaat gcgcagtcga ggagggacag    300
gggcgcacca ggtgacgatg aacatgtcga ggacgccgta ctgcagcatc ttgcggaaga    360
ggtagaaatg ccacgccgaa gcgaaggtga cggcaaactg cgagagggac gaggtcagtg    420
cgagggtccg caacagggag agggcactcg tcacggacca tcatccagcc caggtcgatc    480
tgtagctgat cagggaagct gtgccgggtg cgagagaggt caatgtcgaa gcttggcagc    540
tcgtcgagga agaagaggac ggcgagggac gcacgccatg aacttgatgt gacgctcgaa    600
gacgaccgag tagccgagcc acatcattgt gaggacgccg cgcagacgt agtggaagat    660 gaacctgaga gggcaagagg tcagtctcga acgagggag gaagccggct cgagcaggac    720
gaggcgggcg caacgacgc accatttctc ggcggcgacg atattgcgag cccacacggc    780
cccgagcact agacaggtga tgttggcgac cgcgccgccg acggcgagag cgagaacgct    840
gtagacgaag tgcttgatgc gtcggtggat tggcgctcgt cggatcctcg cgatctgggc    900
cttggtgagc ggtggtggcg ggccaagcgg tgggccagca gctgtgctca tcgcagcagc    960
ggtgcggcgc aagagcgact gtggagctcg agggagagga gcgcggcagg ggaaagcgag   1020
accgaggagg agcgagcgcg gacaggcgag gcggaccgga cgttccggtg cggctcgact   1080
ggcgtgcgag acgagcaggc cgtcgccgga agcagccgtg tccggcggaa agagccaggc   1140
gcgcgagcgg ggcggagcag acagcggcgg tccgagcgcg cggggcaggt tcgacgaaag   1200
tcgggctcgg gtcaggctcg cgcgagcgca tgagatgccg tcgagcgagc ccatgtacag   1260
agtcgagcga gagagcgaag tgcgtggaag gagagtggtc caagagtgga gcgccgtgga   1320
gatgagacag atgatggcga acctcggcca cagcctctcg gtcctgccac agcagctctg   1380
tgagtctccc tgacccgcca gcccgcgctt cagaactcac agaccaccta cacagactcg   1440
cgcaccagct cgaaccgcgc cagaccaccg cctcgccgcc tccccacctc gactgcttcc   1500
gaacctcaca agctcgacca                                              1520

<210> SEQ ID NO 111
<211> LENGTH: 1210
<212> TYPE: DNA
<213> ORGANISM: Rhodotorula graminis strain WP1

<400> SEQUENCE: 111 gcgagggaa gggcaggaga gtcgccggaa caccgggcaa ggagacaagg acaaagagcg      60
agcgcgcacg caccgtctgg cggtcgggct gggtggggcg ggtccgagta gcgctgaccg    120
aagagcgagg aggaggaaaa gcgagcgcgg cgggcgtggg aaggagggca aggagggcgg    180
cggcgacgcc aaaaaaggcc agattcgcgg ggcagtgatc gagtgccgtc cgcgagctca    240
```

```
accagcgagc gctctctcgc gcgcagcggt gcgcttcttt cgccagccga tgcgcaccgt    300
tcagaagcac gtcgcccgca ccgagagcgc ctcctcgcga gcctgtgacc acctcgtcga    360
cccgcttccc gcggcttttc tcgccggcct ggaccgccgc tatcagatcg tgcccatgag    420
acaagcgact cgtcgaaagg acgacgatct cgtagtactg ggtccctgcg caacgctcag    480
ccgtccgtcc ccgtcaaagt gcttcggcgg aggggaccgt gcgcgagacg cccaagttgg    540
cctcctcaag tcggtagatc cagcttaacg ctatcaaggg ttgcatggtg tagttggtca    600
tcacgtcagt ttaacattca gttcactgaa ggtcctcagt caaacctggg gtgcgatcac    660 cttttttggct cggcggcatt gcgccctttac acccgcacgg gtctacttcc ctttgcaagc    720
gaccaagcga agcatcctct cgctcgtaaa gctgccggcg aggaggtcag acgggttggc    780
gggccgtcga aggtcggctc accctcaacg ctgccggctg accacgccag gcgagctatc    840
attgctttga aagcttcgaa aacgcccagg catgcacaga aagccgcccg cgagaggctc    900
aagttggcgc cgagctgcgg tcgagagacg acgacgacgg gggagctccc tcgcctctcc    960
tcctttctct cccaccccat cagcccaagt gagtcgctcg ctcttccgca agggtcagcg    1020
cacgcgttgc tccgcgacag ggcagcgcgt gcgctcacca gggtcccccg ttcgcccggc    1080
gagttggcac tgacgaggtg ccttgccccc ctccgctccc ctccccttttg gcctcctctc    1140 tcgcacgcac actctctccc tgcacccctt gcaccttccc gacactctcc ccccccttcc    1200
caccgtccga                                                          1210
```

<210> SEQ ID NO 112
<211> LENGTH: 1495
<212> TYPE: DNA
<213> ORGANISM: Rhodotorula graminis strain WP1

<400> SEQUENCE: 112

```
actacctcgt cacgacccag ggtgcgttcc ccttctcgcc gcgtccacag ccacgacgtt     60
gcgagtccct aacgcgtccg ctcccccgtg caggtggtcc tccgcacggc gcctacacgc    120
agacatcgtc gacgccgtcg cacgacgccc actttgccgt ccagaccctg tcgcgcttcg    180
gcctcgcgta cctcctcgcg tcgtccaaca cgctcaagga cacgtggctg agcgtgtgcg    240
cgcccgccgg cgccaagggc cccgaacccg acgtcgacga cctcgagctc gagaagcgcg    300
agcaccgcga caagtggctc ctcgggcgca tcatgggcca gggcaagcag gactcggcgc    360
tcggggacgc agtcgctgtc gtgagtcctc tactctcggc cgttctcgag acttggggtg    420
cgagattgac cttgcgctcc cgcctctcgc ttgcagcaat tccacaagca ctttccgcac    480
ctgcgctcgg cgcacctctt ccccggcttt gtctttacgt gcgtccctct cgttccccc     540 tctctccacg tgcgccacca gcctgactcg ccccctcgcct gccccgtccc gcagcaacgc    600
cctcgcgtcg acctcgctcg tccccctcgcc gatcctgtcg ctgtacaacc tcgtcgggcc    660
cctcgcggcg cgcatcctgc cctttggcaa cctgcccgag acgtacgccg acgtgcccgt    720
gtacgtcgcg gccaacccgg cagcgcgcag ccaagggctc gagtactgca acgagcgcat    780
gaagccgctc gggagcccgg cgtgggccga gggcgcgacg ggcgcaaagg tgtgggacgg    840
gctgagggcc atgatcgagg agtgagctgg tgggcgggca agcgaggagc cggagaggag    900
gggcggaacg tgtttgagaa ggtcgcgctt tgctcgtcgg tcgcgggcgc agccgtggct    960
gtagccagtc tcgctttgca gtgtcactct tgtacatagc tgagcaaggc ctagcgtcgc   1020
gagagagctg cgctgtggcg cctggtcgag gcccgagagc gtcgcgctca ggggcgagct   1080
```

```
gctcgcggct caccaaggggg ctcgagcggt gcgcgctcga caggggaccg agagctgcag    1140
gagacagacc ggaggaaaaa gctctggcga gcgaggagcg gggccacact gagtctgggg    1200
aagcgacgga cgaggatgag cgcatccact cttgagtttc gccgaggcgc gagctggcgg    1260
tcgacaaccg agcaagctcc tcctcttcct ccaccacact cgccctagc acacgtgagt     1320 ctcgctccct cgccactgtc gaccagcaca cgctcgtcca ccgccctgtg cgccctgtgc    1380
ggcttgcggt cgagcgaggc gcgggtcgg gtctctgcca cccgaggaac catcgatgtc     1440
gctgacgctt cgctcctcgt cctcctcctc ctcccacccg ccgcagctac ctaca         1495
```

<210> SEQ ID NO 113
<211> LENGTH: 1634
<212> TYPE: DNA
<213> ORGANISM: Rhodotorula glutinis ATCC 204091

<400> SEQUENCE: 113

```
cctgaagctg tacatcgagg tggacgacag cgcgggcaag gatgcgccag caatcgtttg      60
tgggtcgctt ctttcctcgc agcacgcttt tgtcggctcc ctgatcagca cacaagctaa     120
ctaacgctct ggtttcgctg gcagtcatgc acggccttgg ctcgtcaacc tcgttctggg    180
aagcgccctt ctcccgctca aacctgtcct cccgcttccg cctcatccgc tacgacttcg    240
acggccacgg tctctcgccc gtctcgtccc tcgacgcagc agatgacggc gccatgatcc    300
cgctcgacga cctcgtcggg gacttggcgg ctgtgatcga gtgggctggg gtggagaagg    360
ttgcgggagt tgttggacac tcgatgagcg ggctggtggc gagcacattt gcggccaagt    420
acccgcagaa gctcgacaag ctcggtgagt cgcattgaac cttcctccgc cgtctcttct    480
ccgctgacga ttcgtcgact tggccctgct tctcgcgcag tcctcctcgg cgcaatgcgc    540
tctctgaacc ctaccgtcca aagcaacatg ctcaagcgag ccgatacagt cctcgaatcc    600
ggcctctcag caatcgtcgc acaagtcgtc tccgccgctt tgtccgacaa gtcaaagcag    660
gactcgcccc tctcggcagc gatggtgcga acgctcgtgc ttggaacgga cccgagaggg    720
tacgcggcgg cgtgtagggc gcttgcgggt gcgaaggacc cggattactc gagcatcaag    780
gccgagacgt tgggtgcgtt cgcttgttct ccttcctctg cttttctccc agcaactgac    840
gcaagcgtct gcaacacagt cgtcgcaggc gagtttgact acctctcgaa caaggagacg    900
accgacgcgc tggtcaacga catcccgggc gcggagaagg tccagatgga cagtgtcggc    960
cactggcacg ccgtcgagga ccccgttgga ctcgccaaga tcctcgatgg gttcttcttg   1020
caggggaaat gaggttggga aggggggata gactggggag aacggcaggt gcgtacgcag   1080
cggacgtcgg tcgggaggac tttttcgggg aggatattcg ctgactgact ccgacgtcgc   1140
tttcctcctt gcagtatctt cagaagggat gggaggaggc gaactgcaag ggtaatgaac   1200
gagacaacgc cgagggagga agcgccggaa ctctcggggg cgaagaagga gtggtgtctt   1260
cgccagcgaa cagcttccgg ggtgggttgg acagcgccag tagaattcca gcgtcgcaac   1320
agagctctag tcgaccgcga tcacccacaa ggacgagagc gggtcgcgcc ttgtccgctt   1380
ccccatcctc gtcctgctct tgctctcttc cctaccacac tctcccgctt gcgggctctc   1440
tttctcgctt ggcgctcctg ctaccgctac tctagactct cctagtctcc ctgcacaacc   1500
atccctatcc cctccgcctc tctcgcacac ccccacagc ttcgttcccc aacttcactt    1560
ccgatgccgt gcgtcgcctc cctttcgcct ggcgggcccg cgcctgcttc cgaggacaac    1620
tactgattgt ggga                                                     1634
```

<210> SEQ ID NO 114
<211> LENGTH: 1438
<212> TYPE: DNA
<213> ORGANISM: Rhodosporidium toruloides

<400> SEQUENCE: 114

```
ggcgcgctag tctgcagaac tacgccctct cacacccaac ttccgactcg accggcggta      60
cgagcacgac ctacttctac tgcctgccat cgacatccgg gcgggtcgct gcctaccctg     120
tgcgttctgc gccctccctc gtctcgggag gcagtgtctg acagaagctt tgcgcgcagt     180
accccgtcaa gatgcaactc tacgcaacgt tcggcacaga agtcgccaag ctccgcgcat     240
cgccgcctca agctctcgcg ctgcccgacg tgtcgtcta ttacgaggcg gagaagctcg      300
agttgccggc tttgccagcg gcggtcaagg ttgaggtgga gacggagaag gcgggagtag     360
cggggggagga caatgaggcg aagggtgaga tggtgctggt ggagactctt acggtggagc    420
aggaggagat tgaattgggc tcgggagtcg tgcagattga ggagtcgttg ctcgtcaagc    480
tggaggtcag cggctgatcc ttccgttcgt tgcaaggatc gtctgcatgt ttcgcttctc     540
tcaatgacac aacctggaga gcgctcccgt cagcgagaat cgaggacatt ccgcagctcg     600
tgagcaagcg gaggtgcgag gctccctcga aagctgcgcc tcttcagacg gcttgttctc    660
tcctgctctg gtgggctggc ctgacatgta atgtgctccg ccgcaagtcc gtcgtcggtc    720
tcaattcgac gttgaaaggg catagcgcaa ggaagaaccc tctgcggaca tgcagaatta    780
ctggctcgcc tgctccttcg tctactggaa taagtcctgt ctcgttaaag ccccaacgtc    840
gttttctcgac gtttgtaagg cgcaagaggt gctatgggct acgcaggaag ctgagaggac   900
atagaagtcg ggggaggaac ggcgcagagc ggcagttgcg gaagcatgag gaaagcgaga    960
cggtccagca tctgcagcgc caatccgcaa tctcctggtt gagcctgcac cggaagcgtc   1020
ggaacagtat gcgcagagtc gaacgcaagt aagaaagacg caccctcaca ctcgcttact   1080
tcgagccata caacggatca aagctgcgcg tatctcggct tgtaagggcc ggaaagcaac   1140
ctcggagatg gacacgtcac atcaccaact tatcgatctc ggccgtcgac gtcgcagaga   1200
gggcgagaga agcggtgaag gagggaaaca acccctcgag agcatgatcc gaccgaatct   1260
gcagcgcagg aagccgttac aagcccgcct cgagcgcagg tcgggtccag ccgggggacg   1320
aaacgcgcga ggctgattcg tgagcgaagg aagccgcatc gacaagttcg ctccccttttg  1380
ccctctttcc catcacccgt tctcgcctta cccgctcaga caacaccag atcactca      1438
```

<210> SEQ ID NO 115
<211> LENGTH: 660
<212> TYPE: DNA
<213> ORGANISM: Ustilago maydis

<400> SEQUENCE: 115

```
ggcgcgctag tccttaaaac tgaaggcggg aaacgacaat ctgatccaag ctcaagctaa     60
gctctagtga ttagatcttg ctgataggca ggtttgcttg gagaatgggg ggaaaagact    120
gaccgaagaa acagcgagat ctagaagtga taagcggaaa gaatctgact tgctgtgatc   180
agcagccaat tttttttttcg tttttttttt ttcactccac atcgtcgtgc gtgcacggtc   240
tgcatgtgta aattgtattc atcgaaagcc acagttgaat acatcagccc gatgtggatt    300
tcgaaaacca attaatcttg gaattcacgc gctcagatca gtccatagag tcgacttcgg    360
ctgtttccaa gagcttcttc tctgcgaggt ggttgcccgt gtttctcgct gggaaaaaag    420
gatcgattat tattcgcttc tacctcgctc gcacccttgg cctgctgaag gaaacagcgc    480
```

| | |
|---|---|
| cgagactcgg tcacggttgc tgggctccgt gttgatgctg ggacggcgca aagtggggcc | 540 |
| cgcgcactct tcgagccaag gacctcactc ttcaagaaca agcgctgtcg ccatcgtctt | 600 |
| cttctttctg ctccaccatc gaatctttct ttctcgtttc gaaaccaaaa cactcttcca | 660 |

<210> SEQ ID NO 116
<211> LENGTH: 951
<212> TYPE: DNA
<213> ORGANISM: Rhodotorula graminis strain WP1

<400> SEQUENCE: 116

| | |
|---|---|
| cctacgtcta cgtcaagggc aatgccgacg tgaccaaggc catcggccag gacctcgcct | 60 |
| tcttctcggt ccctgtcgag ctcggcgtgc gtcccgccgc tctctctctc tctttctctc | 120 |
| ggccgcgcct cacgtgatcc acgacgtcgt actgacccct tgcgaatgtgc gcgcccgcag | 180 |
| cccaacggcg tcgagaaggt gcacccgctc ggcgacctga cggcgttcga gaaggagctc | 240 |
| ctcgaggcgt gcctcggcga gctgcccggg tccatctcca agggcgagtc gttcatccag | 300 |
| ggctccaagc tctgactcgc cggcgcatcg acgggcgcga gccacaaggc gaggatgtga | 360 |
| gaggaggcgt ttcctccacc ttggaccccca tctgccgcct cccttctctt ctctttcttt | 420 |
| cccttcctct ctctctctct ctctctcgtt ctcctccttc tgggcctctc ggacctcttc | 480 |
| ctcgccgtcg actcgtgaaa atgcagtgcg cgtttctgta ccttgtcctg cgagagagat | 540 |
| ctggttctgc gagggtgagt cgttgccttg gccgtggcac gcctcgccgc agcgagagag | 600 |
| aagaggccac ggtccaggac gacgacgacg aggaggaagc gcaaaaggcg agacaccgag | 660 |
| tgccatcgat tccccgctcg aacctgctca cggctgtcga aggcggtgcg ccacggtgct | 720 |
| tgcgggagcg aaagcaagct ggcgtcgtcc tcttgaactg gttcgagtcc gtgagggcgg | 780 |
| cgacgagaac tcaggcgagg tgctcgcgtc ggaacaagcc gggcttgtgg tcagggagc | 840 |
| gagagcgagg cagcgccgtc gtcgccgagg caagagcggc atcgacaagt tggcccgtcg | 900 |
| cctctcgctc cctcttctcc tcctcccacc accacctttc tccagctcga a | 951 |

<210> SEQ ID NO 117
<211> LENGTH: 2136
<212> TYPE: DNA
<213> ORGANISM: Rhodotorula glutinis ATCC 204091

<400> SEQUENCE: 117

| | |
|---|---|
| ccaccatctc ctcgtcgctt cttccctctc cttcggcgcc cacaccgctt cgcagggctc | 60 |
| acggactgct cacatcgttt gtgtgcgtcg ctgtgcatgt ccacgcacca ctcccagccc | 120 |
| ccacgagcgc ctcaaaagac gcggacgcag acgcccgccg aacgacggca cgcccctctt | 180 |
| ctcactagcg cgacgaacca gctgcgacga ttcgtgcgct tatgttagcc ggacttctgg | 240 |
| cttgctttgc gctgctgcgt ccgtcttgtg gtgcggatcg gctcgatggg ggtttgctcg | 300 |
| tttgctggga cacggtcgcc tctccctcct cctcttcact cctcgttagc tttctacgct | 360 |
| cattggttct gcgaaccatc tacatcacgc tcgctcgtca tgctcgtact acgatcaaca | 420 |
| cccctgctcg tcgtgctttc cctcctctcc gtcctctcgg ccgcgtccag cgacttgccc | 480 |
| agccaacttc ccccgcacgc cggtgagtct cccacacttc cttgcgaccc caacccagca | 540 |
| tctgacatcc gcatcacgca gccctcccgc cttccactc ctccctcttc accgactcct | 600 |
| cctcctcctc cctgattcc tcgtcccctca aagcccgca gcctcttccc ttcaaaatca | 660 |
| agcgcccccg ctcgctcgaa caagtgcagc agaacctcgg gaagaggctg gcgaagcgcg | 720 |
| gcgaggaggg gagtaagacg gagagggtgc cgtttggtca gaggagtgcg acggcggcga | 780 |

```
gtgcgggtgg acaaggtgga gcggggacgg ggagggcgac gcagcgcgtt acgggcggag      840
gaagcagagg tgcaggagga ggcggaggga gtgtcgcggc tgctcagcct gtcccttcga      900
ctacccagac ggtcgagaca ggctctaaga tcgtctcgac tggtcttctg accgtagcgt      960
cgccgtcgac ggcagatgga ggaggcggga cggtcaccca ggtcgagacg gcctcctcag     1020
gggtattgat caccagcacg gcgggagcgg cgagttcagc ggcggcgtcg acgtcgcta      1080 gcgcacaggc agcggaggcg acgtcgagta cgagcatgat cagcggagga gcggcggctg     1140
gcgggagttt aagcaggatg ctggcgggag gagttgcggg tgcagccctg atcctcctcg     1200
tgcggtgagc aggcgaagcg aggagctcat gtagatacag catagacagt atatatcgcc     1260
aggatagctt gcaacagccg ccggtcggtt tattccattg tcctcgaccc catgcgaagg     1320
cgagctctgc tcgtcagctg gccaagctgg ccagcagacg agcgttgggg tggcggaacg     1380
ccaacggcat ggagtaaagc agccgtgagg atgacggagg agctcgggcg aggtgatggg     1440
gattctagca ggaacagcag agcggcgagg aggagaggaa ccggaagcac agtctcgtgg     1500
ccgcttgttg cagatcccag tgtcgctaga gtgctcgtcg tcatcagagc gagtgaacaa     1560
agcgatgccc tgaagaacga tgagcgaatg agtcgaagcg gcgtctaccg gtgaactcgg     1620
ggtgtggcaa atgagcgaga cgaggagtgc ccgccagagt tgccacgtcg accccacgtc     1680
ggaatcgacg ttgatagagt gaacgaagcc attgcagacc ccagaaggtg gccatgttgt     1740
ggaagcgagg gcaggagcga gggagaagg cgaggaggag gaggggctgg ggaagcccgt     1800
ccgggaatgg cgcagctggg tgccggggat gtgcgcgagt ggcggaggag tcgagcgtga     1860
gagttctgga acacggggcg cgcacaaggg tcgagggccg tgacgagttc gccgggcggt     1920
ggtcgggctg agggcgagcg cgcgttgggg acgacgacgc ccgacgccct cgctcttcgt     1980
cctcaccgct tcccggagaa ctttgctgta ctctgcttct cccttcacac tctcacaccc     2040
actcacacac ccttccatcc acacacaagc tatccgcaca cctctcacac ccgaccccag     2100
ctcgccccat cctcttcgca cccggctcat cgaaaa                              2136
```

<210> SEQ ID NO 118
<211> LENGTH: 997
<212> TYPE: DNA
<213> ORGANISM: Sporobolomyces roseus

<400> SEQUENCE: 118

```
ccgaagttat acctcagagg tctcaaaaac gaaaaagtca tgcaagaatc tcctttgacg       60
tgagggttat ttctcttcct ctagtagtct acgagaatcg caaagatcgg aaaactgatg      120
catctttgtg ttcacgggtt agcgatttga tcttttcgat tcccaaaatc gtatcgttcc      180
tgtcgcaggg aactacgctc aaagccggca ctctgatcat cacgggagtg agttttgagc      240
tctccctcta tgagagtgca aggttcgtcg ctgatggtgt aatccgctca tgccttcccc      300
tctaccttct cctttgtcca ttctctctac tacggttgtc acatcttcct tctccgacag      360
accccgcacg gaattggagc gtactcgaat cctccggaat tcttcaagga cggagacgtc      420
ttcagggtcg agatctcggg aggcatcggg agtttggtca acaagatcga atatgaaaag      480
tagataatcc gttactcagg tcaatggtat ggcttcgaag atgctggaat cagccggaaa      540
gcaaagctgg agagaaaaat cgagattgcg aaacgtgcga tgtcatttcg tttcgagctc      600
gcaaccatct cgtatccctc tgagctacat acaaacgtca ctacggcctc ggagtgactc      660
cctgcgagcg gattgaagga gatcacggtc gaatcagcta gaccttcgca acgttttcgc      720
```

| | | | | |
|---|---|---|---|---|
| gctcgcacgt | tcttatcgat | ctactgagat | tgactcgaaa | aagtcttctc tcacggtcga | 780 |
| ttgaactttg | aatgaactct | caggttgcgc | gagagccaat | acgagccgac cagaggcaat | 840 |
| tcggagcttc | ccggaacgtt | ccaaggagag | ggattttccg | agagattacg attgcgagat | 900 |
| agaaaaaagg | ctagctttcg | atttcgagag | agattacttt | caagttcgct gcttccaact | 960 |
| cttgctccaa | cccctccac | tccttctcta | caaaaca | | 997 |